(12) United States Patent
Luo et al.

(10) Patent No.: US 6,569,658 B1
(45) Date of Patent: May 27, 2003

(54) GERMINAL CENTER KINASE CELL CYCLE PROTEINS

(75) Inventors: Ying Luo, Los Altos, CA (US); C. Alan Fu, San Mateo, CA (US); Mary Shen, Newark, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/645,791

(22) Filed: Aug. 24, 2000

Related U.S. Application Data

(62) Division of application No. 09/425,324, filed on Oct. 21, 1999.

(51) Int. Cl.$^7$ .......................... C12N 9/12; A61K 38/43; C07K 1/00; C07K 14/00; C07K 17/00
(52) U.S. Cl. ...................... 435/194; 424/94.1; 530/350
(58) Field of Search ...................... 530/350; 424/94.1; 435/194

(56) References Cited

U.S. PATENT DOCUMENTS 6,277,979 B1 * 8/2001 Bingham et al.

FOREIGN PATENT DOCUMENTS

| WO | WO 95/33819 A2 | 12/1995 |
|---|---|---|
| WO | WO 00/14212 A1 | 3/2000 |
| WO | WO 00/15805 A1 | 3/2000 |
| WO | WO 00/36124 A2 | 6/2000 |
| WO | WO 01/21799 A1 | 3/2001 |

OTHER PUBLICATIONS

Fu, et al., "TNIK, a Novel Member of the Germinal Center Kinase Family That Activates the c–Jun N–terminal Kinase Pathway and Regulates the Cytoskeleton," *J Biol Chem* 274(43):30729–30737 (1999).

Kitamura, et al., "Molecular Cloning of p125$^{NAP1}$, a Protein That Associates with an SH3 Domain of Nck," *Biochem Biophys Res Comm* 219:509–514 (1996).

Nagase et al., "Prediction of the Coding Sequences of Unidentified Human Genes. IX. The Complete Sequences of 100 New cDNA Clones from Brain Which Can Code for Large Proteins in vitro," *DNA Research* 5:31–39 (1998).

Rothe et al., "I–TRAF is a novel TRAF–interacting protein that regulates TRAF–mediated signal transduction," *Proc. Natl. Acad. Sci. USA* 93:8241–8246 (Aug. 1996).

Shi et al., "TNF–Mediated Activation of the Stress–Activated Protein Kinase Pathway: TNF Receptor–Associated Factor 2 Recruits and Activates Germinal Center Kinase Related," *J Immunol* 163:3279–3285 (Sep. 1999).

Suzuki et al., "Down–regulation of the INK4 Family of Cyclin–Dependent Kinase Inhibitors by Tax Protein of HTLV–1 through Two Distinct Mechanisms," *Virology* 259:384–391 (1999).

Ohara, O. et al., GenBank Accession No. AB011123, Apr. 10, 1998.

Herskowitz, "MAP Kinase Pathways in Yeast: For Mating and More," *Cell,* 80:187–197 (1995).

Bagrodia et al., "Cdc42 and PAK–mediated Signaling Leads to Jun Kinase and p38 Mitogen–activated Protein Kinase Activation", *J. Biol. Chem.,* 270:27995–27998 (1995).

Kyriakis et al., "Sounding the Alarm: Protein Kinase Cascades Activated by Stress and Inflammation", *J. Biol. Chem.,* 271:24313–24316 (1996).

Ip et al., "Signal transduction by the c–Jun N–terminal kinase (JNK)—from inflammation to development", *Curr. Opin. Cell Biol.,* 10:205–219 (1998).

Sells et al., "Human p21–activated kinase (Pak1) regulates actin organization in mammalian cells", *Curr. Biol.,* 7:202–210 (1997).

Kyriakis, J., "Signaling by the Germinal Center Kinase Family of Protein Kinases", *J. Biol. Chem.,* 274:5259–5262 (1999).

Pombo et al., "Activation of the SAPK pathway by the human STE20 homologue germinal centre kinase", *Nature,* 377:750:754 (1995).

Shi et al., "Activation of Stress–activated Protein Kinase/ c–Jun N–terminal Kinase, but not NF–κB, by the Tumor Necrosis Factor (TNF) Receptor 1 through a TNF Receptor–associated Factor 2– and Germinal Center Kinase Related–dependent Pathway", *J. Biol. Chem.,* 272:32102–32107 (1997).

Kiefer et al., "HPK1, a hematopoietic protein kinase activating the SAPK/JNK pathway", *EMBO J.,* 15:7013–7025 (1996).

Diener et al, "Activation of the c–Jun N–terminal kinase pathway by a novel protein kinase related to human germinal center kinase", *Proc. Natl. Acad. Sci. USA,* 94:9687–9692 (1997).

(List continued on next page.)

*Primary Examiner*—Gary Kunz
*Assistant Examiner*—Robert S. Landsman
(74) *Attorney, Agent, or Firm*—Townsend and Townsend and Crew LLP

(57) ABSTRACT

The present invention is directed to novel polypeptides, nucleic acids and related molecules which have an effect on or are related to the cell cycle. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention. Further provided by the present invention are methods for identifying novel compositions which mediate cell cycle bioactivity, and the use of such compositions in diagnosis and treatment of disease.

16 Claims, 35 Drawing Sheets

OTHER PUBLICATIONS

Yao et al., "A Novel Human STE20–related Protein Kinase, HGK, That Specifically Activates the c–Jun N–terminal Kinase Signaling Pathway", *J. Biol. Chem.*, 274:2118–2125 (1999).

Su et al., "NIK is a new Ste20–related kinase that binds NCK and MEKK1 and activates the SAPK/JNK cascade via a conserved regulatory domain", *EMBO J.*, 16:1279–1290 (1997).

Yuasa et al., "Tumor Necrosis Factor Signaling to Stress––activated Protein Kinase (SAPK)/Jun $NH_2$–terminal Kinase (JNK) and p38", *J. Biol. Chem.*, 273:22681–22692 (1998).

Eichinger et al., "Characterization and Cloning of a Dictyostelium Ste20–like Protein Kinase That Phosphorylates the Actin–binding Protein Severin", *J. Biol. Chem.*, 273:12952–12959 (1998).

\* cited by examiner

```
TNIK    1   MASDSPARSLDEIDLSALRDPAGIFELVELVGNGTYGQVYKGRHVKTGQLAAIKVMDVTGDEEEEIKQEINMLKKYSHHR
NIK     1   MANDSPAKSLVDIDLSSLRDPAGIFELVEVVGNGTYGQVYKGRHVKT-VTAAIKVMDVTEDEEEEITLEINMLKKYSHHR

TNIK   81   NIATYYGAFIKKNPPGMDDQLWLVMEFCGAGSVTDLIKNTKGNTLKEEWIAYICREILRGLSHLHQHKVIHRDIKGQNVL
NIK    80   NIATYYGAFIKKSPPGHDDQLWLVMEFCGAGSITDLVKNTKGNTLKEDWIAYISREILRGLAHLHIHEVIHRDIKGQNVL

TNIK  161   LTENAEVKLVDFGVSAQLDRTVGRRNTFIGTPYWMAPEVIACDENPDATYDFKSDLWSLGITAIEMAEGAPPLCDMHPMR
NIK   160   LTENAEVKLVDFGVSAQLDRTVGRRNTFIGTPYWMAPEVIACDENPDATYDYRSDLWSCGITAIEMAEGGPPLCDMHPMR

TNIK  241   ALFLIPRNPAPRLKSKKWSKKFQSFIESCLVKNHSQRPATEQLMKHPFIRDQPNERQVRIQLKDHIDRTKKKRGEKDETE
NIK   240   ALFLIPRNPPPRLKSKKWSKKFFSFIEGCLVKNYMQRPSTEQLLKHPFIRDQPNERQVRIQLKDHIDRTRKKRGEKDETE

TNIK  321   YEYSGSEEEEEN--DSGEPSSIENLPGESTLRRDFLRLQLANKERSEALRRQQLEQQ--RENEEHKRQLLAERQKRIE
NIK   320   YEYSGSEEEEEVPEQEGEPSSIVNVPGESTLRRDFLRLQQENKERSEALRRQQLLQEQQLREQQEYKRQLLAERQKRIE

TNIK  397   EQKEQRRRLEEQQRREKELRKQQEREQRR------HYEEQMRR--EEERRRAEHEQEYIRRQLEEEQRQLE
NIK   400   QQKEQRRRLEEQQRREREARRQQEREQRREQEEKRRLEELERRKEEERRRAEEEKRRVEREQEYIRRQLEEEQRHLE

TNIK  460   ILQQQLLHEQALLLEYKRKQLEEQRQAERLQRQLKQERDYLVSLQHRQEQRPVEKKPLYHYKEGMSPSEKPAWAKEVEE
NIK   480   ILQQQLLQEQAMLLHDHRRPHAQQ-QPPPQQQDRS--------------------KPSFHAPE---P--KP--HYDPAD

TNIK  540   RSRLNRQSSPAMPHKVANRISDPNIPPRSESFSISGVQPARTPPMLRPVDPQIPHLVAVKSQGPALTASQSVHEQPTKGL
NIK   532   RAREVQWS------HLASLKN---NVSPVSRSHSFSDPSPKFAHHHLRSQDPCPP---SR---------------SEGL

TNIK  620   SGFQEALNVTSHRVEMPRQNSDPTSENPLPTRIEKFDRSSWIRQEED-IPPKVFQRTTSISPALARKNSPGNGSALGPR
NIK   584   S-------------------QSSDSKSE-VPEPT----QKAWSRSDSDEVPPRVFVRTTSRPVLSRRDSPLGGGQQNS

TNIK  699   LGSQPIRASNPDLRRTEPILESPLQRTSSGSSSSSTPSSGSSSSSGSSGSNSGSQP----GSHPGSQSGSGERFRVRSSSKSEGSPSPRQESAA
NIK   640   QAGQRNSTSSIEPRLLWERVEKLVPRPGSGSSSGSSGSNSGSQP----GSHPGSQSGSGERFRVRSSSKSEGSPSPRQESAA
```

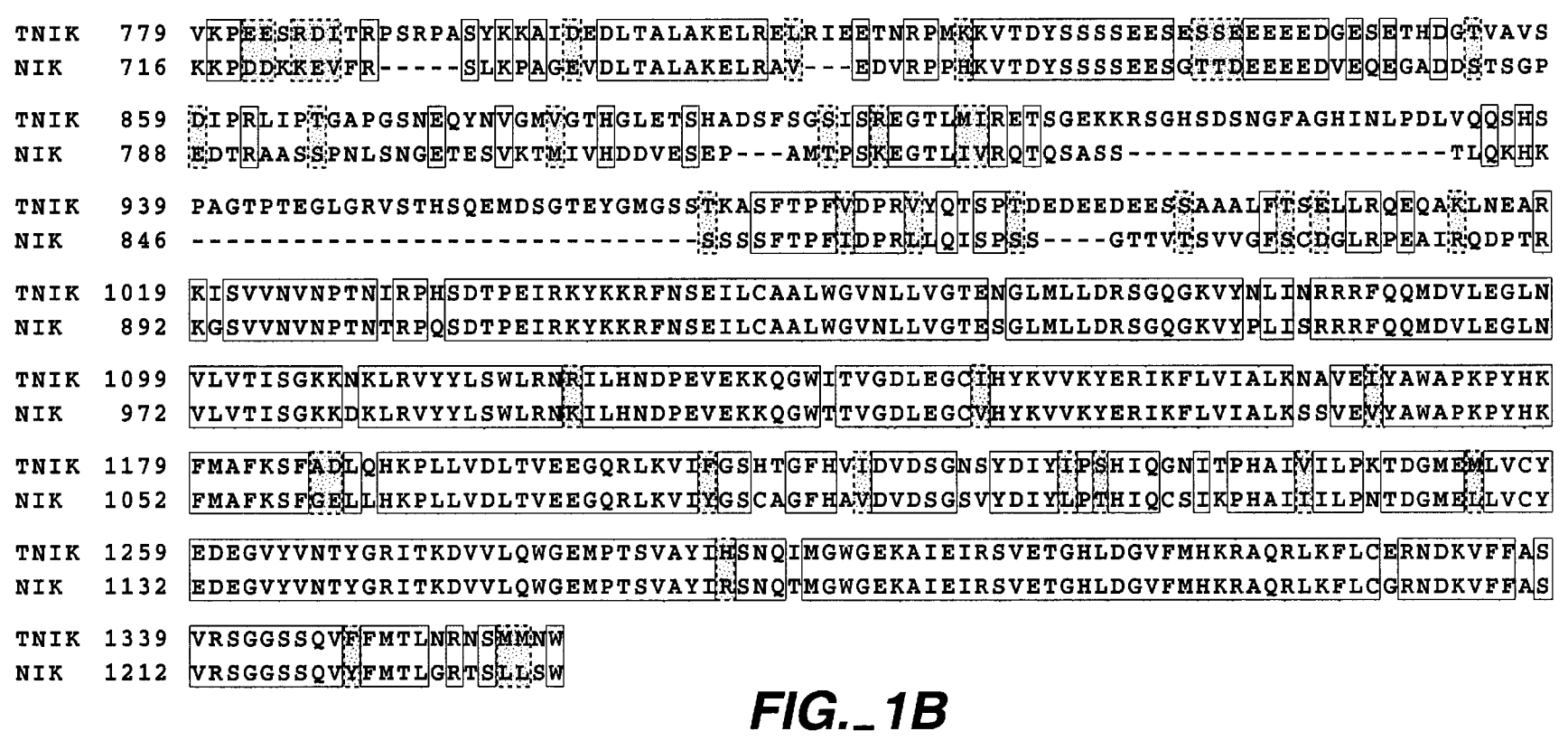

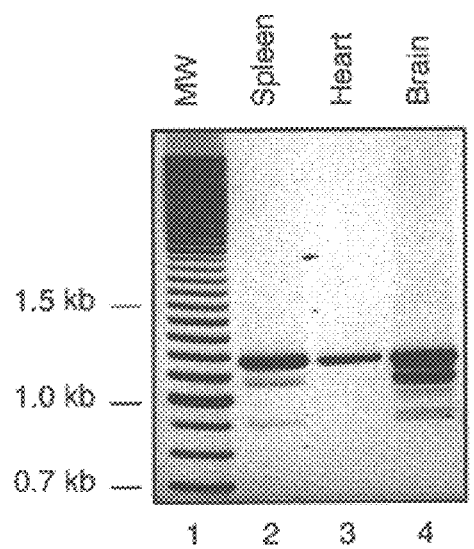
FIG._2
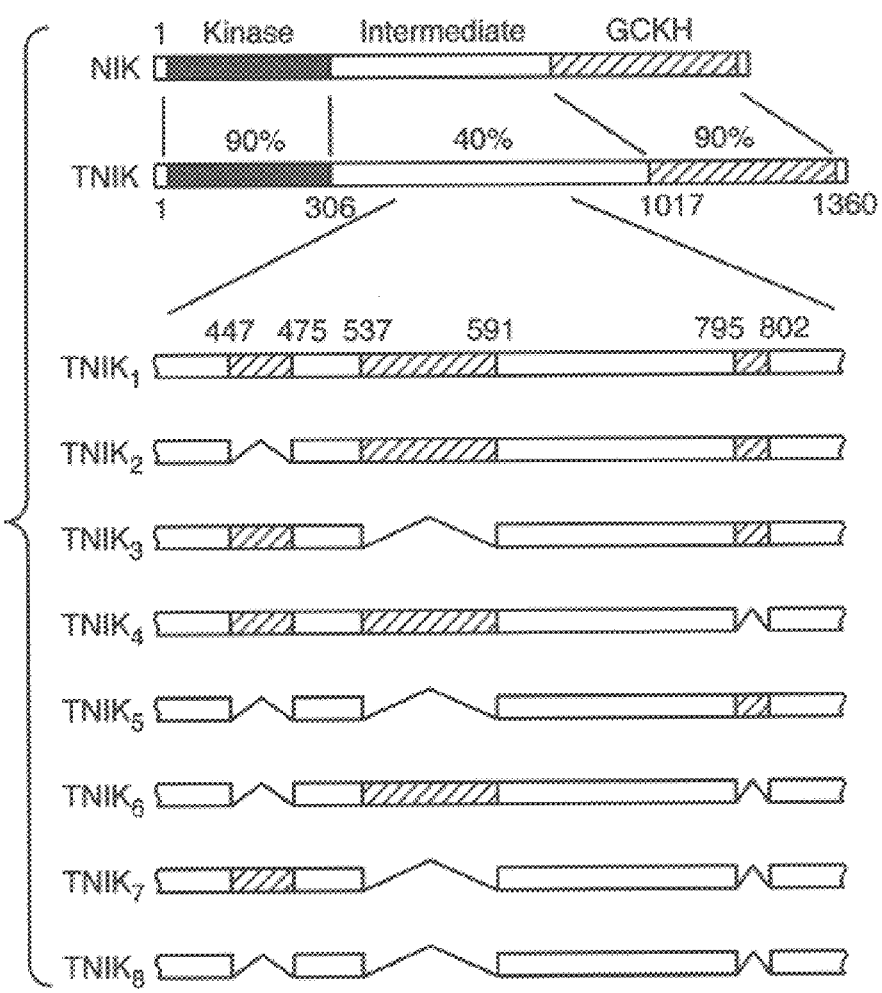
FIG._3

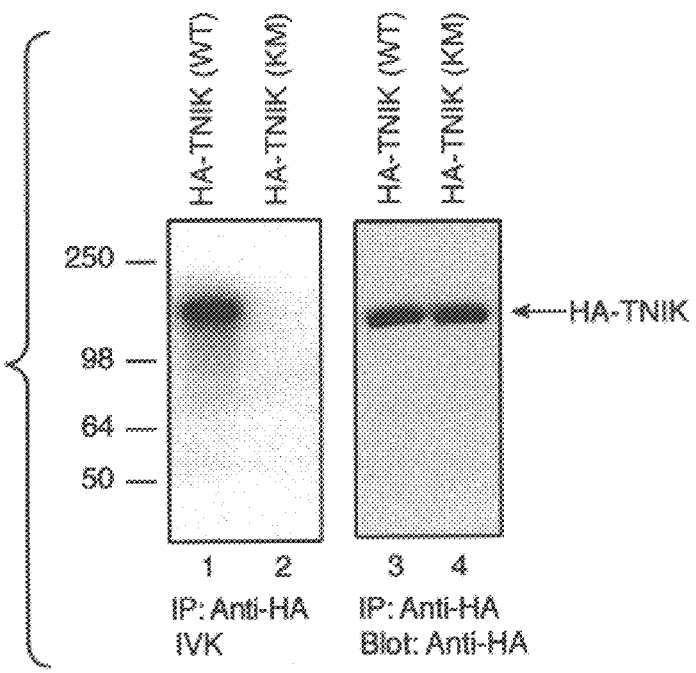
FIG._4
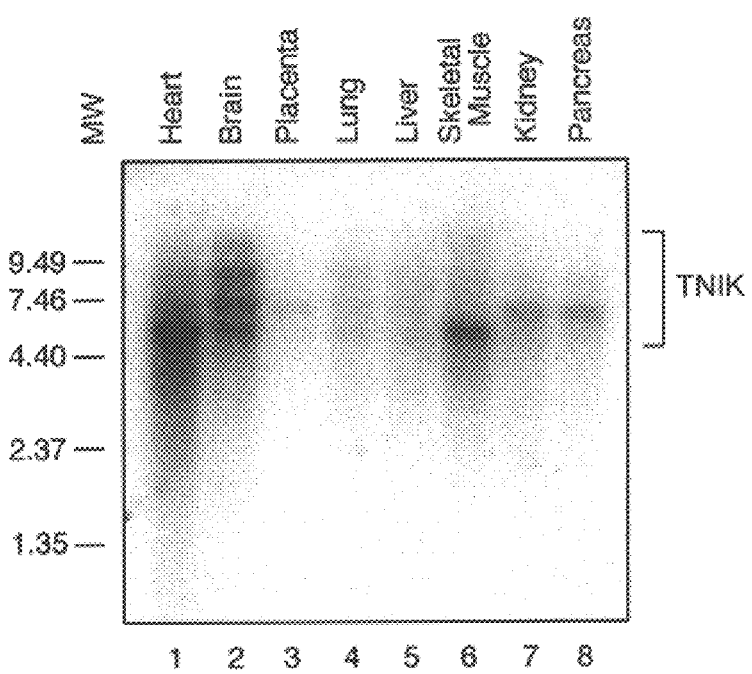
FIG._5A
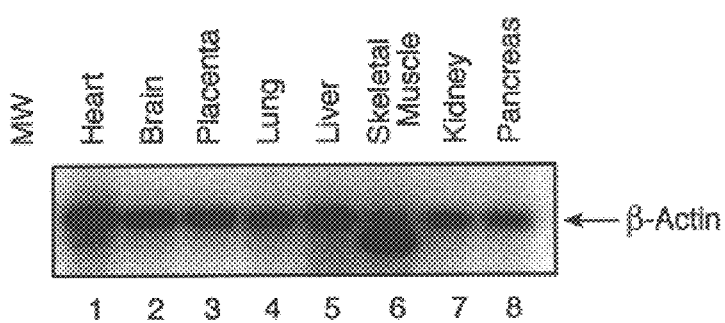
FIG._5B

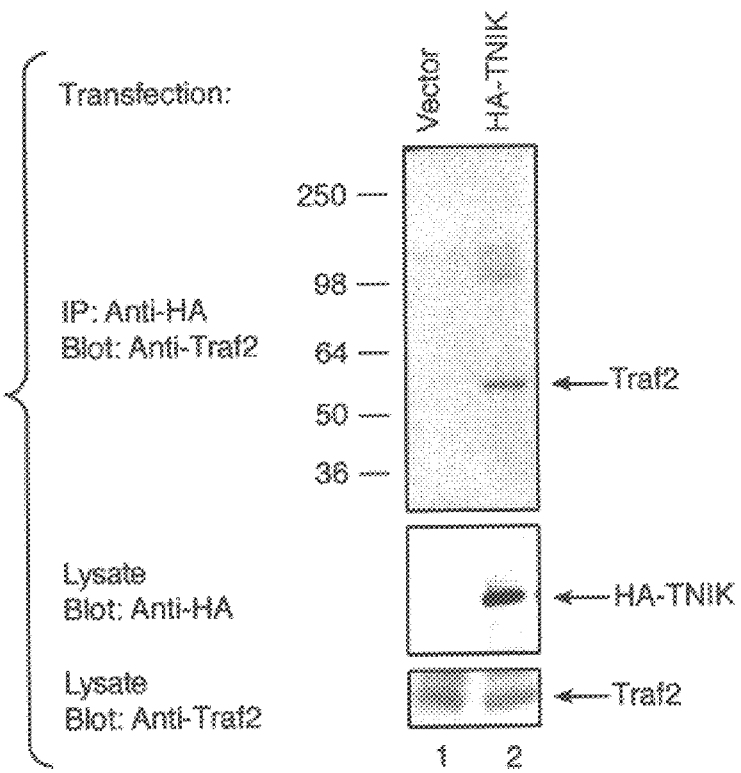
FIG._6
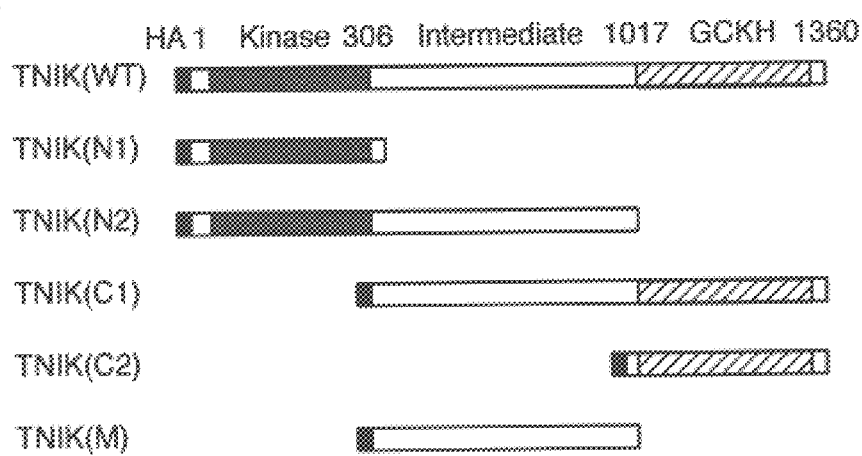
FIG._7

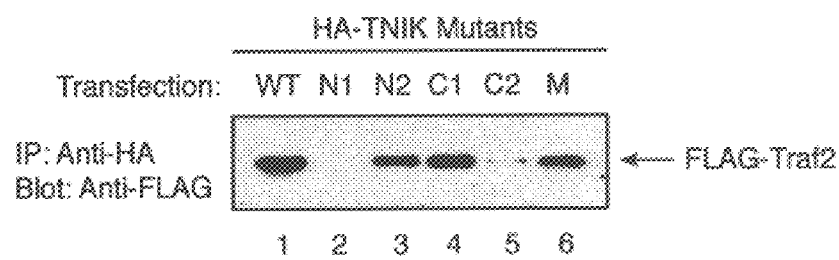
FIG._8A
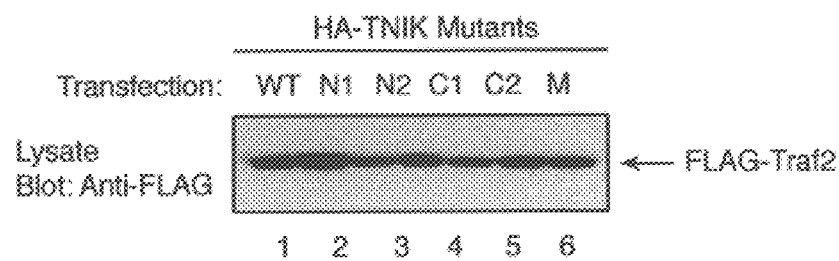
FIG._8B
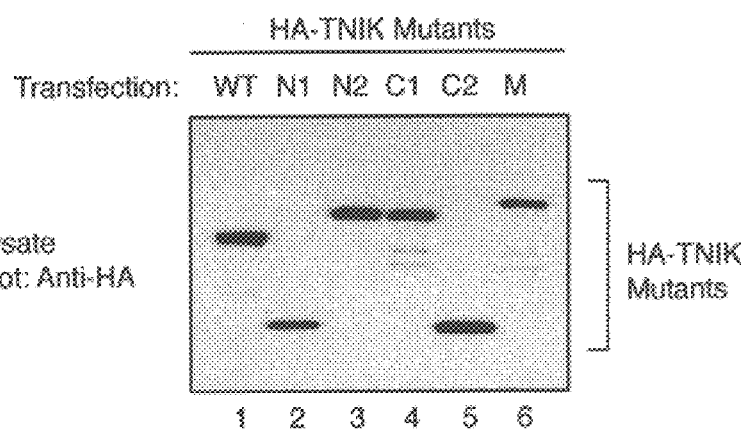
FIG._8C
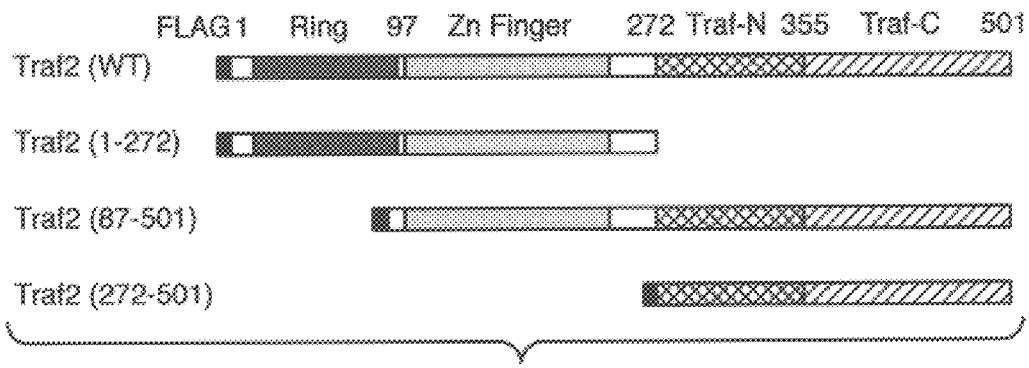
FIG._9

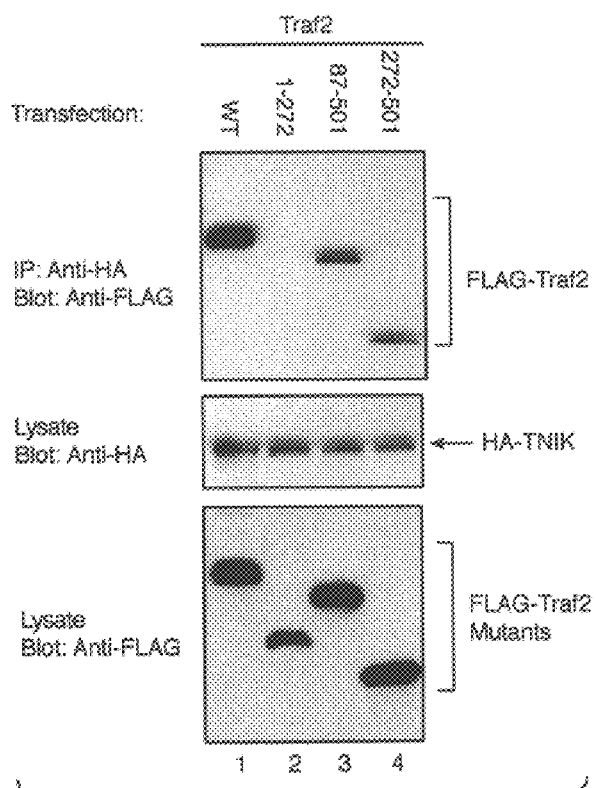
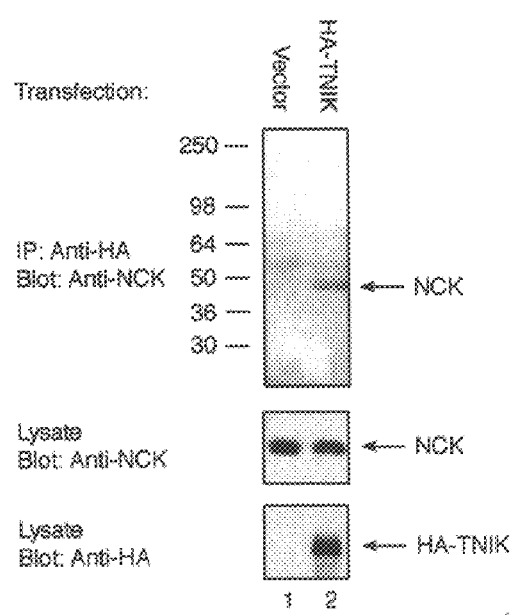
FIG._10
FIG._11

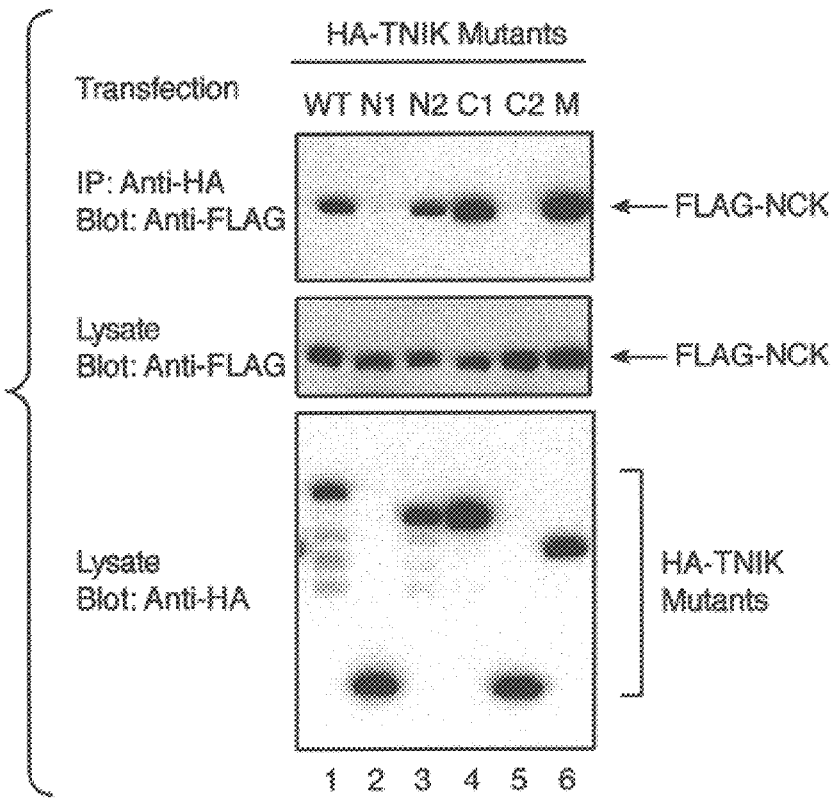
FIG._12
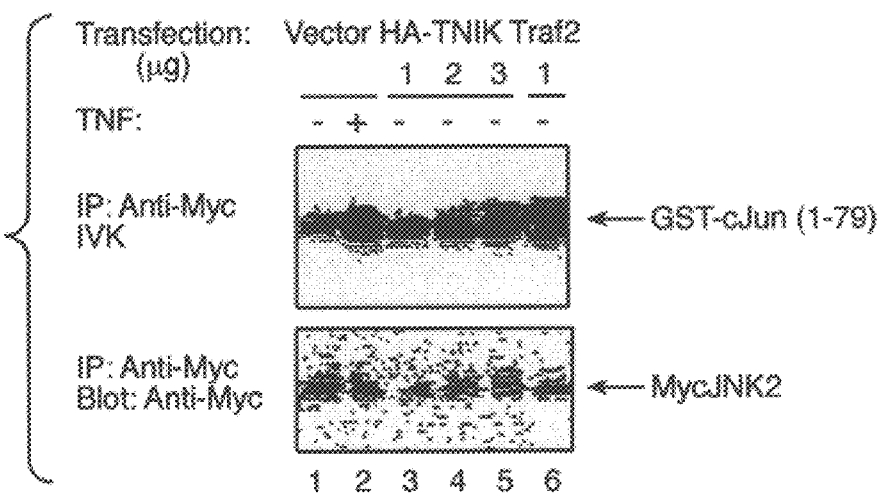
FIG._13

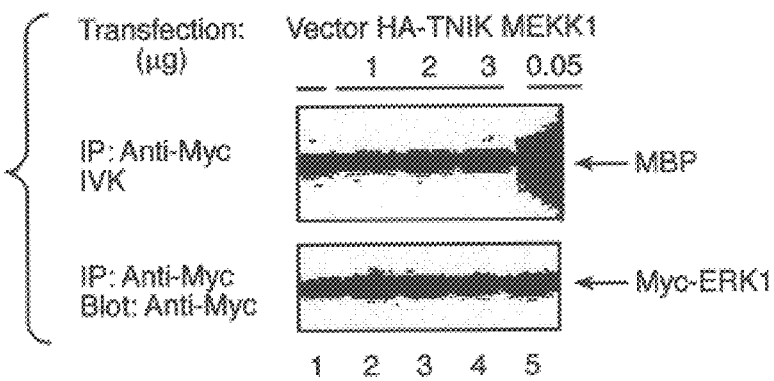
FIG._14
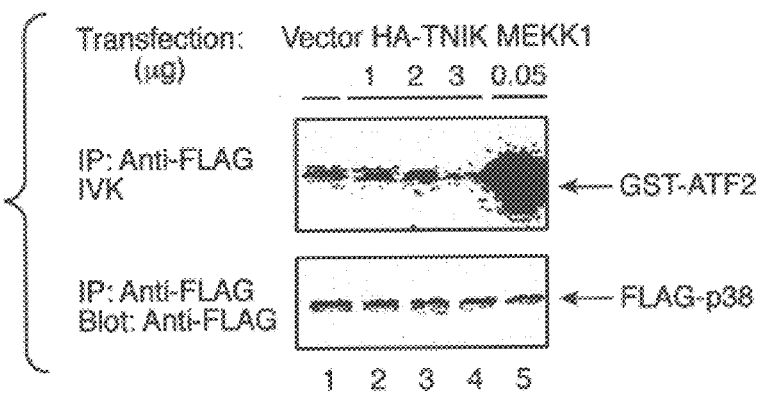
FIG._15
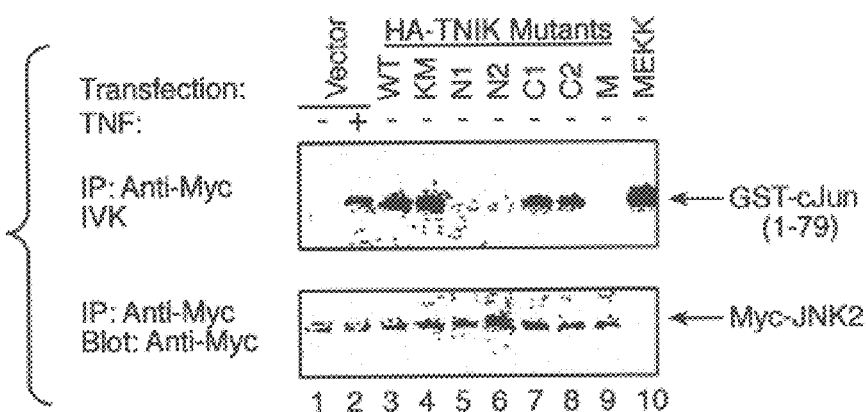
FIG._16

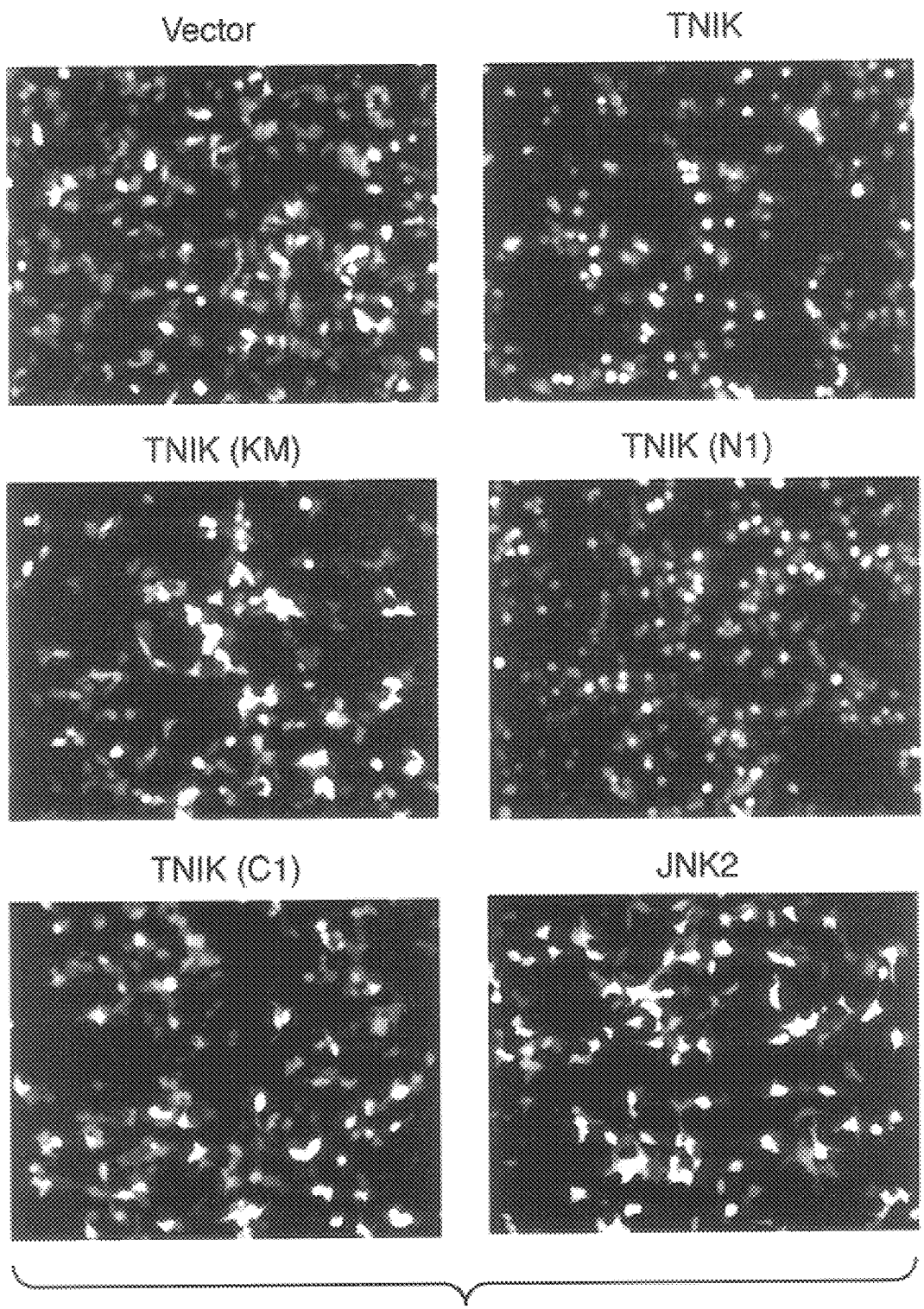
FIG._17

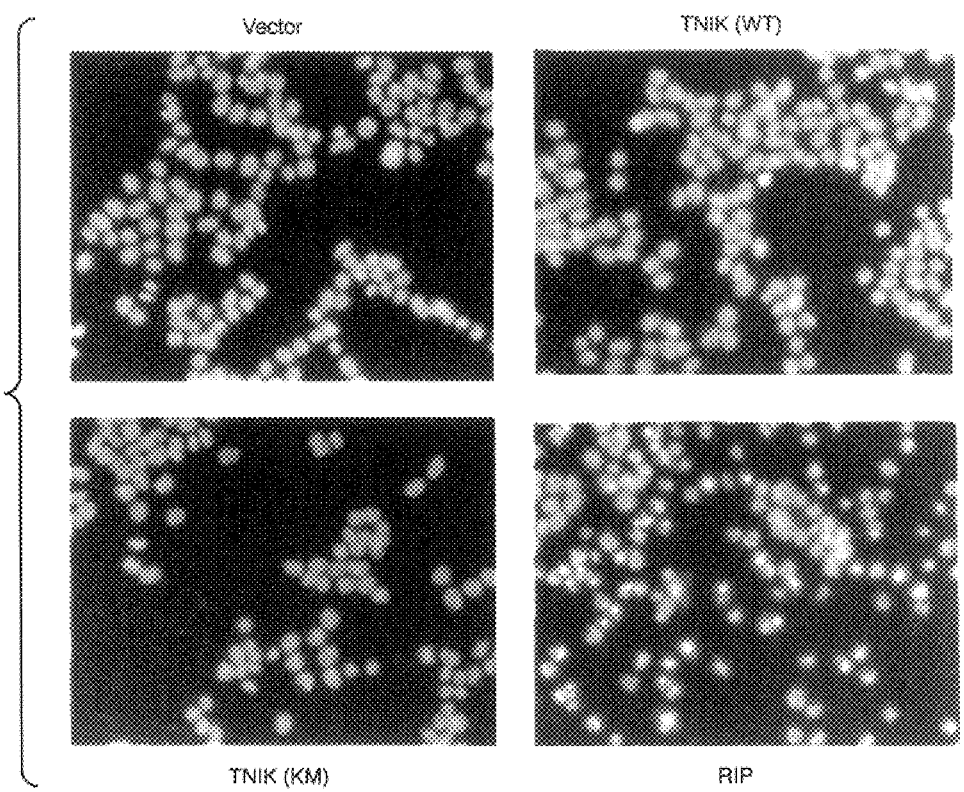
FIG._18

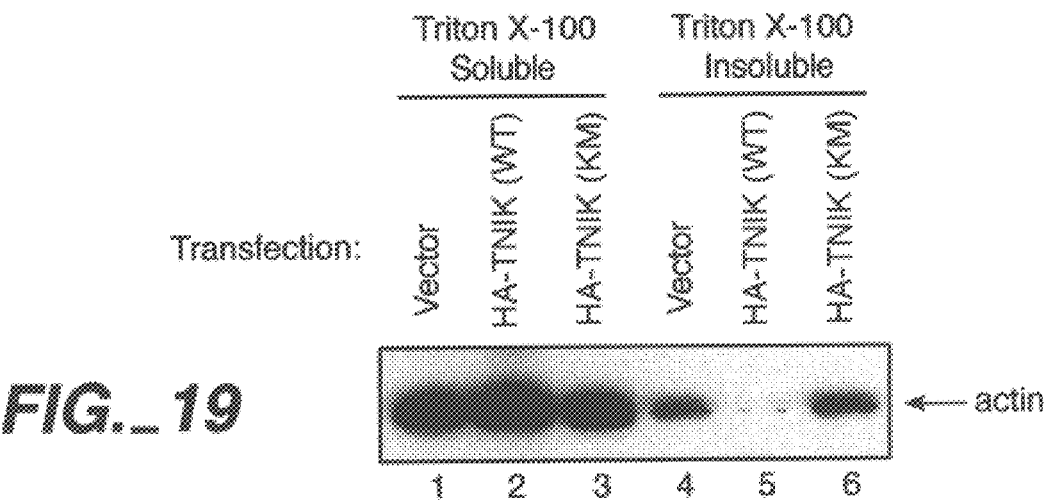
FIG._19
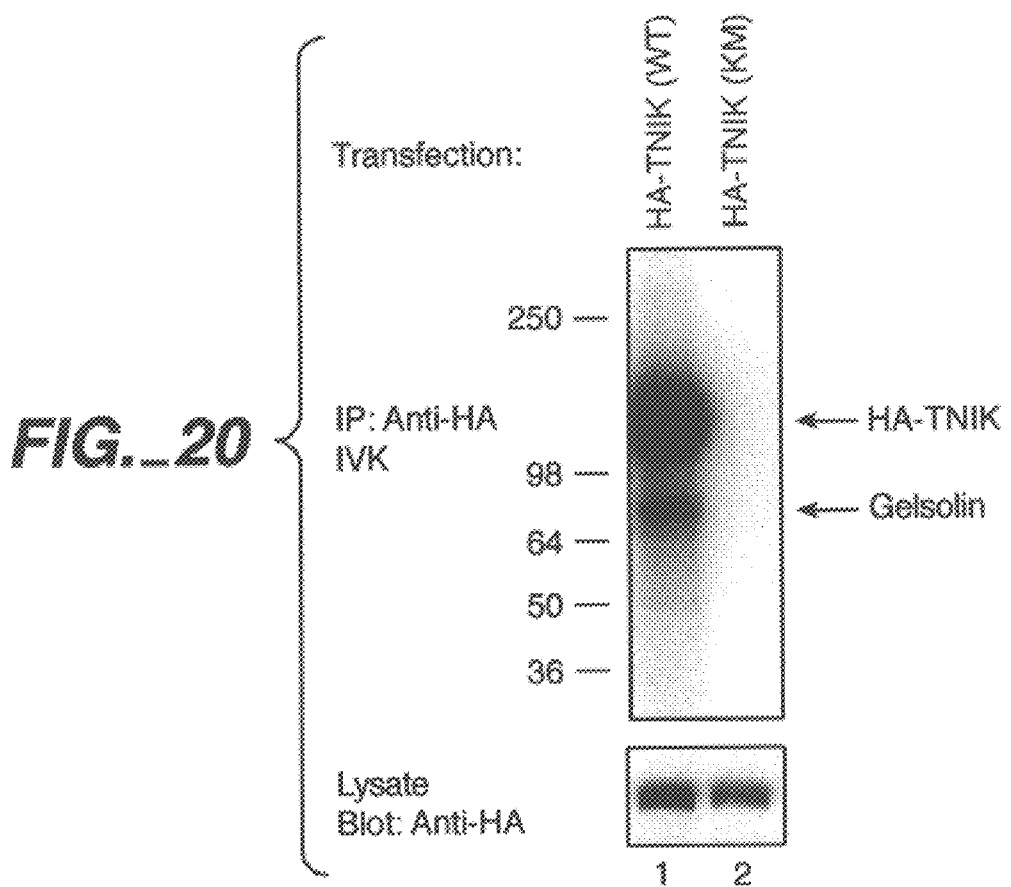
FIG._20

```
ATGGCGAGCGACTCCCCGGCTCTGAAGCCTCTGGATGAAATAGATCTCTCGGCTCTGAGGACCCTGCAGGATCTTT
GAATTGGTGGAACTTGTTGTTGAAATGGAACATACGGGCAAGTTTATAAGGTCGTCATGTCAAAACGGGCCAGCTT
GCAGCCATCAAGGTTATGATGTCACAGGGATGAAGAGGAAGAAATCAAACAAGAGAAATTAACATGTTGAAGAAA
TATTCTCATCACCGGAATATATTGCTACATACTATGGTGCTTTTATCAAAAGAACCCACCAGGCATGGATGACCAA
CTTTGGTTGGTGATGGAGTTTTGTGGTGCTGCTCTGTCACCGACCTGACCTCAAGAACACAAAGGTAACACGTTG
AAAGAGGAGTGGATTGCATACATCTGCAGGGAAATCTTACGGGGCTCAGGGAAATCTTACGGGGCTGAGTCACCCTGAGTCACCTGAGTCACTCACCCTGCAGCCAGCATAAAGTGATT
CATCGAGATATTAAAGGGCAAAATGTCTTGCTGACTGAAAATGCAGAAGTTAAACTAGTGACTTTGGAGTCAGT
GCTCAGCTTGATCGAACAGTGGGCAGGAGGAATACTTTCATTGGAACTCCCTACTGGATGGCACCAGAAGTTATT
GCCTGTGATGAAAACCCAGATGCCACACATATGATTTCAAGAGTGACTTGTGGTCTTTGGTATCACCGCCATTGAA
ATGGCAGAAGGTGCTCCCCCTCTGTGACATGCACCCCATGAGAGCTCTCATCCCCGAATCCAGCG
CCTCGGCTGAAGTCTAAGAAGTGGTCAAAAAAATTCCAGTCATTTATTGAGAGCTGCTTGGTAAAGAATCACAGC
CAGCGACCAGCAACAGAACAATTGATGAAGCATCCATTTATACGAGACCAACCTAATGACGACAGGTCCGCATT
CAACTCAAGGACCATATTGATAGAACAAAGAGAGAGAAAAGATGAGACAGATGACAGTCCGCATT
AGTGAGGAAGAAGAGGAGAATGACTCAGGAGAGCCCAGCTCCATCCTGAGGCCCTACGGAGCAGCAGTCGACGCTG
CGGAGGGACTTTCTGAGGCTGCAGCTGAGAATGAGAGCACAAGCGGCCAGCTGTGGCCGAGCGTCAGAAGCGCATC
CAGCAGCGGGGAGAATGAGAGCACAAGCGGCCAGCTGTGCGGAAGGAGCTGCGGAAGCAGCAGGAGCAGCGCCGG
CAGAGGCGGGCGGCCAGCAGATGCGCCGGGAGGAGCAACAGTTAGAGATCTTGCAGCAGCTACTGCATGAACAGCAG
CACTATGAGGAGCAGCAGAGACAGTTAGAGATCTTGCAGCAGCTACTGCATGAACAAGCTCTACTTCTGGAATAT
TTAGAGGAGGAGGACAAGCTCCAGAAGCTGAGGAGGAGGAGGAGCCTGTGAGAAGAACGGTTGAACGGTTGCCCCCCAAGTTCCCCCGGCC
AAGCGCAAACAATTGCAGCATCAGCGGCCAGGAGCGGCAGAGCCAGGAGAAGCCACTGTACCATTACAAAGAAGGAATG
GTTTCCCTTCAGCTGAGAAGCCATGGGCCAGGAGGTAGAAACGGTTGACCCCCAACCTGCCCCCAAGTCGAGTCCTTCAGCATTAGTGGA
AGTCCTAGTCACAAGGTTGCCAACACCCCCATGCTCAGATATCTGACCCCAACCTGCGATCCCCAGAGCAGCCACAAAGGCCTCTCTGGGTTTCAGGAGCT
ATGCCTCACAAGGTTGCCAACACCCCCATGCTCAGATATCTGACCCCAACCTGTGACGAGCAGCCACAAAGGCCTCTCTGGGTTTCAGGAGCT
GTTCAGCCTGCTCGAACATCTCAGAGCTGATCCCAGATCCCAGAGCAGCCACAAAGGCCTCTCTGGGTTTCAGGAGCT
CAGGGACCTGCCTTGACCCTCCCACGCGCTGTGGAGATGCCACGCCAGAACTCAGATCCCAGATCCAGAAAATCCTCTCCCC
CTGAACGTGACCCTGAAAGTTTGACCGAAGCTCTTGGTTACGACAGGAAGAAGACATTCCACCAAGGTGCCCTCAAAGA
```

*FIG._21A*

```
ACAACTTCTATATCCCCAGCATTAGCCAGAAAGAATTCTCCTGGGAATGGTAGTGCTCTGGGACTAGGA
TCTCAACCCATCAGAGCAAGCAACCCTGATCTCCGAGAACTGAGCCCATCTTGGAGAGCCCCTTGCAGAGGACC
AGCAGTGGCAGTTCCTCCAGCTCCCAGCACCCTAGCTCCCAGCCCCAGCTCCCAAGGAGGCTCCCAGCCTGATCA
CAAGCAGGATCCAGTGAACGCACCAGAGTTCGAGCAGCCAACAGTCAGAAGGATCACCTGTGCTTCCCATGAG
CCTGCCAAGGTGAAACCAGAAGAATCCAGGGACATTACCCGCCCAGTCGACCAGCTAGCTACAAAAAGCTATA
GATGAGGATCTGACGGCATTAGCCAGAAGAACTAAGGAGAAACTCCGATTGAAGAACAAACCGCCCAATGAAGAAG
GTGACTGATTACTCCTCCTCCAGTGAGGAGTCAGAAGTAGCGAGGAAGAAGTAGGAGGAAGATGGAGAGAGCGAGACC
CATGATGGGACAGTGGCTGTCAGCGACATACCCAGACTGATACCAACAGGAGCTCCAGGCAGCAACGAGCAGTAC
AATGTGGGAATGGTGGGGACGCATGGGCTGGAGACCTCTCATGCGGAGAGCAGTTTCAGCGGCAGTATTTCAAGAGAA
GGAACCTTGATGATTAGAGACGTCTGGAGCAGAGCGATCTGCCCACAGTGACACAGCAGTCGCTTTGCTGC
CACATCAACCTCCCTGACCTGGTGCAGCAGATGGACTCTGGGACTGAATATGGCCAAAGCCCGACTGGGGGCCGTC
TCAACCCATTCCAGCCCCCAGAGTATACCAGACGTCTCCCACTGAGTGAAGATGAAGAGGATGAAGAAGAGAAACGATTCGGTGGTAAATGTA
TTTGTGACCCCAGAGTATACCAGACGTCTCCCACTGAGTGAAGATGAAGAGGATGAAGAAGAGAAACGATTCGGTGGTAAATGTA
CTGTTTACTAGCGAACTTCTTAGGCAAGAACAGGCCAAACTCAATGAGAAAATCAGAATTCAACTCAGAAATA
AACCCAACCAACATTCGGCTCGTGTGGGTGTAAATCTGATCAACCAGAGTTTACTACGAGTTTCATGTTGAAGATTGCTGTGTGGACTGAATGTCTT
CTTTGTGCAGCTCTATAATCTGATCAACCAGGCTGATTTCAGCAGCCTGAAAATGCCTGATGTGCTAGAGGGACTGAATGTCTT
CAAGGCAAATTTCAGGAAGAAAGAAAGAAAGAAACAAGGCTGGATTTCAGCAGCCTGAAAATGCCTGATGTGCTAGAGGGACTGAATGTCTT
GTGACAATTTCAGGAAGAAAGAAAGAAAGAAACAAGGCTGGATTTCAGCAGCCTGAAAATGCCTGATGTGCTAGAGGGACTGAATGTCTT
GACCCAGAAGTAGAAAGAAAGAAACAAGGCTGGATTTCAGCAGCCTGAAAATGCCTGATGTGCTAGAGGGACTGAATGTCTT
AAATATGAAAGGATCAAATTTTGGTGATTGCCTTTTGCAGATCTCCAGCACACTGGTTTCCATGTAATTGATGTTCAGGAAACTCT
TATCATAAATTCATGGCATTTAAGTTCTTTGCAGATCTCCAGCACACTGGTTTCCATGTAATTGATGTTCAGGAAACTCT
GAAGGTCAAAGATTAAAGGTTATTTTGGTTATTTTTGGTTCACACACTGGTTTCCATGTAATTGATGTTCAGGAAACTCT
TATGATATCTACATACCATCTCATATTCAGGGCAATATCACTCCTCATGCTATTGTCATCTTGCCTAAACTAAGGATGTG
GGAATGGAAATGCTTGTTGCTATGAGGATGAGGGGTGTATGTAAACACCTATGCCGATAACTAAGGATGTG
GTGCTCCAATGGGGAGAAATGCCCACTGTCTGGCCTACATTGGATGGAGTATTTATGCATAAGCGAGCTAAAGGTTAAAG
GCTATTGAGATCCGGTTCAGTGGAAACAGAACAGAACAGAAGGTATTTTTGCATCCGTCGATCGGAGGAAGTAGCCAAGTGTTTTTCATG
TTTCTATGTGAAAGAAATGATAAGGTATTTTTGCATCCGTCGATCGGAGGAAGTAGCCAAGTGTTTTTCATG
ACCCTCAACAGAAATTCCATGATGAACTGGTAA
```

*FIG._21B*

ATGGCGAGCGACTCCCCGGCTCGAAGCCTGGATGAAATAGATCTCTCGGCTCTGAGGACCCTGCAGGATCTTT
GAATTGGTGGAACTTGTTGAAAATGAACATACGGGCAAGTTTATAAGGTCGTCATGTCAAAACGGGCCAGCTT
GCAGCCATCAAGGTTATGATGTCACAGGGATGAAGAGGAAGAAATCAAACAGAATTAACATGTTGAAGAAA
TATTCTCATCACCGGAATATTGCTACATATGGTGCTTTTATCAAAAAGAACCACCAGCATGATGACCAA
CTTTGGTTGGTGATGGAGTTTTGTGGTGCTGGCTGTCAGGGAAATCTTACGGGGCTGAGTCACCTGAGTTG
AAAGAGGAGTGGATTGCATACATCTGCAGGGAAATCTTGCTGACTGAAAATGCAGAAGTTAAACTAGTGGACTTTGGAGTCAGT
CATCGAGATATTAAAGGCAAAAGTGTGGGCAGGAGGAATACTTTCATTGAACTCCCTACTGATGCACCAGAAGTTATT
GCCTGTGATGAAAAACCCAGATGCCACATAGATTCAAGAGTGACTTGTGTCTTTGGTTATCACCGCCATTGAA
ATGGCAGAAGTCTGCTCCCCTCTCTGTGACATGCCAGTGAGCTCTTCCTCATCCCCGAATCCAGCG
CCTCGGCTGAAGTCAAGAGAAGAACAATTGATGAAGCATCCATTTATCGAGAGCTGCTTGGTAAAGAATCACAGC
CAGCGACCAGCAACAGAACAATATTGATAGAACAAAGAAGCGAGGAGAAAAGATGAGACAGAGTATGAGTACAGTGGA
CAACTCAAGGACCCATATTGATAGAACAAAGAAGCGAGGAGAAAAGATGAGACAGAGTATGAGTACAGTGGA
AGTGAGGAAGAAGAGGAGAATGACTCAGGCAGCCCCTCCAGCTGCCTACGGAGCCGTTCTGCCGAGCGTCAGAGCGGTCGGAGCAGCGAGAAAGAG
CGGAGGGACTTTCTGAGCTGGCCAACAAGACACAAGCGCAGCTGCTGCCGAGCGTCAGAGCGCATCGAGGAGCAGCGGCCGG
CAGCAGCGGGAGAATGAGGAGCACAAGCAACAAAGCGAGGAGAAGGCAGCAGCAGAACAGGAATATAAGCCAAACAA
CAGAGGCGGCGACAGATGCGCCGGGAGGAGGAGCAGCGTAAAGCCAGAGGAAGAAGAGACTACTTAGTTTCCTTCAG
CACTATGAGGAACAGAGACAAGCAGAGAGGCCTGTGAGAAGAACGGTCAAGCTAAAGCCAAGAAGAATGAGTCCTAGTGAG
AAGCCAGCATGGGCCAAGGAGGTAGACCCCAACCTGACCCAGAGTAGAGAATCTCAACCGGCAAAGTTCCCTGCCATGCCTCACAAG
GTTGCCAACACCCCCCATGCTCAGATCGACCAAGGCTCCTTGGAGTCTCCACATTAGTGAGTTCAGCCTGCT
CGAACACCCCCCATGCTCAGATCGACCAAGGCTCCTTGGAGTCTCCACATCTGGTAAAATCCCAGGACCCTGCC
TTGACCGCCTCCCAGTCAGTGCACGAGCAGCAACTCAGATCGAAATCCTCCTCCCACTCGCATTGAA
TCCCACCGCGTGGAGATGCCAAGTAGGAGAAGAGACATTCCACCAAAGTGCCTCAAAGAACAACTTCTATA
AAGTTTGACCAGCATTAGCCAGAAAGAATTCTCGGAATGGTAGTGCTCTGGGACCCAGATCTCAACCCATC
AGAGCAAGCAACCCCTGATCTCCGGAGAACTGAGCCCATCTTGAGAGCCCCTTGCAGAGACCAGCAGTGGCAGT

FIG._22A

```
TCCCCAGCATTAGCCAGAAAGAATTCTCCTGGGAATGGTAGTGTCTCTGGGACCCAGACTAGAGATCTCAACCCATC
AGAGCAAGCAACCCTGATCTCCGGAGAACTGAGCCCATCTTGGAGACCCCTTGCAGAGGACCAGCAGTGGCAGT
TCCTCCAGCTCCAGCACCCCTAGCTCCCAGCCTCCCAGGAGGCTCCCAGCCTGGATCACAAGCAGGATCC
AGTGAACGCACCAGAGTTCGAGCCAACAGTATACCCGGCCAACATTACCCGCCCAGTAGTCAGAAGGATCACCTGTCTTCCCATGAGCCTGCCAAGGTG
AAACCAGAAGAATCCAGGGACATTACCCGGCCAACATTACCCGCCCAGTAGCCAGCTAGCTACAAAAAGCTATAGATGAGGATCTG
ACGGCATTAGCCAAAGAACTAAGAGAACTCCGGATTGAAGAACAAACCGCCAATGAAGAAGGTGACTGATTAC
TCCTCCTCCAGTGAGGAGTCAGAAAGTAGCGAGGAAGAGGAGGAAGATGGAGAGACCCATGATGGGACA
GTGGCTGTCAGCGACATACCCAGAGCTCTCAGGAGAGCTCCAGCGACAGCAGTAGCAGTACAATGTGGAATG
GTGGGGACGCATGGCTGGAGAACCCTCTCATGCGGAGACCCTCTCATGCGGACAGTTTCAGCGGCAGTATTCAAGAGAAGGAACCTTGATG
ATTAGAGAGACGTCTGGAGCAGCAGAGCCATTCTCCAGTCGAACCCCGACTGGAGCTGCCACAGTGACAGCAATGGCTTTGCTGCCACATCAACCTC
CCTGACCTGGTGTGCAGCAGAGCCATTCTCCAGTCGAACCCCGACTGGAGCAGCAGCCAAAGCCTCTCACCCCCTTGTGACCCC
CAGGAGATGGACTCTGGACTGAATATGGCATGGGAGCAGCAGAAGGATGAAGAGGAATCATCAGCCGCAGCTCTGTTACTAGC
AGAGTATACCAGACGTCTCCCACTGATGAAGATGAAGAGGAATCAATGAAGCAAGAAAGATTTCGGTGGTAATGTAAACCAACCAAC
GAACTTCTTAGGCAAGAACAGCCAAACTCAATGAAGCAAGAAAGATTTCGGTGGTAATGTAAACCAACCAAC
ATTCGGCCTCATAGCGACACACCAGAAATCAGAAAACGATTCAACTCAGAGAAACTACTTTGTGCAGCT
CTGTGGGGTGTAAACTCAACCGGAGGCGATTTCAGCAGGACTGATGTGCTAGAGGGACTGAATGTCCTTGTGACAAGTC
TATAATCTGATCAACCGGAGGCGATTTCAGCAGGACTGATGTGCTAGAGAGAACAGAATACTACATAAGTTGTTAAATATGAAAGG
GAAAGAAGAATAAGCTACGAGTTTACTACTATCTTTCATGTTGGGACTTGGAAGCTGTATACATTATAAGTTGTTAAATATGAAAGG
GAAAAGAAACAAGGCTGGATCACTGTTGGGACTTGGAAGCTGTATACATTATAAGTTGTTAAATATGAAAGG
ATCAAATTTGGTGATTGCCTTAAAGAATGCTGTGGAAATGCTCTGGCTCCTAAACCGTATCATAATTC
ATGGCATTAAGTCTTTGCAGATCTTTGCAGATCTCTTGATCTCTTGATCTCTTGATCTCTTGATCTCTTGATCTCTTGATCTATATCTAC
TTAAAGGTTATTTTTGGTTCACACACTGGTTTCCATGGTTTCAGGAAACAGGAAACTCTTATGATATCTAC
ATACCATCTCATATTCAGGCAATATTCAGGGCAATATTCACACTGGTAACCATGGTAACCAGATAACAGATGGAATGG
CTTGTTTGCTATGAGGATGAGGGTGTATGTAAACACCTAGGATGTGGTGCTCCAATGG
GGAGAAATGCCCACGTCTGTGCCTACACTTCAATCATTCCAATCAGATAATGGCGGGGAGAAAGCTATTGAGATC
CGGTCAGTGGAAACAGGACATTGGATGGAGTATTTATGCATAAGCGAGCTCAAAGTTAAGTTTCTATGTGAA
AGAAATGATAAGGTATTTTTTGCATCCGTGCGATCTGGAGGAAGTAGCCAAGTGTTTTTCATGACCCTCAACAGA
AATTCCATGATGAACTGGTAA
```

TCCAGCTCCAGCACCCCTAGCTCCCAAGGAGCTCCAGCCTGATCACAAGCAGATCCAGT
GAACGCACCAGAGTTCGAGCCAACAGTAAGTCAGAAGGATCACCTGTCTTCCCATGAGCCTGCCAAGTGAAA
CCAGAAGAATCCAGGGACATTACCCGGCCCAGTCGACCAGCTAGCTACAAAAAGCTATAGAGGATCTGACG
GCATTAGCCAAAGAACTAAGAGAACTCCGGATTGAAGAGAAGAAGTGACTGATTACTCC
TCCTCCAGTGAGGAGTCAGAAGTAGCGAGGAAGAGGAGAACCAGGAGAGCTCCAGCAGTACAATGTGGGACAGTG
GCTGTCAGCGACATACCCAGAGACCCTCATGCGGACAGTTTCAGCGGCAGTATTCAAGAGAAGGAACCTTGATGATT
GGGACGCATGGGCTGGAGACCTCTGGAGACTGGGCGATCTGGCCACAGTCTGCCACATCAACCTCCT
AGAGAGAACGTCTGGAGCAGCCATTCTCCCAGTGAACCCCGACTGGGGCGTCTCAACCCATTCCCAG
GACCTGGTGCAGCAGCCATTCTGGGACTGAATATGGCATGGGGAGCAGCACCAAAGCCCTCTTCACCCCCTTTGTGACCCCAGA
GAGATGGACTCTGGGACTGAATATGGCATGAGATGAAGAGATGAAGAGAAGATTTCGGTGGTAAATGTAAACCAACCAACATT
GTATACCAGACGTCTCCCACTGATGAAGAATCAATGAGACCCAAACTCAGAAAATACAAGAACGATTCAACTCAGAAGAATACTTTGTGCAGCTCTG
CTTCTTAGGCAAGAACAGGCCAAACTCAGAAATCAGAAAATACAAGAACGATTCAACTCAGAAATACTTTGTGCAGCTCTG
CGGCCCTCATAGCGACACACCAGAGAATCAGAAATCAGAAATACAAGAACGATTCAACTCAGAAATACTTTGTGCAGCTCTG
TGGGGTGTAAACCTTCTGGTGGGACGATTCAGCAGGCGATTGTGCTAGAGGACTGAATGTCCTTGTGACAATTTCAGGA
AATCTGATCAACCGGAGGCGATTCAGCAGGCTACGAGTTTACTACTATCTTTCATGGTTAAGAACACAGAATACATAATGACCCAGAAGTAGAA
AAGAAGAATAAGCTACGAGTTCACTGTTGGGGACTGTTGGAAGGCTGTATACATTATAAGTTGTTAAATATGAAAGGATC
AAGAAACAAGGCTGGATCACTGTTGGGGACTGTTGGAAGGCTGTATACATTATAAGTTGTTAAATATGAAAGGATC
AAATTTTGGTGATTGCCTTAAAGAGATCTCTTTGCAGATTCTTTGCAGATCCTCTGCTAGTTGATCTCACGGTAGAAGAGGTCAAAGATTA
GCATTTAAGTCTTTTGCAGATCTCTTTGCAGATCCTCTGCTAGTTGATCTCACGGTAGAAGAGGTCAAAGATTA
AAGGTTATTTTTTGGTTCACACACTGGTTTCCATGTTTCCATGTCATGCTATTGATTCAGGAAAAACTCTTATGATATCTACATA
CCATCTCATATTCAGGCAATATCACTCCTATTGTCATCTTGCCTAAAACAGATGAATGGAAATGCTT
GTTTGCTATGAGGATGAGGGGGTGTATGTAAACACCTATGCCGGATAACCTATGCCGGATAACCTATGTGTGGTGCTGCTCCAATGGGGA
GAAATGCCCACGTCTGTGGCCTACATTCATTCCAATCAGATAATGGCTGGGGCGAGAAAGCTATTGAGATCCGG
TCAGTGGAAACAGGACATTTGGATGGAGTATTTATGCATAAGCGAGCTCAAAGGTTAAAGTTTCTATGTGAAAGA
AATGATAAGGTATTTTTTCATCCGTGCGATCTGGAGGAAGTAGCCAAGTGTTTTTCATGACCCTCAACAGAAAT
TCCATGATGAACTGGTAA

*FIG._23B*

```
ATGGCGAGCGACTCCCCGGCTCTCGAAGCCTCTGGATGAAATAGATCTCTCGGCTCTGCAGGTCTGCAGGATCTTT
GAATTGGTGGAACTTGTTGTTGAACTTGTTGGAAATGGAACATACGGGCAAGTTTATAAGGGTCGTCATGTCAAAACGGGCCAGCTT
GCAGCCATCAAGGTTATGGATGTCACAGGGATGAAGAGGAAGAAATCAAACAGAAATTAACACATGTTGAAGAAA
TATTCTCATCACCGGAATATTGCTACATATGGTGCTTTTATCAAAAGAACCCACCAGGCATGGATGACCAA
CTTTGGTTGGTGATGAGTTTGTGGTCTGTGCTGGCTCTGTCACCGACCTGATCAAGAACAACAAAGGTAACACGTTG
AAAGAGGAGTGGATTGCATACATCTGCAGGGAAATCTTACGGGGCTGAGTCACCTGCACCAGCATAAAGTGATT
CATCGAGATATTAAAGGCAAATGTCTTGCTGACTGAAAATGCAGAAGTTAAACTAGTGGACTTTGGAGTCAGT
GCTCAGCTTGATCGAACAGTGGGCAGGAGAATACTTTCATTGGAACTCCCTACTGGATGGCACCAGAAGTTATT
GCCTGTGATGAAACCCAGATGCCACATATGATTTCAAGAGTGACTTGTGTCTTTGGGTATCACCCCGAATCGAA
ATGGCAGAAGGTGCTCCCCCTCTGTGACATGCACCCATGAGAGCTCTTCCTCATCCCCGAATCCAGCG
CCTCGGCTGAAGTCTAAGAAGTGGTCAAAAAAATTCCAGTCATTTATTGAGAGCTGCTTGGTAAAGAATCACAGC
CAGCGACCAGCAACAGCATCCATTTATACGAGACCAACCTAATGAGCGACAGGTCCGCATT
CAACTCAAGGACCATATTGATAGAACAAGAAGAGAAAAGATGAGACAGAGTATGAGTACAGTGGA
AGTGAGGAAGAGAGGAGGAGAATGACTCAGGAGAGCCCAGCTCCATCCTGAATCTCGCCAGGGAGTCGACGCTG
CGGAGGGACTTTCTGAGGCTGCAGCTGTGGCCAACAAGGAGCGTTCTGAGCCCTGAGCGGTCAGGAGCCAGCAGCTGGAGCAG
CAGAGGCGGCGGCTGGAGAATGAGGAGCACAAGCGGCAGCAACAAAGCGAGAGAAGCAGGAGAGGAGCAGCAG
CACTATGAGGAGCAGATGCGCGGGAGGAGCAGTTAGAGACAGAGATCTTGCAGCAGAAAGACTGCAGAGGCAGTGAACAGGGAATACATCAGGCGACAG
TTAGAGGAGGAGCAGCAGAATTGAAGAACAGAGAACAAGAGAACAGAGACCACTGAGCAGAAAAGCCTAAAGCAAGAAGAGACTACTTA
AAGCGCAAACAATTGAGAAGCATCAGCGGCCAGGATATCTGACCCCCAACCTGACCCCCAAGTTCCCCTGCC
GTTCCTTCGTGTGAGAAGCCAGCATGGGCCAGGATATCTGACCCCCAACCTGACCCCCAAGTCGGAGTCCTTCAGCATTAGTGGA
AGTCCTACACAAGGTTGCCAACACCCCAGCCCTCGAATCTCAGACCAGTCGACGAGCAGCGAGCCTCCCAGATCCCAGAAATCC
ATGCCCAAGGTGCTCGAACACCCCAGCCCTCGAATCTCAGAGCTGCACGAGCAGCCAGCCTCCCAGATCCCACACAAAGGCCCTCCACCTGTGGAGCT
CAGGACCTGCCCTTGACCGCCTGCCTTGACCGCCTGCCAGTGCACGAGATGCCACACAAGGCCCTCCACCTGTGGAGCT
CTGAACGTGACCTGCATTGAAAAGTTGACCGAAGCTCTTGGTTACGACAGGAAGACATTCCACCAAGGTGCCTCAAGA
ACAACTTCTATATCCCCAGCCATTAGCCAGAAAGAATTCTCCTGGAATGGTAGTGCTCTGGGACCCAGACTAGGA
```

FIG._24A

```
TCTCAACCCATCAGAGCAAGCAACCCTGATCTCCGGAGAGAACTGAGCCCATCTTGCAGAGACC
AGCAGTGGCAGTTCCTCCAGCTCCCAGCACCCTAGCTCCCAAGGAGGCTCCCAGCCTGGATCA
CAAGCAGGATCCAGTGAACGCACCAGAGTTCGAGCCAACAGTCAGAAGGATCACCTGTCTTCCCCATGAG
CCTGCCAAGGTGAAACCAGAAGAATCCAGGGACATTACCCGCCCAGTCGACCAGCTGATCTGACGGCATTAGCC
AAAGAACTAAGAGAGAACTCCGGATTGAAGAAACAAACCGCCCCATGAAGAAGGTGACTGATTACTCCTCCAGT
GAGGAGTCAGAAAGTAGCGAGGAAGAGGAGAGAGCTCCAGGCAGAGAGCGAGACCCATGATGGACAGTGGCTGTCAGC
GACATACCCAGACTGATACCAACAGGAGCTCCAGGCAGCAGTACAATGTGGGAATGGTGGGGACGCAT
GGGCTGGAGACCCTCTCATGCGGACAGTTTCAGCGGCACAGCAATGGCTTTGTGCGCCACATCAACCTCCCTGACCTGTG
CAGCAGAGCCATTCTCCAGCTGGCCACAGTCGACAGCAATGGCTTTGTGCGGCGCGTCTCAACCCATTCCCAGGAGATGGAC
TCTGGGACTGAATATGGCATGGGAGCAGCAGCAAAGCCTCCTTCACCCCCTTTGTGGACCCCAGAGTATACCAG
ACGTCTCCCACTGATGAAGAGATGAAGAAGAGGAATCATCAGCCGCAGCTCTGTTTACTAGCGAACTTCTTAGG
CAAGAACAGGCCAAACTCAGAGAAATCAAGAAGAAGATTTCGGTGGTAAATGTAACCCAACATTCGGCCTCAT
AGCGACACACCAGAGAAATCAGAAGAACAGATTCAACTCAGAGAAATACTTTGTGCAGCTCTGTGGGGTGTA
AACCTTCTGTGGGGACTGAAGCAGATGGAATGGCCTGATGCTTTTTGGACCCAAGTCTATAATCTGATC
AACCGGAGGCGATTTCAGCAGATGGAGTGCTAGAGGGACTGAATGTCCTTGTGACAATTTCAGGAAAGAAGAAT
AAGCTACGAGTTTACTACTATCTTTCATGGTTAAGAAACAGAATACTACCATAATGACCCAGAAGTAGAAAAGAAACAA
GGCTGGATCACTGTTGGGGACTTGGAAGCTGTATACATTAAGGATCAAAATTTTTG
GTGATTGCCTTAAAGAATGCTGTGTGGAAATATGCTTGGGCTCCTAAACCGTATCATAATTCATGGCATTAAG
TCTTTTGCAGATCTCCAGCACCAAGCCTCTCGCTAGTTGATCTCACGGTAGAAGAAGGTCAAAGATTAAAGGTTATT
TTTGGTTCACACACTGGTTTCCATGTCCATGCTATTGTTCATCTTGCCTAAAACAGATGGAAATGCTTGTTTGCTAT
ATTCAGGGCAATATCACTCCTATTGTAAACACCTATGCCGATAACCATCAGATAATGGGCTGCTCCAATGGGGAGAAATGCCC
GAGGATGAGGGGTATGTAAACACCTATGCCGATAATCAGATAATGGGCTGCTCCAATGGGGAGAAATGCCC
ACGTCTGTGGCCTTCATTCATTCCAATCAGATAATGGGGCGAGTCAAAGGTTAAGTTTCTATGTGAAAGAAATGATAAG
ACAGGACATTTGATGGAGTATTTATGCATAAGCGAGTCAAAGGTTAAGTTTCTATGTGAAAGAAATGATAAG
GTATTTTTTGCATCCGTGCGATCTGGAGGAAGTAGCCAAGTGTTTTCATGACCCTCAACAGAAATTCCATGATG
AACTGGTAA
```

FIG. 24B

```
ATGGCGAGCGACTCCCCGGCTCTCGAAGCCTGAGCCTGGATGAAATAGATCTCTCGGCTCTCGAGGACCCTGCAGGGATCTTT
GAATTGGTGGAACTTGTGTGAAATGGAAACATACGGCAAGTTTATAAGGTCGTCATGTCAAAACAGGGCCAGCTT
GCAGCCATCAAGGTTATGGATGTCACAGGGGATGAAGAGGAAGAAATCAAACAAGAAATTAACATGTTGAAGAAA
TATTCTCATCACCGGAATATTGCTACATACTATGGTGCTCTGTCAGGGAAATCTTACCCCAGGCATGGATGACCAA
CTTTGGTTGGTGATGGAGTTTTGTGGTGCTGGCTCTGGCAGGAAATCTTACCGGGGCTGAGTCACCTGCAGTGACT
AAAGAGGAGTGGATTGCATACATCTGCAGGAAATGTCTTGCTGACTGAAAATGCAGAAGTTAAACTAGTGACTTTGGAGTCAGT
CATCGAGATATTAAAGGGCAAAATGTCTTGCTGACTGAAAATGCAGAAGTTAAACTAGTGACTTTGGAGTCAGT
GCTCAGCTTGATGAACAGTGGGCAGGAGGAATACTTTCAAGAACTTCCCTACTGATGGCACCAGAAGTTATT
GCCTGTGATGAAAACCCAGATGCCACACATATGATTTCAAGAGTGACTTGTGTTCTTCCTCATCCCGAATCCAGCG
ATGGCAGAAGGTGCTCCCCTCTGTGACATGCACCCCATGAGAGCTCTCATTATTGAGAGTCGTTGGTAAAGAATCACAGC
CCTCGGCTGAAGTCTAAGAAGTGGTCAAAAAAATTCCAGTCATTTATGAGAGTCGTTGGTAAAGAATCACAGC
CAGCGACCAGCAACAGAACAATTGATGAACATCCATTTATACGAGACCAACTAATGAGCGACAGGTCCGCATT
CAACTCAAGGACCATATATTGATAGAACAAAAGATGAGAGAAAGATGAGACAGAGTATGAGTACAGTGGA
AGTGAGGAAGAAGAGGAGAATGACTCAGGAGCCCAGCTCCATCCTGAATCTGCCAGGGAGTCGACGCTG
CGGAGGGACTTTCTGAGGCTGCGAGCTGGCCAACAAGGAGCGTCTGGCCGAGCGTCAGAAGCGCATCGAGGAGCAGCAGCAG
CAGCAGCGGGCGGCTGGAGGAGCAACAAGCGGCACAACAAAGGCAGCAGGAAGGAGCTGCGGAAGCAGCAGGAGGAGCAGCGCGG
CAGAGGCGGCGGCTGGAGGAGCAGAAGCAGAGGCCGCGGGAGGAGCAGCAGGAAGCAGCAGGAATATAAGCGCAAACAA
CACTATGAGAACAGAGACAAGCAGAGACAGAGAGGCCTGTGGAGAAGAACTGCAGAGGCAGCAGCTAAAGCAAGACTACTTAGTTTCCCTTCAG
TTGGAAGAACAGAGACAAGCAGAGACAGAGAGGCCTGTGGAGAAGAACTGTACAAGAAAGAGACTACTTAGTTTCCCTTCAG
CATCAGCGCAGGAGCAGGAGCAAGAGCCCACATCTGGTAGCTGTAAAATCCCAGGAGCCTGCCTTGACCGTGAGCCTCCAG
AAGCCAGCATGGCCAGCAGCCAGAACTCAGATCCCACACAAAGGCCTCTCACCTCGGAATCCGCCTCCACCCGCGTGGAG
TCAGTGCACGCCAGAACTCGACAGGAAGAACATTCCACCAAAGTGCCTCAAAGAACAACTCTATATCCCAGCAAGCAACCCT
ATGCCACGCCAGAACTCGACAGGAAGAACATTCCACCAAAGTGCCTCAAAGAACAACTCTATATCCCAGCAAGCAACCCT
TCTTGGTTACGACAGGAAGAACATTCCACCAAAGTGCCTCAAAGAACAACTCTATATCCCAGCAAGCAACCCT
AGAAAGAATTCTCCGGGAACTGAGCCCATCTTGGAGAGCCCTTGCAGAGGACCCAGTGGCAGTTCCTCCAGCTCCAGC
GATCTCCGAGAACTGAGCCCATCTTGGAGAGCCCTTGCAGAGGACCCAGTGGCAGTTCCTCCAGCTCCAGC
ACCCCTAGCTCCCAGCCTCCCCAGCTCCCCCCAAGGAGGCTCCCCAAGGAGCTCCCAAGGAGGTCCCAGCTCCAGC
```

FIG._25A

GTTCGAGCCAACAGTAAGTCAGAAGGATCACCTGTGCTTCCCCATGAGCCTGCCAAGGTGAAACCAGAAGAATCC
AGGGACATTACCCGGCCCAGTCGACCAGTCGATTGAAGAAAAAGCTATAGATGAGGATCTGACGGCATTAGCCAAA
GAACTAAGAGAACTCCGGATTGAAGAAACAAACCGCCCAATGAAGAAGGTGACTGATTACTCCTCCAGTGAG
GAGTCAGAAGTAGCGAGGAAGATGGAGAGAGCGAGACCAGTACAATGTGGGAATGGTGGGACGATGGCAGCGAC
ATACCCAGACTGATACCATGCGGGACAGTTTCAGCGGCAGTATTTCAAGAGAAGGAACCTTGATGATTAGAGAGACGTCT
CTGGAGACCTCTCATGCGGGACAGTTTCAGCGGCAGTATTTCAAGAGAAGGAACCTTGATGATTAGAGAGACGTCT
GAGAGAGAAAGCGATCTGGCCAGTGACATCTGGCCACAGCCCGACTGGAACCTGCTCAACCTCCCTGACCTGTGCAG
CAGAGCCATTCTCCAGCTGGAAACCCGACTGGGGCGCTCAACAGCCCTCCTTGTGACCCCAGAGTATACCAGACG
GGGACTGAATATGGCATGGGACTGAGGATGGCAGCACCAAAAGCCTCCTTGTGACCCCAGAGTATACCAGACG
TCTCCCACTGATGAAGATGAAGAGAACAAGAGATTTCGGTGGTAAATGTAAACCAACATTCGGCCTCATAGC
GAACAGGCCAAACTCAATGAGAAATCAGAAATACAAGAGATTCAACTCAGAAATACTTTGTGCAGCTGCTCTGTGGGGTGTAAAC
GACACACCAGAAATCAGAAATCAGAAATACAAGAGATTCAACTCAGAAATACTTTGTGCAGCTGCTCTGTGGGGTGTAAAC
CTTCTGGTGGGGACTGAAAATGGCCTGATGCTTTTGGACCGAAGTGCTTGTGACCAAAGTCTATAATCTGATCAAC
CGGAGGCGATTTCAGCAGATGTGCTAGAGAAACAGAATACTAAGTTGTAAATATGAAAGGATCAAATTTTGGTG
CTACGAGTTTACTATCTTTCATGGTTAAGAGCTGTGTATACATTATAAGTTGTAAATATGAAAGGATCAAATTTTGGTG
TGGATCACTGTTGGGGACTTGGAAGGCTGTGGAAATATGCTTGGGCTCCTAAACCGTATCATAATTCATGGCATTAAGTCT
ATTGCCTTAAAGAATGCTGTGGCACAAGCTTGTGGAAATATGCTTGGGCTCCTAAACCGTATCATAATTCATGGCATTAAGTCT
TTTGCAGATCTCCAGCACTGGTTTCCATGTAATTGATGTTGATTCAGGAAACTCTTATGATATCTTATACATACCATCTCATATT
GGTTCACACACTGGTTTCCATGTAATTGATGTTGATTCAGGAAACTCTTATGATATCTTATACATACCATCTCATATT
CAGGGCAATATCACTCCTCATGTCATCTTGTCATTTGCCTAAAACAGATGGAATGCTTGTTTGCTATGAG
GATGAGGGGTGTATGTAAACACCTAAGGATGTGGTGCTCCAATGGGGAGAAATGCCCACG
TCTGTGCCTACATTGGATGGAGTATTTATGCGAGCTGGGCCAAAGGTTAAAGTTCTATGTGAAAGAAATGATAAGGTA
GGACATTTGGATGGAGTATTTATGCGAGCTGGGCCAAAGGTTAAAGTTCTATGTGAAAGAAATGATAAGGTA
TTTTTTGCATCCGTTGCGATCTGGAGGAAGTAGCCAAGTGTTTTCATGACCCTCAACAGAATTCCATGATGAAC
TGGTAA

*FIG._25B*

```
ATGGCGAGCGACTCCCCGGCTCGAGCCTGGATGAAATAGATCTCTCGGCTCTCTGAGGCTCTGAGGACCCTGCAGGGATCTTT
GAATTGGTGGAACTTGTTGGAAATGGAACATACGGCAAGTTTATAAGGTCGTCATGTCAAGTCAAAACGGGCCAGCTT
GCAGCCATCAAGGTTATGATGTCACAGGGGATGAAGAGGAAGAAATCAAACAAGAGAAATTAACATGTTGAAGAAA
TATTCTCATCACCGAATATTGCTACATACTATGGTGCTTTATCAAAAGAACCCACCAGGCATGGATGACCAA
CTTTGGTTGGTGATGGAGTTTTGTTGGTGCTCTGTGCTGCTCAGGGCTGATCAAGAACACAAAGGTAACACGTTG
AAAGAGGAGTGGATTGCATACATCTGCAGGAAATCTTACGGGGGCTGAGTCACCTGCACCAGCATAAAGTGATT
CATCGAGATATTAAAGGCAAAAATGTCTTGCTGACTGAAAAATGCAGAAGTTAAACTAGTGGACTTTGGAGTCAGT
GCTCAGCTTGATCGAACAGTGGGCAGGAGGAATACTTTCATTGAACTCCCTACTGATGCACCAGAAGTTATT
GCCTGTGATGAAAACCAGATGCCACATCATATGATTTCAAGAGTGACTTGTGTCTTTGGTATCACCGCCATTGAA
ATGGCAGAAGGTGCTCCCCCTCTGTGACATGCAGAGCTCTCTCCTCATCCCCGAATCCAGCG
CCTCGGCTGAAGTCTAAGAAGTGGTCAAAAAAATTCCAGTCATTTATGAGAGCTGCTTGGTAAAGAATCACAGC
CAGCCAGACCAGCAACAGAACAATTGATGAAGCATCCATTTATACGAGACCAACCTAATGAGCGACAGGTCCGCATT
CAACTCAAGGACCATATTGATAGAACAAGAAGCGAGGAGAAAAGATGAGACAGAGTATGAGTACAGTGGA
AGTGAGGAAGAGAGAGGAGAGAATGACTCAGGAGAGCCCAGCTCCATCCTGAATCTGCCAGGGAGTCGACGCTG
CGGAGGGACTTTCTGAGGCTGCCAGCTGCCAACAAGGAGCGTTCTGAGCCCTGCAGAAGCGCAGGAGCAGCTGAGCAG
CAGCAGCGGGAGAATGAGGAGCACAAGCGGCAGTCTGCTGCCGAGCAGCTGCGGAAGGAGCTGCGGAGGAGCAGCGCGG
CAGAGGCGGCGGCTGGAGAGATGCGCCGGGAGGAGGCAGAGGCCGTGCGGAGGCAGCATGAAGAAGCAGGAATATAAGCGCAAACAA
CACTATGAGGAGAACAGAGACAAGCAGAGAAAGACTGCAGAGGCAGCAGCTAAAGCAAGAAGCAGAACAAGAGACTACTTAGTTTCCCTTCAG
TTGGAAGAACAGAGAAGAGGAGCAAGCAGATGCGCAGAGGCAGCAGTCAGAGGCCACTGTACCATTACAAGGAATGAGTCCTAGTGAG
CATCAGCGGCCAGCCATGCGCCAAGGAGGAGTAGAAGAACGGTCAAGGCTCAACCGCCAAAGTTCCCTGCCATGCCTCACAAG
AAGCCAGCATGGAGTAGACCCCAACCTGCCCCCCAAGGTCGGAGTCCTTCAGCATTAGTGGAGTTCAGCCTGCT
GTTGCCAACAGGATATCTGACCCAGACCAGTCGATCCCATCCCCACATCTGGTAGTCGTGTAAAATCCCAGGACCTGCC
CGAACACCCCCATGCTCAGACGCAGCCACGCAGCCACAAAGGCCCTCTCTGGGTTTCAGGAGGCTCTGAACGTGACC
TTGACCGCCTCCAGTCAGTGCCACGCCAGCCAGAACTCAGATCTCCACCTCGGAAAATCCTCTCCCCACTCGATTGAA
TCCCACCGCGTGGAGATGCCGAAGTCTTGGTTACGACAGGAAGAAGACATTCCACCAAAGGTGCCTCAAAGAACAACTTCTATA
AAGTTTGACCAGAAGAATTCTCCTGGAATGGTAGTGCTCTGGGACCCAGACTAGGATCTCAACCCATC
```

*FIG. 26A*

```
AGAGCAAGCAACCCTGATCTCTCCGGAGAGAACTGAGCCTGCAGAGAGGACCAGCAGTGGCAGT
TCCTCCAGCTCCAGCACCCTAGCTCCCAGCCCAGCTCCCAGCTCCCAAGGAGGCTCCTGATCACAAGCAGGATCC
AGTGAACGCACCAGAGTTCGAGCCAACAGTCAGAAGGATCACCTGTGCTTCCCCATGAGCCTGCCAAGGTG
AAACCAGAAGAATCCAGGGACATTACCCGGCCCAGTCTGACCAGCTGATCTGACGGCATTAGCCAAAGAACTAAGA
GAACTCCGATTGAAGAAACAAACCGCCCCAATGAAGAAGGTGACTGATTACTCCTCCAGTGAGGAGTCAGAA
AGTAGCGAGGAAGAGGAGAAGATGAGAGAGCGAGACCCATGATGGGACACCAGTGGCTGTCAGCGACATACCCAGA
CTGATACCAACAGGAGCTCCAGGCGGCAGCAGCAGTACAATGTGGGAATGGTGGGACGCATGGCTGGAGAGACC
TCTCATGCGGACAGTTTCAGCGCGGCAGTATTTCAAGAAGGAACCTTGATGATTAGAGAGACGTCTGCAGCAGAGCCAT
AAGCGATCTGGCCACAGTGACAGCAATGGCTTTGCTGGCCACATCAACCTCCCTGACCTGGTGCAGAGAGACCTGAA
TCTCCAGCTGGCGAACCCCCGACTGAGGGACTCACCCAAAGCCCTCTCAACCCATTCCCAGGAGATGGACTCTGGGACTGAA
TATGGCATGGGGAGCAGCACCAAAGCCTCCAGCCGCCCTTGTGGACCCCAGAGTATACCAGACGTCTCCCACT
GATGAAGATGAAGAGGAGGAATCATCAGCCGCAGTCTGTTTACTAGCGAACTTCTTAGGCAAGAACAGGCC
AAACTCAATGAAGCAAGAAGATTTCGGTGGTAAATGTAAACCAACATTCGGCCTCATAGCGACACACCA
GAAATCAATGGCTGAAAATGGCCTGATGTGCCTAGAGGACTTTTTTGGACCGAAGTGTCCTTGTGACCAAGTCTATAATCTGATCAACCGGAGGCGA
GGGACTGAAATGGCCTGATGTGCCTAGAGGACTGAATGTCCTTGTGACCAAGTGCAATTGTGACAATTGGACCCAGAAGTAGAAAGAAGAATAAGCTACGAGTT
TACTATCTTTCATGGACTTGGAAGGCTGTATACAGAAACAGAATACATTATAAAGTTGTTAAATATGAAAGGATCAAATTTTGGTGATTGCCTTA
GTTGGGGACTTGGAAGGCTGTATACAGAAACAGAATACATTATAAAGTTGTTAAATATGAAAGGATCAAATTTTGGTGATTGCCTTA
AAGAATGCTGTGGAAATATATGCTTGGGCTCCTAGTTGATCTGCTAGTGATGTTGATTCAGAGAAGGTCAAAGATTAAAGGTTATTTTTGGTTCACAC
CTCCAGCACAAGCCTCTGCTAGTTGATCTGCTAGTTGATGTTGATTCAGAGAAACTTCTTATGATATTCTACATGGAAATGCTTGTTGCTATGAGGATGAGGGG
ATCACTCCTCATGCTATTGTCATCTTGCCTAAAACACCTAAGGATGGTGCTCCAATGGGGAGAAATGCCCACGTCTCTGTGGCC
GTGTATGTAAACACCTATGGCCGATAACTAGATAATGGGCTGGGGCGAGAAAGCTATTGAGATCCGGTCAGTGAAACAGGACATTTG
TACATTCATTCCAATCAGATATTTATGCATAAGCGAGCTCAAAGGTCAAAGGTTAAAGTTCTATGTGAAAGAATGATAAGGTATTTTTGCA
GATGGAGTATTTATGCATAAGCGAGCTCAAAGGTCAAAGGTTAAAGTTCTATGTGAAAGAATGATAAGGTATTTTTGCA
TCCGTGCGATCTGGAGGAAGTAGCCCAAGTGTTTTCATGACCCTCAACAGATGTTTTCATGACCCTCAACAGAAATTCCATGATGAACTGGTAA>
```

*FIG.—26B*

```
ATGGCGAGCGACTCCCCGGCTCGAAGCCTGGATGAAATAGATCTCTCGGCTCTGCAGGGACCCTGCAGGGATCTTT
GAATTGGTGGAACTTGTGTTGGAAATGGAACATACGGGCAAGTTTATAAGGGTCGTCATGTCAAAACGGGCCAGCTT
GCAGCCATCAAGGTTATGATGTCACAGGGGATGAAGAGGAAGAAATCAAACAGAATTAACATGTTGAAGAAA
TATTCTCATCACCGGAATATTGCTACTACATATGGTCTCTGTGCTGGTCTCAAGAACCCACCAGGCATGGATGACCAA
CTTTGGTTGGTGATGGAGTTTTGTGGTCTGCAGGGAAATCTTACGGGCTGACCTGAGTCACTGCACCAGACAAAGTAACACGTTG
AAAGAGGAGTGGATTGCATACATCTGCAGGGAAATCTTACGGGCTGAGTCACTGCACCAGCATAAAGTGATT
CATCGAGATATTAAAGGGCAAAATGTCTTGCTGACTGAAAATGCAGAAGTTAAACTAGTGGACTTTGGAGTCAGT
GCTCAGCTTGATCGAACAGTGGGCAGGAGGAATACTTTCATTGGAACTCCCTACTGATGGCACCAGAAGTTATT
GCCTGTGATGAAAACCCAGATGCCACATATGATTCAAGAGTGACTTGTGTGTCTTTGGGTATCACCGCCATTGAA
ATGGCAGAAGGTGCTCCCCCTCTGTGACATGCACCCCATGAGAGCTCTTCCTCATCCCCGGAATCCAGCG
CCTCGGCTGAAGTCTAAGACAGAACAATTGATGAAGCATCCATTTATACGAGACCAATTCCAGTGACGACAGTCCGCATT
CAGCGACCAGCAACAGAACAATTGATGAACAAAAGAGAGAAAAAGATGAGACAGAGTAGTAGTACAGTGGA
AGTGAGGAAGAGAGGAGAATGACTCAGGAGAGCTCCAGCTCTGAATCTGCCAGGGAGTCGACGCTG
CGGAGGGACTTTCTGAGGCTGCAGCTGCCAACAAGGAGCGTTCTGAGGCCCTGGAGGCAGCAGCTGGAGCAG
CAGAGCGGGAGAATGAGGAGCACACAGGGCAGCTGCTGGCCAGCGTGCGGAGAAGCGCAGGAGCAGCAGAAGAG
CAGAGGCGGCGGCTGGAGCAGACAGCAACAAGGCGAGGAGGAGGAGGCGTGCGGAAGCAGCATGAACAGGAATACATCAGGCGACAG
CACTATGAGAGGCAGCAGAGACAGTTAGAGATCTTGCAGCAGCTACTGCATGACGCAGAAGCTTCTACTTCTGAATAT
TTAGAGGAGGAGCAGAGACAGTTAGAGATCTTGCAGCAGCTACTGCATGACGCAGCTAAAGCAAGAAAGAGACTACTTA
AAGCGCAAACAATTGGAACGGCATCAGCGCAGAAGCATGGGCCAGGAGATCCCACATCTGGTAGCTGTGTAAAATCCAGGACCTGCCTTG
GTTCCCTTCAGCATCGAGAAGCTCAGTGCACGAGATGGGCCAGGAGATCCCACATCTGGTAGCTGTGTAAAATCCAGGACCTGCCTTG
AGTCCTAGTGAGAAGCTCAGTGCACGAGATGGCCAGAGCAGCCAGAACTCAGATCCCACAAAGGCCTCTCTGGGTTTCAGGGCTCTGACCTGACCTCC
ACCGGCCTCCCAGTGCCACGCCAGAACTCAGATCCCACAAAGGCCTCTCTGGGTTTCAGGGCTCTGACCTGACCTCC
CACCGCGTGGAGATGCCAGTGCCACGCCAGAACTCAGATCCCACAAAGGCCTCTCTGGGTTTCAGGGCTCTGACCTGACCTCC
TTTGACCGAAGCTCTTGGTTACGACAGGAAGAAGACATTCCACCAAAGGTGCCTCAAAGAACAACTTCTATATCC
CCAGCATTAGCCAGACCAGAAAGAATTCTCCTGGAATGGTAGTGCTCTGGGACCCAGACTAGGATCTCAACCCATCAGA
GCAAGCAACCCTGATCTCCGAGAACTGAGCCCATCTGGAGAGCCCCCTTGCAGAGGACCAGAGCAGTGGCAGTTCC
```

```
ATGGCGAGCGACTCCCCCGGCTCGAAGCCTGAAGCCTGGATGAAATAGATCTCTCGGCTCTGAGGACCCTGCAGGGATCTTT
GAATTGGTGGAACTTGTTGGAAATGGAACATACGGGCAAGTTTATAAGGGTCGTCATGTCAAAACGGGCCAGCTT
GCAGCCATCAAGGTTATGATGTCACAGGGGATGAAGAGGAAGAAATCAAACAAGAAATTAACATGTTGAAGAAA
TATTCTCATCACCGGAATATTGCTACATACTATGGTGCTTTTATCAAAAGAACCCACCAGGCATGGATGACCAA
CTTTGGTGGTGGATGGAGTTTTGTGGTGCTGGCTCTCTGTCACCGGCTGATCAAGAACACAAAGGTAACACGTTG
AAAGAGGAGTGGATTGCATACATCTGCAGGGAAATCTTACGGGGCTGAGTCACCTGCACCAGCATAAAGTGATT
CATCGAGATATTAAAGGCAAAATGTCTTGTGACTGAAAATGCAGAAGTTAAACTAGTGGACTTTGGAGTCAGT
GCTCAGCTTGATCGAACAGTGGGCAGGAGAATACTTTCATTGGAACTCCCTACTGGATGGCACCAGAAGTTATT
GCCTGTGATGAAAACCCAGATGCCACACATATGATTTCAAGAGTGACTTGTGGTCTTTGGGTATCACCGCCATTGAA
ATGGCAGAAGGTGCTCCCCCTCTCTGTGACACTGACCCCCATGAGAGCTCTCTTCCTCATCCCCGAATCCAGCG
CCTCGGCTGAAGTCTAAGAAGTGGTCAAAAAATTCCAGTCATTTATTGAGAGCTGCTTGGTAAAGAATCACAGC
CAGCGACCAGCAACAGAACAATTGATGAACAACAAAGCATCCATTTATACGAGGACCAACCTAATGACGACAGGTCCGCATT
CAACTCAAGGACCATATTGATAGAACAAAGAAAGCGAGGAGAAAAAGATGAGACAGAGTATGAGTACAGTGGA
AGTGAGGAAGAAGAGGAGAATGACTCAGGAGAGCCCAGCTCCATCCTGAATCTGCCAGGGAGTCGACGCTG
CGGAGGGACTTTCTGAGGCTGGCCAACAAGGAGCGTTCTGAGGCCTGCCCAGAAGCGCATCGAGGAGCAGCAGAG
CAGCAGCGGGAGAATGAGGAGCACAAGCGGCAGCTGCTGCCGGAAGCAGCAGGAGAGGAGCAGCAGCGCCGG
CACTATGAGGAGCAGAGATGCGCCGGGAGGAGGCAGCGTGCGGAGCATGAACAGGAATATAAGCCAAACAA
TTGGAAGAACAGAGAACAAGCAGAGAAGACTCAGAGGCAGCTAAAGCAAGAAAGAGACTTAGTTTCCCTTCAG
CATCAGCGGCAGCAGCCATGGCTGTGAGAGAAGAAGCCCACATCTGGTAGCTGTAAAAATCCCAGGACCTGCCTTGACCCTTGACCTGGAG
AAGCCAGCATGGGCCAAGGAGATCCCACATGGCCTCTGGGTTTCAGGAGGCTCTGAACGTGACGTGACCTCCCACCGCGTGGAG
TCAGTGCACGAGCAGCAGAACTCAGATCCCAGGAAGACATTCCACCAAAGGTGCCTCAAAGAACAACTTCTATATCCCCAGCATTAGCC
ATGCCACGCCAGAATCTCCTGTTGACAGGAAGACATTCCACCAAAGGTGCCTCAAAGAACAACTTCTATATCCCCAGCATTAGCC
TCTTGGTTACGACAGGAAGAAGACATTCCACCAAAGGTGCCTCAAAGAACAACTTCTATATCCCCAGCATTAGCC
AGAAAGAATTCTCTGGGATGTAGTGCTCTGGAGAGACCCCCTTGCAGAGGACCAGCAGTGGCAGTTCCTCCAGCAACCCT
GATCTCCGAGAACTGAGCCCCATCTGAGCCCATCTGGAGAGAGCCCCTTGCAGAGGACCAGCAGTGGCAGTTCCTCCAGC
ACCCCTAGCTCCCCAGCTCCCCAGCTCCCCAAGGAGGCTCCCAGCTGAGCCTGATCACAAGCAGGATCACAAGCAGGAT
```

FIG._28A

```
GTTCGAGCCAACAGTAAGTCAGAAGGATCACCTGTGCTTCCCCATGAGCCTGCCAAGTGAAACCAGAAGAATCC
AGGGACATTACCCGGCCCAATGAAGAGAGCGAGACCAGTCGATCTGACGGCATTAGCCAAAGAACTAAGAGAACTCCGATTGAA
GAAACAAACCGCCCAATGAAGAGAGCGAGACCAGTGACTGATTACTCCTCCAGTGAGGAGTCAGAAAGTAGCGAGGAAGAG
GAGGAAGAGATGGAGAGCGAGACCAGTCGAGCAGTCCATGATGGGACAGAGTGGGGACGCATGGCTGGAGACCCTCTCATGCGACAGT
GCTCCAGGCAGCAACGAGCAGTACAATGTGGGAACCTGATGATTAGAGAGACGTCTGGAGAGAAGAAGCGATCTGGCCAC
TTCAGCGGCAGTATTTCAAGAGGCTTTGCTGGCCACATCAACCTCCCTGACCTGGTGCAGCAGCCATTCTCCAGCTGGAACC
AGTGACAGCAATGGCTTTGCTGGCCACATCAACCTCCCTGACCTGGTGCAGCAGCCATTCTCCAGCTGGAACC
CCGACTGAGGACTGGGCGCGTCTCACCCCCTTTGTGGACCCCAGAGTATACCAGACGTCTCCCACTGATGAAGATGAAGAG
AGCACCAAAGCCTCCTTCACCCCCTTTGTGGACCCCAGAGTATACCAGACGTCTCCCACTGATGAAGATGAAGAG
GATGAGGAATCATCAGCCGCAGCTCTGTTTTACTAGCGAACTTCTTAGGCAAGAACAGGCCAAATCAGAAATCAGAAGCA
AGAAAGATTTCGGTGTGTAAATGTAAACCAACATTCGGCTCATAGCGACACACCAGAAATCAGAAATAC
AAGAAACGATTCAACTCAGAATACTTTGTGCAGTCTCGTGGGGTAAACCTTCTGGTGGGACTGAAAATGGC
CTGATGCTCTTTTGGACCGAAGTGGCCAAGGCAAAGTTCTTATAATCAACCGGAGCGATTTCAGCAGATGAT
GTGCTAGAGGGACTGAATGTCCTTGTGACAATTCAAGAAGAAGTAGAAGAAGCTACGAGTTTACTACTGTTGGGACTTGAA
TTAAGAAACAGAATACATTATAAGTTGTTAAATATGAAAGGATCAAATTTTGGTGATGCCTAAAAGAATGCTGTGAAA
GGCTGTATACATTATAAGTTGTTAAATATGAAAGGATCAAATTTTGGTGATGCCTTAAAGAATGCTGTGAAA
ATATATGCTTGGGCTCCTAAACCGTATCATAAATTTCATGAAAGATTAAAGATTCACACACTGGTTTCCATGTA
CTGCTAGTTGATCTCACGGTAGAAGAAGTCAAAGATTAAAGGTTATTTGTTCACACACTGGTTTCCATGTA
ATTGATGTGATTCAGGAAACTCTTATGATATCTACAATCCATCATTCAGGGGCAATATCACTCCTCCATGCT
ATTGTCATCTTGCCTAAAACAGATGGAATGGAAAATGCTTGTTGCTATGAGGATGAGGGGGTGTATGTAAACACC
TATGGCCGGATAACTAAGGATGTGTGCTCCAATGGGCTATTGAGATCCGGTCAGTGGAAAATGCCACGTCTGTGCCTACATTCATTCCAAT
CAGATAATGGGCTGGGGCGAGAAGGTTAAGTTTCTATGTGAAAGAAATGATAAGGTATTTTTGCATCCGTGCGATCTGGA
CATAAGCGAGCCAAGTGTTTTTCATGACCCCTCAACAGAAATTCATGATGAACTGGTAA
GGAAGTAGCCAAGTGTTTTTCATGACCCCTCAACAGAAATTCATGATGAACTGGTAA
```

FIG._28B

```
   1  MASDSPARSLDEIDLSALRDPAGIFELVELVGNGTYGQVYKGRHVKTGQLAAIKVMDVTG
  61  DEEEIKQEINMLKKYSHHRNIATYYGAFIKKNPPGMDDQLWLMEFCGAGSVTDLIKNT
 121  KGNTLKEEWIAYICREILRGLSHLHQHKVIHRDIKGQNVLLTENAEVKLVDFGVSAQLDR
 181  TVGRRNTFIGTPYWMAPEVIACDENPDATYDFKSDLWSLGITAIEMAEGAPPLCDMHPMR
 241  ALFLIPRNPAPRLKSKKWSKKFQSFIESCLVKNHSQRPATEQLMKHPFIRDQPNERQVRI
 301  QLKDHIDRTKKKRGEKDETEYEYSGSEEEEENDSGEPSSILNLPGESTLRRDFLRLQLA
 361  NKERSEALRRQQLEQQQRENEEHKRQLLAERQKRIEEQKEQRRLEEQQRREKELRKQQE
 421  REQRRHYEEQMREEERRRAEHEQEYKRKQLEEQRQAERLQRQLKQERDYLVSLQHQRQE
 481  QRPVEKKPLYHYKEGMSPSEKPAWAKEVEERSRLNRQSSPAMPHKVANRISDPNLPPRSE
 541  SFSISGVQPARTPPMLRPVDPQIPHLVAVKSQGPALTASQSVHEQPTKGLSGFQEALNVT
 601  SHRVEMPRQNSDPTSENPPLPTRIEKFDRSSWLRQEEDIPPKVPQRTTSISPALARKNSP
 661  GNGSALGPRLGSQPIRASNPDLRRTEPILESPLQRTSSGSSSSTPSSQPSSQGGSQPG
 721  SQAGSSERTRVRANSKSEGSPVLPHEPAKVKPEESRDITRPSRPASYKKAIDEDLTALAK
 781  ELRELRIEETNRPMKKVTDYSSSSEESESEEEEDGESETHDGTVAVSDIPRLIPTGAP
 841  GSNEQYNVGMVGTHGLETSHADSFSGSISREGTLMIRETSGEKKRSGHSDSNGFAGHINL
 901  PDLVQQSHSPAGTPTEGLGRVSTHSQEMDSGTEYGMGSSTKASFTPFVDPRVYQTSPTDE
 961  DEEDEESSAAALFTSELLRQEQAKLNEARKISVVNVNPTNIRPHSDTPEIRKYKKRFNSE
1021  ILCAALWGVNLLVGTENGLMLLDRSGQGKVYNLINRRRFQQMDVLEGLNVLVTISGKKNK
1081  LRVYYLSWLRNRILHNDPEVEKKQGWITVGDLEGCIHYKVKYERIKFLVIALKNAVEIY
1141  AWAPKPYHKFMAFKSFADLQHKPLLVDLTVEEGQRLKVIFGSHTGFHVIDVDSGNSYDIY
1201  IPSHIQGNITPHAIVILPKTDGMEMLVCYEDEGVYVNTYGRITKDVVLQWGEMPTSVAYI
1261  HSNQIMGWGEKAIEIRSVETGHLDGVFMHKRAQRLKFLCERNDKVFFASVRSGGSSQVFF
1321  MTLNRNSMNWZ
```

FIG._29

```
   1  MASDSPARSLDEIDLSALRDPAGIFELVELVGNGTYGQVYKGRHVKTGQLAAIKVMDVTG
  61  DEEEIKQEINMLKKYSHHRNIATYYGAFIKKNPPGMDDQLWLVMEFCGAGSVTDLIKNT
 121  KGNTLKEEWIAYICREILRGLSHLHQHKVIHRDIKGQNVLLTENAEVKLVDFGVSAQLDR
 181  TVGRRNTFIGTPYWMAPEVIACDENPDATYDFKSDLWSLGITAIEMAEGAPPLCDMHPMR
 241  ALFLIPRNPAPRLKSKKWSKKFQSFIESCLVKNHSQRPATEQLMKHPFIRDQPNERQVRI
 301  QLKDHIDRTKKRGEKDETEYEYSGSEEEEENDSGEPSSILNLPGESTLRRDFLRLQLA
 361  NKERSEALRRQQLEQQQRENEEHKRQLLAERQKRIEEQKEQRRLEEQQRREKELRKQQE
 421  REQRRHYEEQMRREEERRAEHEQEYIRRQLEEEQRQLEILQQLLHEQALLLEYKRKQL
 481  EEQRQAERLQRQLKQERDYLVSLQHQRQEQRPVEKKPLYHYKEGMSPSEKPAWAKEIPHL
 541  VAVKSQGPALTASQSVHEQPTKGLSGFQEALNVTSHRVEMPRQNSDPTSENPLPTRIEK
 601  FDRSSWLRQEEDIPPKVPQRTTSISPALARKNSPGNGSALGPRLGSQPIRASNPDLRRTE
 661  PILESPLQRTSGSSSSSTPSSQPSSQGSQPGSQAGSSERTRVRANSKSEGSPVLPHE
 721  PAKVKPEESRDITRPSRPASYKKAIDEDLTALAKELRELRIEETNRPMKKVTDYSSSEE
 781  SESSEEEEDGESETHDGTVAVSDIPRLIPTGAPGSNEQYNVGMVGTHGLETSHADSFSG
 841  SISREGTLMIRETSGEKKRSGHSDSNGFAGHINLPDLVQQSHSPAGTPTEGLGRVSTHSQ
 901  EMDSGTEYGMSSTKASFTPFVDPRVYQTSPTDEDEDESSAAALFTSELLRQEQAKLN
 961  EARKISVVNVNPTNIRPHSDTPEIRKYKKRFNSEILCAALWGVNLLVGTENGLMLLDRSG
1021  QGKVYNLINRRFQQMDVLEGLNVLVTISGKKNKLRVYYLSWLRNRILHNDPEVEKKQGW
1081  ITVGDLEGCIHYKVVKYERIKFLVIALKNAVEIYAWAPKPYHKFMAFKSFADLQHKPLLV
1141  DLTVEEGQRLKVIFGSHTGFHVIDVDSGNSYDIYIPSHIQGNITPHAIVILPKTDGMEML
1201  VCYEDEGVYVNTYGRITKDVVLQWGEMPTSVAYIHSNQIMGWGEKAIEIRSVETGHLDGV
1261  FMHKRAQRLKFLCERNDKVFFASVRSGGSSQVFFMTLNRNSMMNWZ
```

*FIG. 30*

```
   1  MASDSPARSLDEIDLSALRDPAGIFELVELVGNGTYGQVYKGRHVKTGQLAAIKVMDVTG
  61  DEEEIKQEINMLKKYSHHRNIATYYGAFIKKNPPGMDDQLWLVMEFCGAGSVTDLIKNT
 121  KGNTLKEEWIAYICREILRGLSHLHQHKVIHRDIKGQNVLLTENAEVKLVDFGVSAQLDR
 181  TVGRRNTFIGTPYWMAPEVIACDENPDATYDFKSDLWSLGITAIEMAEGAPPLCDMHPMR
 241  ALFLIPRNPAPRLKSKKWSKKFQSFIESCLVKNHSQRPATEQLMKHPFIRDQPNERQVRI
 301  QLKDHIDRTKKKRGEKDETEYEYSGSEEEEENDSGEPSSILNLPGESTLRRDFLRLQLA
 361  NKERSEALRRQQLEQQQRENEEHKRQLLAERQKRIEEQKEQRRLEEQQRREKELRKQQE
 421  REQRRHYEEQMRREERRAEHEQEYIRRQLEEEQRQLEILQQQLLHEQALLLEYKRKQL
 481  EEQRQAERLQRQLKQERDYLVSLQHQRQEQRPVEKKPLYHYKEGMSPSEKPAWAKEVEER
 541  SRLNRQSSPAMPHKVANRISDPNLPPRSESFSISGVQPARTPPMLRPVDPQIPHLVAVKS
 601  QGPALTASQSVHEQPTKGLSGFQEALNVTSHRVEMPRQNSDPTSENPPLPTRIEKFDRSS
 661  WLRQEEDIPPKVPQRTTSISPALARKNSPGNGSALGPRLGSQPIRASNPDLRRTEPILES
 721  PLQRTSGSGSSSSSTPSSQPSSQGGSQPGSQAGSSERTRVRANSKSEGSPVLPHEPAKVK
 781  PEESRDITRPSRPADLTALAKELRELRIEETNRPMKKVTDYSSSSEESESSEEEEDGES
 841  ETHDGTVAVSDIPRLIPTGAPGSNEQYNVGMVGTHGLETSHADSFSGSISREGTLMIRET
 901  SGEKKRSGHSDSNGFAGHINLPDLVQQSHSPAGTPTEGLGRVSTHSQEMDSGTEYGMGSS
 961  TKASFTPFVDPRVYQTSPTDEDEEDESSAAALFTSELLRQEQAKLNEARKISVVNVNPT
1021  NIRPHSDTPEIRKYKKRFNSEILCAALWGVNLLVGTENGLMLLDRSGQGKVYNLINRRRF
1081  QQMDVLEGLNVLVTISGKKNKLRVYYLSWLRNRILHNDPEVEKKQGWITVGDLEGCIHYK
1141  VVKYERIKFLVIALKNAVEIYAWAPKPYHKFMAFKSFADLQHKPLLVDLTVEEGQRLKVI
1201  FGSHTGFHVIDVDSGNSYDIYIPSHIQGNITPHAIVILPKTDGMEMLVCYEDEGVYVNTY
1261  GRITKDVVLQWGEMPTSVAYIHSNQIMGWGEKAIEIRSVETGHLDGVFMHKRAQRLKFLC
1321  ERNDKVFFASVRSGGSSQVFFMTLNRNSMMNWZ
```

FIG._31

```
   1  MASDSPARSLDEIDLSALRDPAGIFELVELVGNGTYGQVYKGRHVKTGQLAAIKVMDVTG
  61  DEEEEIKQEINMLKKYSHHRNIATYYGAFIKKNPPGMDDQLWLVMEFCGAGSVTDLIKNT
 121  KGNTLKEEWIAYICREILRGLSHLHQHKVIHRDIKGQNVLLTENAEVKLVDFGVSAQLDR
 181  TVGRRNTFIGTPYWMAPEVIACDENPDATYDFKSDLWSLGITAIEMAEGAPPLCDMHPMR
 241  ALFLIPRNPAPRLKSKKWSKKFQSFIESCLVKNHSQRPATEQLMKHPFIRDQPNERQVRI
 301  QLKDHIDRTKKKRGEKDETEYEYSGSEEEEENDSGEPSSILNLPGESTLRRDFLRLQLA
 361  NKERSEALRRQQLEQQQRENEEHKRQLLAERQKRIEEQKEQRRLEEQQRREKELRKQQE
 421  REQRRHYEEQMRREEERRRAEHEQEYKRKQLEEQRQAERLQRQLKQERDYLVSLQHQRQE
 481  QRPVEKKPLYHYKEGMSPSEKPAWAKEIPHLVAVKSQGPALTASQSVHEQPTKGLSGFQE
 541  ALNVTSHRVEMPRQNSDPTSENPLPTRIEKFDRSSWLRQEEDIPPKVPQRTTSISPALA
 601  RKNSPGNGSALGPRLGSQPIRASNPDLRRTEPILESPLQRTSSGSSSSTPSSQPSSQG
 661  GSQPGSQAGSSERTRVRANSKSEGSPVLPHEPAKVKPEESRDITRPSRPASYKKAIDEDL
 721  TALAKELRELRIEETNRPMKKVTDYSSSEESESSEEEEDGESETHDGTVAVSDIPRLI
 781  PTGAPGSNEQYNVGMVGTHGLETSHADSFSGSISREGTLMIRETSGEKKRSGHSDSNGFA
 841  GHINLPDLVQQSHSPAGTPTEGLGRVSTHSQEMDSGTEYGMGSSTKASFTPFVDPRVYQT
 901  SPTDEDEESSAAALFTSELLRQEQAKLNEARKISVVNVNPTNIRPHSDTPEIRKYKK
 961  RFNSEILCAALWGVNLLVGTENGLMLLDRSGQGKVYNLINRRFQQMDVLEGLNVLVTIS
1021  GKKNKLRVYYLSWLRNRILHNDPEVEKKQGWITVGDLEGCIHYKVVKYERIKFLVIALKN
1081  AVEIYAWAPKPYHKFMAFKSFADLQHKPLLVDLTVEEGQRLKVIFGSHTGFHVIDVDSGN
1141  SYDIYIPSHIQGNITPHAIVILPKTDGMEMLVCYEDEGVYVNTYGRITKDVVLQWGEMPT
1201  SVAYIHSNQIMGWGEKAIEIRSVETGHLDGVFMHKRAQRLKFLCERNDKVFFASVRSGGS
1261  SQVFFMTLNRNSMMNWZ
```

*FIG._32*

```
   1  MASDSPARSLDEIDLSALRDPAGIFELVELVGNGTYGQVYKGRHVKTGQLAAIKVMDVTG
  61  DEEEEIKQEINMLKKYSHHRNIATYYGAFIKKNPPGMDDQLWLVMEFCGAGSVTDLIKNT
 121  KGNTLKEEWIAYICREILRGLSHLHQHKVIHRDIKGQNVLLTENAEVKLVDFGVSAQLDR
 181  TVGRRNTFIGTPYWMAPEVIACDENPDATYDFKSDLWSLGITAIEMAEGAPPLCDMHPMR
 241  ALFLIPRNPAPRLKSKKWSKKFQSFIESCLVKNHSQRPATEQLMKHPFIRDQPNERQVRI
 301  QLKDHIDRTKKKRGEKDETEYEYSGSEEEEENDSGEPSSILNLPGESTLRRDFLRLQLA
 361  NKERSEALRRQQLEQQQRENEEHKRQLLAERQKRIEEQKEQRRLEEQQRREKELRKQQE
 421  REQRRHYEEQMRREERRRAEHEQEYKRKQLEEQRQAERLQRQLKQERDYLVSLQHQRQE
 481  QRPVEKKPLYHYKEGMSPSEKPAWAKEVEERSRLNRQSSPAMPHKVANRISDPNLPPRSE
 541  SFSISGVQPARTPPMLRPVDPQIPHLVAVKSQGPALTASQSVHEQPTKGLSGFQEALNVT
 601  SHRVEMPRQNSDPTSENPPLPTRIEKFDRSSWLRQEEDIPPKVPQRTTSISPALARKNSP
 661  GNGSALGPRLGSQPIRASNPDLRRTEPILESPLQRTSSGSSSSSTPSSQPSSQGGSQPG
 721  SQAGSSERTRVRANSKSEGSPVLPHEPAKVKPEESRDITRPSRPADLTALAKELRELRIE
 781  ETNRPMKKVTDYSSSSEESESSEEEEEDGESETHDGTVAVSDIPRLIPTGAPGSNEQYNV
 841  GMVGTHGLETSHADSFSGSISREGTLMIRETSGEKKRSGHSDSNGFAGHINLPDLVQQSH
 901  SPAGTPTEGLGRVSTHSQEMDSGTEYGMGSSTKASFTPFVDPRVYQTSPTDEDEDEESS
 961  AAALFTSELLRQEQAKLNEARKISVVNVNPTNIRPHSDTPEIRKYKKRFNSEILCAALWG
1021  VNLLVGTENGLMLLDRSGQGKVYNLINRRFQQMDVLEGLNVLVTISGKKNKLRVYYLSW
1081  LRNRILHNDPEVEKKQGWITVGDLEGCIHYKVVKYERIKFLVIALKNAVEIYAWAPKPYH
1141  KFMAFKSFADLQHKPLLVDLTVEEGQRLKVIFGSHTGFHVIDVDSGNSYDIYIPSHIQGN
1201  ITPHAIVILPKTDGMEMLVCYEDEGVVYNTYGRITKDVVLQWGEMPTSVAYIHSNQIMGW
1261  GEKAIEIRSVETGHLDGVFMHKRAQRLKFLCERNDKVFFASVRSGGSSQVFFMTLNRNSM
1321  MNWZ
```

FIG._33

```
   1  MASDSPARSLDEIDLSALRDPAGIFELVELVGNGTYGQVYKGRHVKTGQLAAIKVMDVTG
  61  DEEEEIKQEINMLKKYSHHRNIATYYGAFIKKNPPGMDDQLWLVMEFCGAGSVTDLIKNT
 121  KGNTLKEEWIAYICREILRGLSHLHQHKVIHRDIKGQNVLLTENAEVKLVDFGVSAQLDR
 181  TVGRRNTFIGTPYWMAPEVIACDENPDATYDFKSDLWSLGITAIEMAEGAPPLCDMHPMR
 241  ALFLIPRNPAPRLKSKKWSKFQSFIESCLVKNHSQRPATEQLMKHPFIRDQPNERQVRI
 301  QLKDHIDRTKKKRGEKDETEYEYSGSEEEEENDSGEPSSILNLPGESTLRRDFLRLQLA
 361  NKERSEALRRQQLEQQQRENEEHKRQLLAERQKRIEEQKEQRRLEEQQRREKELRKQQE
 421  REQRRHYEEQMREEERRAEHEQEYIRRQLEEEQRQLEILQQQLLHEQALLLEYKRKQL
 481  EEQRQAERLQRQLKQERDYLVSLQHQRQEQRPVEKKPLYHYKEGMSPSEKPAWAKEIPHL
 541  VAVKSQGPALTASQSVHEQPTKGLSGFQEALNVTSHRVEMPRQNSDPTSENPPLPTRIEK
 601  FDRSSWLRQEEDIPPKVPQRTTSISPALARKNSPGNGSALGPRLGSQPIRASNPDLRRTE
 661  PILESPLQRTSGSSSSSTPSSQPSSQGSQPGSQAGSSERTRVRANSKSEGSPVLPHE
 721  PAKVKPEESRDITRPSRPADLTALAKELRELRIEETNRPMKKVTDYSSSEESESSEEEE
 781  EDGESETHDGTVAVSDIPRLIPTGAPGSNEQYNVGMVGTHGLETSHADSFSGSISREGTL
 841  MIRETSGEKKRSGHSDSNGFAGHINLPDLVQQSHSPAGTPTEGLGRVSTHSQEMDSGTEY
 901  GMGSSTKASFTPFVDPRVYQTSPTDEDEEDEESSAAALFTSELLRQEQAKLNEARKISVV
 961  NVNPTNIRPHSDTPEIRKYKKRFNSEILCAALWGVNLLVGTENGLMLLDRSGQKVYNLI
1021  NRRRFQQMDVLEGLNVLVTISGKKNKLRVYYLSWLRNRILHNDPEVEKKQGWITVGDLEG
1081  CIHYKVKYERIKFLVIALKNAVEIYAWAPKPYHKFMAFKSFADLQHKPLLVDLTVEEGQ
1141  RLKVIFGSHTGFHVIDVDSGNSYDIYIPSHIQGNITPHAIVILPKTDGMEMLVCYEDEGV
1201  YVNTYGRITKDVVLQWGEMPTSVAYIHSNQIMGWGEKAIEIRSVETGHLDGVFMHKRAQR
1261  LKFLCERNDKVFFASVRSGGSSQVFFMTLNRNSMMNWZ
```

*FIG._34*

```
   1  MASDSPARSLDEIDLSALRDPAGIFELVELVGNGTYGQVYKGRHVKTGQLAAIKVMDVTG
  61  DEEEIKQEINMLKKYSHHRNIATYYGAFIKKNPPGMDDQLWLVMEFCGAGSVTDLIKNT
 121  KGNTLKEEWIAYICREILRGLSHLHQHKVIHRDIKGQNVLLTENAEVKLVDFGVSAQLDR
 181  TVGRRNTFIGTPYWMAPEVIACDENPDATYDFKSDLWSLGITAIEMAEGAPPLCDMHPMR
 241  ALFLIPRNPAPRLKSKKWSKKFQSFIESCLVKNHSQRPATEQLMKHPFIRDQPNERQVRI
 301  QLKDHIDRTKKRGEKDETEYEYSGSEEEEENDSGEPSSILNLPGESTLRRDFLRLQLA
 361  NKERSEALRRQQLEQQQRENEEHKRQLLAERQKRIEEQKEQRRLEEQQRREKELRKQQE
 421  REQRRHYEEQMREEERRAEHEQEYKRKQLEEQRQAERLQRQLKQERDYLVSLQHQRQE
 481  QRPVEKKPLYHYKEGMSPSEKPAWAKEIPHLVAVKSQGPALTASQSVHEQPTKGLSGFQE
 541  ALNVTSHRVEMPRQNSDPTSENPPLPTRIEKFDRSSWLRQEEDIPPKVPQRTTSISPALA
 601  RKNSPGNGSALGPRLGSQPIRASNPDLRRTEPILESPLQRTSSGSSSSSTPSSQPSSQG
 661  GSQPGSQAGSSERTRVRANSKSEGSPVLPHEPAKVKPEESRDITRPSRPADLTALAKELR
 721  ELRIEETNRPMKKVTDYSSSEESESSEEEEDGESETHDGTVAVSDIPRLIPTGAPGSN
 781  EQYNVGMVGTHGLETSHADSFSGSISREGTLMIRETSGEKKRSGHSDSNGFAGHINLPDL
 841  VQQSHSPAGTPTEGLGRVSTHSQEMDSGTEYGMGSSTKASFTPFVDPRVYQTSPTDEDEE
 901  DEESSAAALFTSELLRQEQAKLNEARKISVVNVNPTNIRPHSDTPEIRKYKKRFNSEILC
 961  AALWGVNLLVGTENGLMLLDRSGQGKVYNLINRRRFQQMDVLEGLNVLVTISGKKNKLRV
1021  YYLSWLRNRILHNDPEVEKKQGWITVGDLEGCIHYKVVKYERIKFLVIALKNAVEIYAWA
1081  PKPYHKFMAFKSFADLQHKPLLVDLTVEEGQRLKVIFGSHTGFHVIDVDSGNSYDIYIPS
1141  HIQGNITPHAIVILPKTDGMEMLVCYEDEGVYVNTYGRITKDVVLQWGEMPTSVAYIHSN
1201  QIMGWGEKAIEIRSVETGHLDGVFMHKRAQRLKFLCERNDKVFFASVRSGGSSQVFFMTL
1261  NRNSMMNWZ
```

*FIG._35*

SEQUENCE LISTING

<160> NUMBER OF SEQ ID NOS: 36

<210> SEQ ID NO 1
<211> LENGTH: 4083
<212> TYPE: DNA
<213> ORGANISM: Artificial sequence
<220> FEATURE:
<223> OTHER INFORMATION: synthetic

<400> SEQUENCE: 1

```
atggcgagcg actccccggc tcgaagcctg gatgaaatag atctctcggc tctgagggac      60
cctgcaggga tctttgaatt ggtggaactt gttggaaatg aacatacgg gcaagtttat      120 aagggtcgtc atgtcaaaac gggccagctt gcagccatca aggttatgga tgtcacaggg      180
gatgaagagg aagaaatcaa acaagaaatt aacatgttga agaaatattc tcatcaccgg      240
aatattgcta catactatgg tgcttttatc aaaaagaacc caccaggcat ggatgaccaa      300
ctttggttgg tgatggagtt ttgtggtgct ggctctgtca ccgacctgat caagaacaca      360
aaaggtaaca cgttgaaaga ggagtggatt gcatacatct gcagggaaat cttacgggg      420 ctgagtcacc tgcaccagca taaagtgatt catcgagata ttaaagggca aaatgtcttg      480
ctgactgaaa atgcagaagt taaactagtg gactttggag tcagtgctca gcttgatcga      540
acagtgggca ggaggaatac tttcattgga actccctact ggatggcacc agaagttatt      600
gcctgtgatg aaaacccaga tgccacatat gatttcaaga gtgacttgtg gtctttgggt      660
atcaccgcca ttgaaatggc agaaggtgct cccctctct gtgacatgca ccccatgaga     720
gctctcttcc tcatcccccg gaatccagcg cctcggctga agtctaagaa gtggtcaaaa     780
aaattccagt catttattga gagctgcttg gtaaagaatc acagccagcg accagcaaca     840
gaacaattga tgaagcatcc atttatacga gaccaaccta atgagcgaca ggtccgcatt     900
caactcaagg accatattga taacaaag aagaagcgag gagaaaaaga tgagacagag     960
tatgagtaca gtgaagtga ggaagaagag gaggagaatg actcaggaga gcccagctcc    1020
atcctgaatc tgccaggga gtcgacgctg cggagggact ttctgaggct gcagctggcc    1080
```

-continued

```
aacaaggagc gttctgaggc cctacggagg cagcagctgg agcagcagca gcggagaat    1140
gaggagcaca agcggcagct gctggccgag cgtcagaagc gcatcgagga gcagaaagag    1200
cagaggcggc ggctggagga gcaacaaagg cgagagaagg agctgcggaa gcagcaggag    1260
agggagcagc gccggcacta tgaggagcag atgcgccggg aggaggagag gaggcgtgcg    1320
gagcatgaac aggaatacat caggcgacag ttagaggagg agcagagaca gttagagatc    1380
ttgcagcagc agctactgca tgaacaagct ctacttctgg aatataagcg caaacaattg    1440
gaagaacaga gacaagcaga aagactgcag aggcagctaa agcaagaaag agactactta    1500
gtttcccttc agcatcagcg gcaggagcag aggcctgtgg agaagaagcc actgtaccat    1560
tacaaagaag gaatgagtcc tagtgagaag ccagcatggg ccaaggaggt agaagaacgg    1620
tcaaggctca accggcaaag ttcccctgcc atgcctcaca aggttgccaa caggatatct    1680
gacccccaacc tgcccccaag gtcggagtcc ttcagcatta gtggagttca gcctgctcga    1740
acaccccca tgctcagacc agtcgatccc cagatcccac atctggtagc tgtaaaatcc    1800
cagggacctg ccttgaccgc ctcccagtca gtgcacgagc agcccacaaa gggcctctct    1860
gggtttcagg aggctctgaa cgtgacctcc caccgcgtgg agatgccacg ccagaactca    1920
gatcccacct cggaaaatcc tcctctcccc actcgcattg aaaagtttga ccgaagctct    1980
tggttacgac aggaagaaga cattccacca aggtgcctc aaagaacaac ttctatatcc    2040
ccagcattag ccagaaagaa ttctcctggg aatggtagtg ctctgggacc cagactagga    2100
tctcaaccca tcagagcaag caaccctgat ctccggagaa ctgagcccat cttggagagc    2160
cccttgcaga ggaccagcag tggcagttcc tccagctcca gcaccctag ctcccagccc    2220
agctcccaag gaggctccca gcctggatca caagcaggat ccagtgaacg caccagagtt    2280
cgagccaaca gtaagtcaga aggatcacct gtgcttcccc atgagcctgc caaggtgaaa    2340
ccagaagaat ccagggacat tacccggccc agtcgaccag ctagctacaa aaaagctata    2400
gatgaggatc tgacggcatt agccaaagaa ctaagagaac tccggattga agaaacaaac    2460
cgcccaatga agaaggtgac tgattactcc tcctccagtg aggagtcaga agtagcgag    2520
gaagaggagg aagatggaga gagcgagacc catgatggga cagtggctgt cagcgacata    2580
cccagactga taccaacagg agctccaggc agcaacgagc agtacaatgt gggaatggtg    2640
gggacgcatg ggctggagac ctctcatgcg gacagtttca gcggcagtat ttcaagagaa    2700
ggaaccttga tgattagaga gacgtctgga gagaagaagc gatctggcca cagtgacagc    2760
aatggctttg ctggccacat caacctccct gacctggtgc agcagagcca ttctccagct    2820
ggaaccccga ctgagggact ggggcgcgtc tcaacccatt cccaggagat ggactctggg    2880
actgaatatg gcatggggag cagcaccaaa gcctccttca ccccctttgt ggaccccaga    2940
gtataccaga cgtctcccac tgatgaagat gaagaggatg aggaatcatc agccgcagct    3000
ctgtttacta gcgaacttct taggcaagaa caggccaaac tcaatgaagc aagaaagatt    3060
tcggtggtaa atgtaaaccc aaccaacatt cggcctcata cgacacacc agaaatcaga    3120
aaatacaaga aacgattcaa ctcagaaata ctttgtgcag ctctgtgggg tgtaaacctt    3180
ctggtgggga ctgaaaatgg cctgatgctt ttggaccgaa gtgggcaagg caaagtctat    3240
aatctgatca accggaggcg atttcagcag atggatgtgc tagagggact gaatgtcctt    3300
gtgacaattt caggaaagaa gaataagcta cgagttttact atcttttcatg gttaagaaac    3360
agaatactac ataatgaccc agaagtagaa aagaaacaag gctggatcac tgttggggac    3420
ttggaaggct gtatacatta taagttgtt aaatatgaaa ggatcaaatt tttggtgatt    3480
```

-continued

| | | |
|---|---|---|
| gccttaaaga atgctgtgga aatatatgct tgggctccta aaccgtatca taaattcatg | 3540 | |
| gcatttaagt cttttgcaga tctccagcac aagcctctgc tagttgatct cacggtagaa | 3600 | |
| gaaggtcaaa gattaaaggt tatttttggt tcacacactg gtttccatgt aattgatgtt | 3660 | |
| gattcaggaa actctatga tatctacata ccatctcata ttcagggcaa tatcactcct | 3720 | |
| catgctattg tcatcttgcc taaaacagat ggaatggaaa tgcttgtttg ctatgaggat | 3780 | |
| gaggggggtgt atgtaaacac ctatggccgg ataactaagg atgtggtgct ccaatgggga | 3840 | |
| gaaatgccca cgtctgtggc ctacattcat tccaatcaga taatgggctg gggcgagaaa | 3900 | |
| gctattgaga tccggtcagt ggaaacagga catttggatg gagtatttat gcataagcga | 3960 | |
| gctcaaaggt taaagtttct atgtgaaaga atgataagg tatttttgc atccgtgcga | 4020 | |
| tctggaggaa gtagccaagt gttttttcatg accctcaaca gaaattccat gatgaactgg | 4080 | |
| taa | 4083 | |

<210> SEQ ID NO 2
<211> LENGTH: 3996
<212> TYPE: DNA
<213> ORGANISM: Artificial sequence
<220> FEATURE:
<223> OTHER INFORMATION: synthetic

<400> SEQUENCE: 2

| | | |
|---|---|---|
| atggcgagcg actccccggc tcgaagcctg gatgaaatag atctctcggc tctgagggac | 60 | |
| cctgcaggga tctttgaatt ggtggaactt gttggaaatg aacatacgg gcaagtttat | 120 | |
| aagggtcgtc atgtcaaaac gggccagctt gcagccatca aggttatgga tgtcacaggg | 180 | |
| gatgaagagg aagaaatcaa acaagaaatt aacatgttga gaaatattc tcatcaccgg | 240 | |
| aatattgcta catactatgg tgcttttatc aaaaagaacc caccaggcat ggatgaccaa | 300 | |
| cttttggttgg tgatggagtt tgtggtgct ggctctgtca ccgacctgat caagaacaca | 360 | |
| aaaggtaaca cgttgaaaga gggagtggat gcatacatct gcagggaaat cttacggggg | 420 | |
| ctgagtcacc tgcaccagca taaagtgatt catcgagata ttaaagggca aaatgtcttg | 480 | |
| ctgactgaaa atgcagaagt taaactagtg gactttggag tcagtgctca gcttgatcga | 540 | |
| acagtgggca ggaggaatac tttcattgga actccctact ggatggcacc agaagttatt | 600 | |
| gcctgtgatg aaaacccaga tgccacatat gatttcaaga gtgacttgtg gtctttgggt | 660 | |
| atcaccgcca ttgaaatggc agaaggtgct ccccctctct gtgacatgca ccccatgaga | 720 | |
| gctctcttcc tcatccccg gaatccagcc cctcggctga agtctaagaa gtggtcaaaa | 780 | |
| aaattccagt catttattga gagctgcttg gtaaagaatc acagccagcg accagcaaca | 840 | |
| gaacaattga tgaagcatcc atttatacga gaccaaccta tgagcgaca ggtccgcatt | 900 | |
| caactcaagg accatattga tagaacaaag aagaagcgag gagaaaaaga tgagacagag | 960 | |
| tatgagtaca gtggaagtga ggaagaagag gaggagaatg actcaggaga gcccagctcc | 1020 | |
| atcctgaatc tgccagggga gtcgacgctg cggagggact ttctgaggct gcagctggcc | 1080 | |
| aacaaggagc gttctgaggc cctacggagg cagcagctgg agcagcagca gcgggagaat | 1140 | |
| gaggagcaca agcggcagct gctggccgag cgtcagaagc gatcgaggga gcagaaagag | 1200 | |
| cagaggcggc ggctggagga gcaacaaagg cgagagaagg agctgcggaa gcagcaggag | 1260 | |
| agggagcagc gccggcacta tgaggagcag atgcgccggg aggaggagag gaggcgtgcg | 1320 | |
| gagcatgaac aggaatataa gcgcaaacaa ttggaagaac agagacaagc agaaagactg | 1380 | |

-continued

```
cagaggcagc taaagcaaga aagagactac ttagtttccc ttcagcatca gcggcaggag    1440
cagaggcctg tggagaagaa gccactgtac cattacaaag aaggaatgag tcctagtgag    1500
aagccagcat gggccaagga ggtagaagaa cggtcaaggc tcaaccggca aagttcccct    1560
gccatgcctc acaaggttgc aacaggata  tctgacccca acctgccccc aaggtcggag    1620
tccttcagca ttagtggagt tcagcctgct cgaacacccc ccatgctcag accagtcgat    1680
ccccagatcc cacatctggt agctgtaaaa tcccagggac ctgccttgac cgcctcccag    1740
tcagtgcacg agcagcccac aaagggcctc tctgggtttc aggaggctct gaacgtgacc    1800
tcccaccgcg tggagatgcc acgccagaac tcagatccca cctcggaaaa tcctcctctc    1860
cccactcgca ttgaaaagtt tgaccgaagc tcttggttac gacaggaaga agacattcca    1920
ccaaaggtgc ctcaaagaac aacttctata tccccagcat tagccagaaa gaattctcct    1980
gggaatggta gtgctctggg acccagacta ggatctcaac ccatcagagc aagcaaccct    2040
gatctccgga gaactgagcc catcttggag agcccctcgc agaggaccag cagtggcagt    2100
tcctccagct ccagcacccc tagctcccag cccagctccc aaggaggctc ccagcctgga    2160
tcacaagcag gatccagtga acgcaccaga gttcgagcca acagtaagtc agaaggatca    2220
cctgtgcttc cccatgagcc tgccaaggtg aaaccagaag aatccaggga cattacccgg    2280
cccagtcgac cagctagcta caaaaaagct atagatgagg atctgacggc attagccaaa    2340
gaactaagag aactccggat tgaagaaaca aaccgcccaa tgaagaaggt gactgattac    2400
tcctcctcca gtgaggagtc agaaagtagc gaggaagagg aggaagatgg agagagcgag    2460
acccatgatg ggacagtggc tgtcagcgac atacccagac tgataccaac aggagctcca    2520
ggcagcaacg agcagtacaa tgtgggaatg gtggggacgc atgggctgga gacctctcat    2580
gcggacagtt tcagcggcag tatttcaaga gaaggaacct tgatgattag agagacgtct    2640
ggagagaaga agcgatctgg ccacagtgac agcaatggct tgctggcca catcaacctc    2700 cctgacctgg tgcagcagag ccattctcca gctggaaccc cgactgaggg actggggcgc    2760
gtctcaaccc attcccagga gatggactct gggactgaat atggcatggg gagcagcacc    2820
aaagcctcct tcaccccctt tgtggacccc agagtatacc agacgtctcc cactgatgaa    2880
gatgaagagg atgaggaatc atcagccgca gctctgttta ctagcgaact tcttaggcaa    2940
gaacaggcca aactcaatga agcaagaaag atttcggtgg taaatgtaaa cccaaccaac    3000
attcggcctc atagcgacac accagaaatc agaaaataca agaaacgatt caactcagaa    3060
atactttgtg cagctctgtg gggtgtaaac cttctggtgg ggactgaaaa tggcctgatg    3120
cttttggacc gaagtgggca aggcaaagtc tataatctga tcaaccggag gcgatttcag    3180
cagatggatg tgctagaggg actgaatgtc cttgtgacaa tttcaggaaa gaagaataag    3240
ctacgagttt actatctttc atggttaaga aacagaatac tacataatga cccgaagta   3300 gaaaagaaac aaggctggat cactgttggg gacttggaag gctgtataca ttataaagtt    3360
gttaaatatg aaaggatcaa attttggtg  attgccttaa agaatgctgt ggaaatatat    3420
gcttgggctc ctaaaccgta tcataaattc atggcattta agtcttttgc agatctccag    3480
cacaagcctc tgctagttga tctcacggta gaagaaggtc aaagattaaa ggttattttt    3540
ggttcacaca ctggtttcca tgtaattgat gttgattcag gaaactctta tgatatctac    3600
ataccatctc atattcaggg caatatcact cctcatgcta ttgtcatctt gcctaaaaca    3660
gatggaatgg aaatgcttgt ttgctatgag gatgaggggg tgtatgtaaa cacctatggc    3720
cggataacta aggatgtggt gctccaatgg ggagaaatgc ccacgtctgt ggcctacatt    3780
```

| | |
|---|---|
| cattccaatc agataatggg ctggggcgag aaagctattg agatccggtc agtggaaaca | 3840 |
| ggacatttgg atggagtatt tatgcataag cgagctcaaa ggttaaagtt tctatgtgaa | 3900 |
| agaaatgata aggtattttt tgcatccgtg cgatctggag gaagtagcca agtgtttttc | 3960 |
| atgaccctca acagaaattc catgatgaac tggtaa | 3996 |

<210> SEQ ID NO 3
<211> LENGTH: 3918
<212> TYPE: DNA
<213> ORGANISM: Artificial sequence
<220> FEATURE:
<223> OTHER INFORMATION: synthetic

<400> SEQUENCE: 3

| | |
|---|---|
| atggcgagcg actccccggc tcgaagcctg gatgaaatag atctctcggc tctgagggac | 60 |
| cctgcaggga tctttgaatt ggtggaactt gttggaaatg gaacatacgg caagttttat | 120 |
| aagggtcgtc atgtcaaaac gggccagctt gcagccatca aggttatgga tgtcacaggg | 180 |
| gatgaagagg aagaaatcaa acaagaaatt aacatgttga agaaatattc tcatcaccgg | 240 |
| aatattgcta catactatgg tgcttttatc aaaaagaacc caccaggcat ggatgaccaa | 300 |
| cttttggttgg tgatggagtt tgtggtgct ggctctgtca ccgacctgat caagaacaca | 360 |
| aaaggtaaca cgttgaaaga ggagtggatt gcatacatct gcagggaaat cttacggggg | 420 |
| ctgagtcacc tgcaccagca taagtgatt catcgagata ttaaagggca aaatgtcttg | 480 |
| ctgactgaaa atgcagaagt taaactagtg gactttggag tcagtgctca gcttgatcga | 540 |
| acagtgggca ggaggaatac tttcattgga actccctact ggatggcacc agaagttatt | 600 |
| gcctgtgatg aaaacccaga tgccacatat gatttcaaga gtgacttgtg gtctttgggt | 660 |
| atcaccgcca ttgaaatggc agaaggtgct ccccctctct gtgacatgca ccccatgaga | 720 |
| gctctcttcc tcatcccccg gaatccagcg cctcggctga agtctaagaa gtggtcaaaa | 780 |
| aaattccagt catttattga gagctgcttt gtaaagaatc acagccagcg accagcaaca | 840 |
| gaacaattga tgaagcatcc atttatacga gaccaaccta tgagcgaca ggtccgcatt | 900 |
| caactcaagg accatattga tagaacaaag aagaagcgag gagaaaaaga tgagacagag | 960 |
| tatgagtaca gtggaagtga ggaagaagag gaggagaatg actcaggaga gcccagctcc | 1020 |
| atcctgaatc tgccagggga gtcgacgctg cggagggact ttctgaggct gcagctggcc | 1080 |
| aacaaggagc gttctgaggc cctacggagg cagcagctgg agcagcagca gcgggagaat | 1140 |
| gaggagcaca gcggcagct gctggccgag cgtcagaagc gcatcgagga gcagaaagag | 1200 |
| cagaggcggc ggctggagga gcaacaaagg cgagagaagg agctgcggaa gcagcaggag | 1260 |
| agggagcagc gccggcacta tgaggagcag atgcgccggg aggaggagag gaggcgtgcg | 1320 |
| gagcatgaac aggaatacat caggcgacag ttagaggagg agcagagaca gttagagatc | 1380 |
| ttgcagcagc agctactgca tgaacaagct ctacttctgg aatataagcg caaacaattg | 1440 |
| gaagaacaga gacaagcaga aagactgcag aggcagctaa agcaagaaag agactactta | 1500 |
| gtttccttc agcatcagcg gcaggagcag aggcctgtgg agaagaagcc actgtaccat | 1560 |
| tacaaagaag gaatgagtcc tagtgagaag ccagcatggg ccaaggagat cccacatctg | 1620 |
| gtagctgtaa atcccaggg acctgccttg accgcctccc agtcagtgca cgagcagccc | 1680 |
| acaaaggggc tctctgggtt tcaggaggct ctgaacgtga cctcccaccg cgtggagatg | 1740 |
| ccacgccaga actcagatcc cacctcggaa aatcctcctc tccccactcg cattgaaaag | 1800 |

-continued

```
tttgaccgaa gctcttggtt acgacaggaa gaagacattc caccaaaggt gcctcaaaga      1860
acaacttcta tatccccagc attagccaga aagaattctc ctgggaatgg tagtgctctg      1920
ggacccagac taggatctca acccatcaga gcaagcaacc ctgatctccg agaactgag       1980 cccatcttgg agagcccctt gcagaggacc agcagtggca gttcctccag ctccagcacc      2040
cctagctccc agcccagctc caaggaggc tcccagcctg gatcacaagc aggatccagt       2100
gaacgcacca gagttcgagc aacagtaag tcagaaggat cacctgtgct tccccatgag       2160
cctgccaagg tgaaaccaga agaatccagg gacattaccc ggcccagtcg accagctagc      2220
tacaaaaaag ctatagatga ggatctgacg gcattagcca agaactaag agaactccgg       2280 attgaagaaa caaaccgccc aatgaagaag gtgactgatt actcctcctc cagtgaggag      2340
tcagaaagta gcgaggaaga ggaggaagat ggagagagcg agacccatga tgggacagtg      2400
gctgtcagcg acatacccag actgatacca acaggagctc caggcagcaa cgagcagtac      2460
aatgtgggaa tggtggggac gcatgggctg gagacctctc atgcggacag tttcagcggc      2520
agtatttcaa gagaaggaac cttgatgatt agagagacgt ctggagagaa gaagcgatct      2580
ggccacagtg acagcaatgg ctttgctggc cacatcaacc tccctgacct ggtgcagcag      2640
agccattctc cagctggaac cccgactgag ggactggggc gcgtctcaac ccattcccag      2700
gagatggact ctgggactga atatggcatg gggagcagca ccaaagcctc cttcaccccc      2760
tttgtggacc ccagagtata ccagacgtct cccactgatg aagatgaaga ggatgaggaa      2820
tcatcagccg cagctctgtt tactagcgaa cttcttaggc aagaacaggc caaactcaat      2880
gaagcaagaa agatttcggt ggtaaatgta aacccaacca acattcggcc tcatagcgac      2940
acaccagaaa tcagaaaata caagaaacga ttcaactcag aaatactttg tgcagctctg      3000 tgggtgtaa accttctggt ggggactgaa aatggcctga tgcttttgga ccgaagtggg      3060
caaggcaaag tctataatct gatcaaccgg aggcgatttc agcagatgga tgtgctagag      3120
ggactgaatg tccttgtgac aatttcagga aagaagaata agctacgagt ttactatctt      3180
tcatggttaa gaaacagaat actacataat gacccagaag tagaaaagaa acaaggctgg      3240
atcactgttg gggacttgga aggctgtata cattataaag ttgttaaata tgaaaggatc      3300 aaattttttgg tgattgcctt aaagaatgct gtggaaatat atgcttgggc tcctaaaccg      3360
tatcataaat tcatggcatt taagtctttt gcagatctcc agcacaagcc tctgctagtt      3420
gatctcacgg tagaagaagg tcaaagatta aaggttattt ttggttcaca cactggtttc      3480
catgtaattg atgttgattc aggaaactct tatgatatct acataccatc tcatattcag      3540
ggcaatatca ctcctcatgc tattgtcatc ttgcctaaaa cagatggaat ggaaatgctt      3600
gtttgctatg aggatgaggg ggtgtatgta aacacctatg gccggataac taaggatgtg      3660
gtgctccaat ggggagaaat gcccacgtct gtggcctaca ttcattccaa tcagataatg      3720
ggctggggcg agaaagctat tgagatccgg tcagtggaaa caggacattt ggatggagta      3780
tttatgcata agcgagctca aaggttaaag tttctatgtg aaagaaatga taggtatttt      3840
tttgcatccg tgcgatctgg aggaagtagc caagtgtttt tcatgaccct caacagaaat      3900
tccatgatga actggtaa                                                    3918
```

<210> SEQ ID NO 4
<211> LENGTH: 4059
<212> TYPE: DNA
<213> ORGANISM: Artificial sequence
<220> FEATURE:
<223> OTHER INFORMATION: synthetic -continued

<400> SEQUENCE: 4

```
atggcgagcg actccccggc tcgaagcctg gatgaaatag atctctcggc tctgagggac      60
cctgcaggga tctttgaatt ggtggaactt gttggaaatg aacatacgg gcaagtttat      120
aagggtcgtc atgtcaaaac gggccagctt gcagccatca aggttatgga tgtcacaggg     180
gatgaagagg aagaaatcaa acaagaaatt aacatgttga gaaatattc tcatcaccgg     240
aatattgcta catactatgg tgcttttatc aaaaagaacc caccaggcat ggatgaccaa     300
ctttggttgg tgatggagtt ttgtggtgct ggctctgtca ccgacctgat caagaacaca     360
aaaggtaaca cgttgaaaga ggagtggatt gcatacatct gcagggaaat cttacggggg     420
ctgagtcacc tgcaccagca taagtgatt catcgagata ttaaagggca aaatgtcttg      480
ctgactgaaa atgcagaagt taaactagtg gactttggag tcagtgctca gcttgatcga    540
acagtgggca ggaggaatac tttcattgga actccctact ggatggcacc agaagttatt    600
gcctgtgatg aaacccaga tgccacatat gatttcaaga gtgacttgtg gtctttgggt    660
atcaccgcca ttgaaatggc agaaggtgct ccccctctct gtgacatgca ccccatgaga    720
gctctcttcc tcatccccg gaatccagcg cctcggctga agtctaagaa gtggtcaaaa     780
aaattccagt catttattga gagctgcttg gtaaagaatc acagccagcg accagcaaca    840
gaacaattga tgaagcatcc atttatacga gaccaaccta atgagcgaca ggtccgcatt    900
caactcaagg accatattga tagaacaaag aagaagcgag gagaaaaaga tgagacagag    960
tatgagtaca gtggaagtga ggaagaagag gaggagaatg actcaggaga gcccagctcc   1020
atcctgaatc tgccagggga gtcgacgctg cggagggact ttctgaggct gcagctggcc   1080
aacaaggagc gttctgaggc cctacggagg cagcagctga gcagcagca gcgggagaat   1140
gaggagcaca gcggcagct gctggccgag cgtcagaagc gcatcgagga gcagaaagag   1200
cagaggcggc ggctggagga gcaacaaagg cgagagaagg agctgcggaa gcagcaggag  1260
agggagcagc gccggcacta tgaggagcag atgcgccggg aggaggagag gaggcgtgcg  1320
gagcatgaac aggaatacat caggcgacag ttagaggagg agcagagaca gttagagatc  1380
ttgcagcagc agctactgca tgaacaagct ctacttctgg aatataagcg caaacaattg  1440
gaagaacaga gacaagcaga aagactgcag aggcagctaa agcaagaaag agactactta  1500
gtttcccttc agcatcagcg gcaggagcag aggcctgtgg agaagaagcc actgtaccat  1560
tacaaagaag gaatgagtcc tagtgagaag ccagcatggg ccaaggaggt agaagaacgg  1620
tcaaggctca accggcaaag ttcccctgcc atgcctcaca aggttgccaa caggatatct  1680
gaccccaacc tgcccccaag gtcggagtcc ttcagcatta gtggagttca gcctgctcga  1740
acaccccca tgctcagacc agtcgatccc cagatcccac atctggtagc tgtaaaatcc   1800
cagggacctg ccttgaccgc ctcccagtca gtgcacgagc agcccacaaa gggctctctc  1860
gggtttcagg aggctctgaa cgtgacctcc caccgcgtgg agatgccacg ccagaactca  1920
gatcccacct cggaaaatcc tcctctcccc actcgcattg aaaagtttga ccgaagctct   1980
tggttacgac aggaagaaga cattccacca aggtgcctc aaagaacaac ttctatatcc   2040
ccagcattag ccagaaagaa ttctcctggg aatggtagtg ctctgggacc agactagga   2100
tctcaaccca tcagagcaag caaccctgat ctccggagaa ctgagcccat cttggagagc   2160
cccttgcaga ggaccagcag tggcagttcc tccagctcca gcaccctag ctcccagccc   2220
agctcccaag gaggctccca gcctggatca caagcaggat ccagtgaacg caccagagtt  2280
```

```
cgagccaaca gtaagtcaga aggatcacct gtgcttcccc atgagcctgc caaggtgaaa    2340
ccagaagaat ccagggacat tacccggccc agtcgaccag ctgatctgac ggcattagcc    2400
aaagaactaa gagaactccg gattgaagaa acaaaccgcc caatgaagaa ggtgactgat    2460
tactcctcct ccagtgagga gtcagaaagt agcgaggaag aggaggaaga tggagagagc    2520
gagacccatg atgggacagt ggctgtcagc gacatacccca gactgatacc aacaggagct    2580
ccaggcagca acgagcagta caatgtggga atggtgggga cgcatgggct ggagacctct    2640
catgcggaca gtttcagcgg cagtatttca agagaaggaa ccttgatgat tagagagacg    2700
tctggagaga agaagcgatc tggccacagt gacagcaatg gctttgctgg ccacatcaac    2760
ctccctgacc tggtgcagca gagccattct ccagctggaa ccccgactga gggactgggg    2820
cgcgtctcaa cccattccca ggagatggac tctgggactg aatatggcat ggggagcagc    2880
accaaagcct ccttcacccc ctttgtggac cccagagtat accagacgtc tcccactgat    2940
gaagatgaag aggatgagga atcatcagcc gcagctctgt ttactagcga acttcttagg    3000
caagaacagg ccaaactcaa tgaagcaaga aagatttcgg tggtaaatgt aaacccaacc    3060
aacattcggc ctcatagcga cacaccagaa atcagaaaat acaagaaacg attcaactca    3120
gaaatacttt gtgcagctct gtggggtgta aaccttctgg tggggactga aaatggcctg    3180
atgcttttgg accgaagtgg gcaaggcaaa gtctataatc tgatcaaccg gaggcgattt    3240
cagcagatgg atgtgctaga gggactgaat gtccttgtga caatttcagg aaagaagaat    3300
aagctacgag tttactatct ttcatggtta agaaacagaa tactacataa tgacccagaa    3360
gtagaaaaga acaaggctg gatcactgtt ggggacttgg aaggctgtat acattataaa    3420
gttgttaaat atgaaaggat caaattttttg gtgattgcct taaagaatgc tgtggaaata    3480
tatgcttggg ctcctaaacc gtatcataaa ttcatggcat ttaagtcttt tgcagatctc    3540
cagcacaagc ctctgctagt tgatctcacg gtagaagaag gtcaaagatt aaaggttatt    3600
tttggttcac acactggttt ccatgtaatt gatgttgatt caggaaactc ttatgatatc    3660
tacataccat ctcatattca gggcaatatc actcctcatg ctattgtcat cttgcctaaa    3720
acagatggaa tggaaatgct tgtttgctat gaggatgagg gggtgtatgt aaacacctat    3780
ggccggataa ctaaggatgt ggtgctccaa tggggagaaa tgcccacgtc tgtggcctac    3840
attcattcca atcagataat gggctggggc gagaaagcta ttgagatccg gtcagtggaa    3900
acaggacatt tggatggagt atttatgcat aagcgagctc aaaggttaaa gtttctatgt    3960
gaaagaaatg ataaggtatt ttttgcatcc gtgcgatctg gaggaagtag ccaagtgttt    4020
ttcatgaccc tcaacagaaa ttccatgatg aactggtaa                           4059
```

<210> SEQ ID NO 5
<211> LENGTH: 3831
<212> TYPE: DNA
<213> ORGANISM: Artificial sequence
<220> FEATURE:
<223> OTHER INFORMATION: synthetic

<400> SEQUENCE: 5

```
atggcgagcg actccccggc tcgaagcctg gatgaaatag atctctcggc tctgagggac      60
cctgcaggga tctttgaatt ggtggaactt gttggaaatg gaacatacgg gcaagtttat     120
aagggtcgtc atgtcaaaac gggccagctt gcagccatca aggttatgga tgtcacaggg     180
gatgaagagg aagaaatcaa acaagaaatt aacatgttga agaaatattc tcatcaccgg     240
aatattgcta catactatgg tgctttatc aaaaagaacc caccaggcat ggatgaccaa     300
```

-continued

```
ctttggttgg tgatggagtt ttgtggtgct ggctctgtca ccgacctgat caagaacaca    360
aaaggtaaca cgttgaaaga ggagtggatt gcatacatct gcagggaaat cttacgggg     420
ctgagtcacc tgcaccagca taaagtgatt catcgagata ttaaagggca aaatgtcttg    480
ctgactgaaa atgcagaagt taaactagtg gactttggag tcagtgctca gcttgatcga    540
acagtgggca ggaggaatac tttcattgga actccctact ggatggcacc agaagttatt    600
gcctgtgatg aaacccaga tgccacatat gatttcaaga gtgacttgtg gtctttgggt     660
atcaccgcca ttgaaatggc agaaggtgct ccccctctct gtgacatgca ccccatgaga    720
gctctcttcc tcatccccg gaatccagcg cctcggctga agtctaagaa gtggtcaaaa     780
aaattccagt catttattga gagctgcttg gtaaagaatc acagccagcg accagcaaca    840
gaacaattga tgaagcatcc atttatacga gaccaaccta atgagcgaca ggtccgcatt    900
caactcaagg accatattga tagaacaaag aagaagcgag gagaaaaaga tgagacagag    960
tatgagtaca gtggaagtga ggaagaagag gaggagaatg actcaggaga gcccagctcc   1020
atcctgaatc tgccagggga gtcgacgctg cggagggact ttctgaggct gcagctggcc   1080
aacaaggagc gttctgaggc cctacggagg cagcagctgg agcagcagca gcgggagaat   1140
gaggagcaca agcggcagct gctggccgag cgtcagaagc gcatcgagga gcagaaagag   1200
cagaggcggc ggctggagga gcaacaaagg cgagagaagg agctgcggaa gcagcaggag   1260
agggagcagc gccggcacta tgaggagcag atgcgccggg aggaggagag gaggcgtgcg   1320
gagcatgaac aggaatataa gcgcaaacaa ttggaagaac agagacaagc agaaagactg   1380
cagaggcagc taaagcaaga aagagactac ttagtttccc ttcagcatca gcggcaggag   1440
cagaggcctg tggagaagaa gccactgtac cattacaaag aaggaatgag tcctagtgag   1500
aagccagcat gggccaagga gatcccacat ctggtagctg taaatcccca gggacctgcc   1560
ttgaccgcct cccagtcagt gcacgagcag cccacaaagg gcctctctgg gtttcaggag   1620
gctctgaacg tgacctccca ccgcgtggag atgccacgcc agaactcaga tcccacctcg   1680
gaaaatcctc ctctccccac tcgcattgaa aagtttgacc gaagctcttg gttacgacag   1740
gaagaagaca ttccaccaaa ggtgcctcaa agaacaactt ctatatcccc agcattagcc   1800
agaaagaatt ctcctgggaa tggtagtgct ctgggaccca gactaggatc tcaacccatc   1860
agagcaagca accctgatct ccggagaact gagcccatct tggagagccc cttgcagagg   1920
accagcagtg gcagttcctc cagctccagc accccatagct cccagcccag ctcccaagga   1980
ggctcccagc ctggatcaca agcaggatcc agtgaacgca ccagagttcg agccaacagt   2040
aagtcagaag gatcacctgt gcttccccat gagcctgcca aggtgaaacc agaagaatcc   2100
agggacatta cccggcccag tcgaccagct agctacaaaa aagctataga tgaggatctg   2160
acggcattag ccaaagaact aagagaactc cggattgaag aaacaaaccg cccaatgaag   2220
aaggtgactg attactcctc ctccagtgag gagtcagaaa gtagcgagga agaggaggaa   2280
gatggagaga gcgagaccca tgatgggaca gtggctgtca gcgacatacc cagactgata   2340
ccaacaggag ctccaggcag caacgagcag tacaatgtgg aatggtggg gacgcatggg    2400
ctggagacct ctcatgcgga cagtttcagc ggcagtattt caagagaagg aaccttgatg   2460
attagagaga cgtctggaga agaagcgag tctggccaca gtgacagcaa tggctttgct    2520
ggccacatca acctccctga cctggtgcag cagagccatt ctccagctgg aaccccgact   2580
gagggactgg ggcgcgtctc aacccattcc caggagatgg actctgggac tgaatatggc   2640
```

-continued

```
atggggagca gcaccaaagc ctccttcacc cccttgtgg accccagagt ataccagacg    2700
tctcccactg atgaagatga agaggatgag gaatcatcag ccgcagctct gtttactagc    2760
gaacttctta ggcaagaaca ggccaaactc aatgaagcaa aaagatttc ggtggtaaat     2820 gtaaacccaa ccaacattcg gcctcatagc gacacaccag aaatcagaaa atacaagaaa    2880
cgattcaact cagaaatact ttgtgcagct ctgtggggtg taaaccttct ggtggggact    2940
gaaaatggcc tgatgctttt ggaccgaagt gggcaaggca aagtctataa tctgatcaac    3000
cggaggcgat tcagcagat ggatgtgcta gagggactga atgtccttgt gacaatttca     3060
ggaaagaaga ataagctacg agtttactat ctttcatggt taagaaacag aatactacat    3120
aatgacccag aagtagaaaa gaaacaaggc tggatcactg ttggggactt ggaaggctgt    3180
atacattata aagttgttaa atatgaaagg atcaaatttt tggtgattgc cttaaagaat    3240
gctgtggaaa tatatgcttg ggctcctaaa ccgtatcata aattcatggc atttaagtct    3300
tttgcagatc tccagcacaa gcctctgcta gttgatctca cggtagaaga aggtcaaaga    3360 ttaaggtta tttttggttc acacactggt ttccatgtaa ttgatgttga ttcaggaaac     3420
tcttatgata tctacatacc atctcatatt caggcaata tcactcctca tgctattgtc     3480
atcttgccta aaacagatgg aatgaaaatg cttgtttgct atgaggatga ggggtgtat     3540 gtaaacacct atggccggat aactaaggat gtggtgctcc aatggggaga atgcccacg     3600 tctgtggcct acattcattc caatcagata atgggctggg gcgagaaagc tattgagatc    3660
cggtcagtgg aaacaggaca tttggatgga gtatttatgc ataagcgagc tcaaaggtta    3720
aagtttctat gtgaaagaaa tgataaggta tttttttgcat ccgtgcgatc tggaggaagt    3780
agccaagtgt ttttcatgac cctcaacaga aattccatga tgaactggta a             3831
```

<210> SEQ ID NO 6
<211> LENGTH: 3972
<212> TYPE: DNA
<213> ORGANISM: Artificial sequence
<220> FEATURE:
<223> OTHER INFORMATION: synthetic

<400> SEQUENCE: 6

```
atggcgagcg actccccggc tcgaagcctg gatgaaatag atctctcggc tctgagggac     60
cctgcaggga tctttgaatt ggtggaactt gttggaaatg gaacatacgg gcaagtttat    120
aagggtcgtc atgtcaaaac gggccagctt gcagccatca aggttatgga tgtcacaggg    180
gatgaagagg aagaaatcaa acaagaaatt aacatgttga gaaatattc tcatcaccgg    240 aatattgcta catactatgg tgcttttatc aaaaagaacc caccaggcat ggatgaccaa    300
ctttggttgg tgatggagtt ttgtggtgct ggctctgtca ccgacctgat caagaacaca    360
aaaggtaaca cgttgaaaga ggagtggatt gcatacatct gcagggaaat cttacgggg     420 ctgagtcacc tgcaccagca taagtgatt catcgagata ttaaagggca aaatgtcttg    480
ctgactgaaa atgcagaagt taaactagtg actttggag tcagtgctca gcttgatcga     540
acagtgggca ggaggaatac tttcattgga actccctact ggatggcacc agaagttatt    600
gcctgtgatg aaaacccaga tgccacatat gatttcaaga gtgacttgtg gtctttgggt    660
atcaccgcca ttgaaatggc agaaggtgct ccccctctct gtgacatgca ccccatgaga    720
gctctcttcc tcatccccg gaatccagcc ctcggctga agtctaagaa gtggtcaaaa      780
aaattccagt catttattga gagctgcttg gtaaagaatc acagccagcg accagcaaca    840
gaacaattga tgaagcatcc atttatacga gaccaaccta atgagcgaca ggtccgcatt    900
```

```
caactcaagg accatattga tagaacaaag aagaagcgag gagaaaaaga tgagacagag      960
tatgagtaca gtggaagtga ggaagaagag gaggagaatg actcaggaga gcccagctcc     1020
atcctgaatc tgccagggga gtcgacgctg cggagggact ttctgaggct gcagctggcc     1080
aacaaggagc gttctgaggc cctacggagg cagcagctgg agcagcagca gcggagaat     1140
gaggagcaca agcggcagct gctggccgag cgtcagaagc gcatcgagga gcagaaagag     1200
cagaggcggc ggctggagga gcaacaaagg cgagagaagg agctgcggaa gcagcaggag     1260
agggagcagc gccggcacta tgaggagcag atgcgccggg aggaggagag gaggcgtgcg     1320
gagcatgaac aggaatataa agcgcaaaca ttggaagaac agagacaagc agaaagactg     1380
cagaggcagc taaagcaaga aagagactac ttagtttccc ttcagcatca gcggcaggag     1440
cagaggcctg tggagaagaa gccactgtac cattacaaag aaggaatgag tcctagtgag     1500
aagccagcat gggccaagga ggtagaagaa cggtcaaggc tcaaccggca aagttcccct     1560
gccatgcctc acaaggttgc caacaggata tctgacccca acctgccccc aaggtcggag     1620
tccttcagca ttagtggagt tcagcctgct cgaacacccc ccatgctcag accagtcgat     1680
ccccagatcc cacatctggt agctgtaaaa tcccagggac ctgccttgac cgcctcccag     1740
tcagtgcacg agcagcccac aaagggcctc tctgggtttc aggaggctct gaacgtgacc     1800
tcccaccgcg tggagatgcc acgccagaac tcagatccca cctcggaaaa tcctcctctc     1860
cccactcgca ttgaaaagtt tgaccgaagc tcttggttac gacaggaaga agacattcca     1920
ccaaaggtgc ctcaaagaac aacttctata tccccagcat tagccagaaa gaattctcct     1980
gggaatggta gtgctctggg acccagacta ggatctcaac ccatcagagc aagcaaccct     2040
gatctccgga gaactgagcc catcttggag agcccttgc agaggaccag cagtggcagt     2100
tcctccagct ccagcacccc tagctcccag cccagctccc aaggaggctc ccagcctgga     2160
tcacaagcag gatccagtga acgcaccaga gttcgagcca acagtaagtc agaaggatca     2220
cctgtgcttc cccatgagcc tgccaaggtg aaaccgaaag aatccaggga cattacccgg     2280
cccagtcgac cagctgatct gacggcatta gccaagaac taagagaact ccggattgaa     2340
gaaacaaacc gcccaatgaa gaaggtgact gattactcct cctccagtga ggagtcagaa     2400
agtagcgagg aagaggagga agatggagag agcgagaccc atgatgggac agtggctgtc     2460
agcgacatac ccagactgat accaacagga gctccaggca gcaacgagca gtacaatgtg     2520
ggaatggtgg ggacgcatgg gctggagacc tctcatgcgg acagtttcag cggcagtatt     2580
tcaagagaag gaaccttgat gattagagag acgtctggag agaagaagcg atctggccac     2640
agtgacagca atggctttgc tggccacatc aacctccctg acctggtgca gcagagccat     2700
tctccagctg gaacccgac tgagggactg gggcgcgtct caacccattc ccaggagatg     2760
gactctggga ctgaatatgg catggggagc agcaccaaag cctccttcac cccctttgtg     2820
gacccccagag tataccagac gtctcccact gatgaagatg aagaggatga ggaatcatca     2880
gccgcagctc tgtttactag cgaacttctt aggcaagaac aggccaaact caatgaagca     2940
agaaagattt cggtggtaaa tgtaaaccca accaacattc ggcctcatag cgacacacca     3000
gaaatcagaa aatacaagaa acgattcaac tcagaaatac tttgtgcagc tctgtggggt     3060
gtaaaccttc tggtggggac tgaaaatggc ctgatgcttt tggaccgaag tgggcaaggc     3120
aaagtctata atctgatcaa ccggaggcga tttcagcaga tggatgtgct agagggactg     3180
aatgtccttg tgacaatttc aggaaagaag aataagctac gagtttacta tctttcatgg     3240
```

-continued

| | |
|---|---|
| ttaagaaaca gaatactaca taatgaccca gaagtagaaa agaaacaagg ctggatcact | 3300 |
| gttggggact tggaaggctg tatacattat aaagttgtta aatatgaaag gatcaaattt | 3360 |
| ttggtgattg ccttaaagaa tgctgtggaa atatatgctt gggctcctaa accgtatcat | 3420 |
| aaattcatgg catttaagtc ttttgcagat ctccagcaca agcctctgct agttgatctc | 3480 |
| acggtagaag aaggtcaaag attaaaggtt attttggtt cacacactgg tttccatgta | 3540 |
| attgatgttg attcaggaaa ctcttatgat atctacatac catctcatat tcagggcaat | 3600 |
| atcactcctc atgctattgt catcttgcct aaaacagatg gaatgaaat gcttgtttgc | 3660 |
| tatgaggatg agggggtgta tgtaaacacc tatggccgga taactaagga tgtggtgctc | 3720 |
| caatggggag aaatgcccac gtctgtggcc tacattcatt ccaatcagat aatgggctgg | 3780 |
| ggcgagaaag ctattgagat ccggtcagtg gaaacaggac atttggatgg agtatttatg | 3840 |
| cataagcgag ctcaaaggtt aaagtttcta tgtgaaagaa atgataaggt atttttgca | 3900 |
| tccgtgcgat ctggaggaag tagccaagtg ttttcatga ccctcaacag aaattccatg | 3960 |
| atgaactggt aa | 3972 |

<210> SEQ ID NO 7
<211> LENGTH: 3894
<212> TYPE: DNA
<213> ORGANISM: Artificial sequence
<220> FEATURE:
<223> OTHER INFORMATION: synthetic

<400> SEQUENCE: 7

| | |
|---|---|
| atggcgagcg actccccggc tcgaagcctg gatgaaatag atctctcggc tctgagggac | 60 |
| cctgcaggga tctttgaatt ggtggaactt gttggaaatg gaacatacgg gcaagtttat | 120 |
| aagggtcgtc atgtcaaaac gggccagctt gcagccatca aggttatgga tgtcacaggg | 180 |
| gatgaagagg aagaaatcaa acaagaaatt aacatgttga gaaatattc tcatcaccgg | 240 |
| aatattgcta catactatgg tgcttttatc aaaaagaacc caccaggcat ggatgaccaa | 300 |
| ctttggttgg tgatggagtt ttgtggtgct ggctctgtca ccgacctgat caagaacaca | 360 |
| aaaggtaaca cgttgaaaga ggagtggatt gcatacatct gcagggaaat cttacggggg | 420 |
| ctgagtcacc tgcaccagca taagtgatt catcgagata ttaaagggca aaatgtcttg | 480 |
| ctgactgaaa atgcagaagt taaactagtg gactttggag tcagtgctca gcttgatcga | 540 |
| acagtgggca ggaggaatac tttcattgga actccctact ggatggcacc agaagttatt | 600 |
| gcctgtgatg aaaacccaga tgccacatat gatttcaaga gtgacttgtg gtctttgggt | 660 |
| atcaccgcca ttgaaatggc agaaggtgct cccctctct gtgacatgca ccccatgaga | 720 |
| gctctcttcc tcatcccccg gaatccagcg cctcggctga agtctaagaa gtggtcaaaa | 780 |
| aaattccagt catttattga gagctgcttg gtaaagaatc acagccagcg accagcaaca | 840 |
| gaacaattga tgaagcatcc atttatacga gaccaaccta atgagcgaca ggtccgcatt | 900 |
| caactcaagg accatattga tagaacaaag aagaagcgag gagaaaaaga tgagacagag | 960 |
| tatgagtaca gtggaagtga ggaagaagag gaggagaatg actcaggaga gcccagctcc | 1020 |
| atcctgaatc tgccagggga gtcgacgctg cggagggact ttctgaggct gcagctggcc | 1080 |
| aacaaggagc gttctgaggc cctacggagg cagcagctga gcagcagca gcgggagaat | 1140 |
| gaggagcaca gcggcagct gctggccgag cgtcagaagc gcatcgagga gcagaaagag | 1200 |
| cagaggcggc ggctggagga gcaacaaagg cgagagaagg agctgcggaa gcagcaggag | 1260 |
| agggagcagc gccggcacta tgaggagcag atgcgccggg aggaggagag gaggcgtgcg | 1320 |

```
gagcatgaac aggaatacat caggcgacag ttagaggagg agcagagaca gttagagatc    1380
ttgcagcagc agctactgca tgaacaagct ctacttctgg aatataagcg caaacaattg    1440
gaagaacaga gacaagcaga aagactgcag aggcagctaa agcaagaaag agactactta    1500
gtttcccttc agcatcagcg gcaggagcag aggcctgtgg agaagaagcc actgtaccat    1560
tacaaagaag gaatgagtcc tagtgagaag ccagcatggg ccaaggagat cccacatctg    1620
gtagctgtaa atcccaggg acctgccttg accgcctccc agtcagtgca cgagcagccc    1680
acaaagggcc tctctgggtt tcaggaggct ctgaacgtga cctcccaccg cgtggagatg    1740
ccacgccaga actcagatcc cacctcggaa aatcctcctc tccccactcg cattgaaaag    1800
tttgaccgaa gctcttggtt acgacaggaa gaagacattc caccaaaggt gcctcaaaga    1860
acaacttcta tatccccagc attagccaga aagaattctc ctgggaatgg tagtgctctg    1920
ggacccagac taggatctca acccatcaga gcaagcaacc ctgatctccg gagaactgag    1980
cccatcttgg agagcccctt gcagaggacc agcagtggca gttcctccag ctccagcacc    2040
cctagctccc agcccagctc ccaaggaggc tcccagcctg gatcacaagc aggatccagt    2100
gaacgcacca gagttcgagc caacagtaag tcagaaggat cacctgtgct tccccatgag    2160
cctgccaagg tgaaaccaga agaatccagg gacattaccc ggcccagtcg accagctgat    2220
ctgacggcat tagccaaaga actaagagaa ctccggattg aagaaacaaa ccgcccaatg    2280
aagaaggtga ctgattactc ctcctccagt gaggagtcag aaagtagcga ggaagaggag    2340
gaagatggag agagcgagac ccatgatggg acagtggctg tcagcgacat acccagactg    2400
ataccaacag gagctccagg cagcaacgag cagtacaatg tgggaatggt ggggacgcat    2460
gggctggaga cctctcatgc ggacagtttc agcggcagta tttcaagaga aggaaccttg    2520
atgattagag agacgtctgg agagaagaag cgatctggcc acagtgacag caatggcttt    2580
gctggccaca tcaacctccc tgacctggtg cagcagagcc attctccagc tggaaccccg    2640
actgagggac tggggcgcgt ctcaacccat tcccaggaga tggactctgg gactgaatat    2700
ggcatgggga gcagcaccaa agcctccttc acccccttg tggaccccag agtataccag    2760
acgtctccca ctgatgaaga tgaagaggat gaggaatcat cagccgcagc tctgtttact    2820
agcgaacttc ttaggcaaga acaggccaaa ctcaatgaag caagaaagat ttcggtggta    2880
aatgtaaacc caaccaacat tcggcctcat agcgacacac cagaaatcag aaaatacaag    2940
aaacgattca actcagaaat actttgtgca gctctgtggg gtgtaaacct tctggtgggg    3000
actgaaaatg gcctgatgct tttggaccga agtgggcaag gcaaagtcta taatctgatc    3060
aaccggaggc gatttcagca gatggatgtg ctagagggac tgaatgtcct tgtgacaatt    3120
tcaggaaaga agaataagct acgagtttac tatctttcat ggttaagaaa cagaatacta    3180
cataatgacc cagaagtaga aaagaaacaa ggctggatca ctgttgggga cttggaaggc    3240
tgtatacatt ataaagttgt taaatatgaa aggatcaaat ttttggtgat tgccttaaag    3300
aatgctgtgg aaatatatgc ttgggctcct aaaccgtatc ataaattcat ggcatttaag    3360
tcttttgcag atctccagca caagcctctg ctagttgatc tcacggtaga agaaggtcaa    3420
agattaaagg ttatttttgg ttcacacact ggtttccatg taattgatgt tgattcagga    3480
aactcttatg atatctacat accatctcat attcaggcga atatcactcc tcatgctatt    3540
gtcatcttgc ctaaaacaga tggaatggaa atgcttgttt gctatgagga tgaggggtg    3600 tatgtaaaca cctatggccg gataactaag gatgtggtgc tccaatgggg agaaatgccc    3660
```

| | |
|---|---|
| acgtctgtgg cctacattca ttccaatcag ataatgggct ggggcgagaa agctattgag | 3720 |
| atccggtcag tggaaacagg acatttggat ggagtattta tgcataagcg agctcaaagg | 3780 |
| ttaaagtttc tatgtgaaag aaatgataag gtattttttg catccgtgcg atctggagga | 3840 |
| agtagccaag tgttttcat gaccctcaac agaaattcca tgatgaactg gtaa | 3894 |

<210> SEQ ID NO 8
<211> LENGTH: 3807
<212> TYPE: DNA
<213> ORGANISM: Artificial sequence
<220> FEATURE:
<223> OTHER INFORMATION: synthetic

<400> SEQUENCE: 8

| | |
|---|---|
| atggcgagcg actccccggc tcgaagcctg gatgaaatag atctctcggc tctgagggac | 60 |
| cctgcaggga tctttgaatt ggtggaactt gttggaaatg aacatacgg gcaagtttat | 120 |
| aagggtcgtc atgtcaaaac gggccagctt gcagccatca aggttatgga tgtcacaggg | 180 |
| gatgaagagg aagaaatcaa acaagaaatt aacatgttga gaaatattc tcatcaccgg | 240 |
| aatattgcta catactatgg tgcttttatc aaaaagaacc caccaggcat ggatgaccaa | 300 |
| ctttggttgg tgatggagtt tgtggtgct ggctctgtca ccgacctgat caagaacaca | 360 |
| aaaggtaaca cgttgaaaga ggagtggatt gcatacatct gcagggaaat cttacggggg | 420 |
| ctgagtcacc tgcaccagca taagtgatt catcgagata ttaaagggca aaatgtcttg | 480 |
| ctgactgaaa atgcagaagt taaactagtg gactttggag tcagtgctca gcttgatcga | 540 |
| acagtgggca ggaggaatac tttcattgga actccctact ggatggcacc agaagttatt | 600 |
| gcctgtgatg aaaacccaga tgccacatat gatttcaaga gtgacttgtg gtctttgggt | 660 |
| atcaccgcca ttgaaatggc agaaggtgct ccccctctct gtgacatgca ccccatgaga | 720 |
| gctctcttcc tcatccccg gaatccagcc ctcggctga agtctaagaa gtggtcaaaa | 780 |
| aaattccagt catttattga gagctgcttg gtaaagaatc acagccagcg accagcaaca | 840 |
| gaacaattga tgaagcatcc atttatacga gaccaaccta tgagcgaca ggtccgcatt | 900 |
| caactcaagg accatattga tagaacaaag aagaagcgag agaaaaaga tgagacagag | 960 |
| tatgagtaca gtgaagtga ggaagaagag gaggagaatg actcaggaga gcccagctcc | 1020 |
| atcctgaatc tgccagggga gtcgacgctg cggagggact ttctgaggct gcagctggcc | 1080 |
| aacaaggagc gttctgaggc cctacggagg cagcagctgg agcagcagca gcgggagaat | 1140 |
| gaggagcaca gcggcagct gctggccgag cgtcagaagc gcatcgagga gcagaaagag | 1200 |
| cagaggcggc ggctggagga gcaacaaagg cgagagaagc agctgcggaa gcagcaggag | 1260 |
| agggagcagc gccggcacta tgaggagcag atgcgccggg aggagagag gaggcgtgcg | 1320 |
| gagcatgaac aggaatataa gcgcaaacaa ttggaagaac agacaagc agaaagactg | 1380 |
| cagaggcagc taaagcaaga aagagactac ttagtttccc ttcagcatca gcggcaggag | 1440 |
| cagaggcctg tggagaagaa gcactgtac cattacaaag aaggaatgag tcctagtgag | 1500 |
| aagccagcat gggccaagga gatcccacat ctggtagctg taaaatccca gggacctgcc | 1560 |
| ttgaccgcct cccagtcagt gcacgagcag cccacaaagg gcctctctgg gtttcaggag | 1620 |
| gctctgaacg tgacctccca ccgcgtggag atgccacgcc agaactcaga tcccacctcg | 1680 |
| gaaaatcctc ctctccccac tcgcattgaa agtttgacc gaagctcttg gttacgacag | 1740 |
| gaagaagaca ttccaccaaa ggtgcctcaa agaacaactt ctatatcccc agcattagcc | 1800 |
| agaaagaatt ctcctgggaa tggtagtgct ctgggaccca gactaggatc tcaacccatc | 1860 |

-continued

```
agagcaagca acccctgatct ccggagaact gagcccatct tggagagccc cttgcagagg    1920
accagcagtg gcagttcctc cagctccagc accctagct cccagcccag ctcccaagga     1980
ggctcccagc ctggatcaca agcaggatcc agtgaacgca ccagagttcg agccaacagt    2040
aagtcagaag gatcacctgt gcttccccat gagcctgcca aggtgaaacc agaagaatcc    2100
agggacatta cccggcccag tcgaccagct gatctgacgg cattagccaa agaactaaga    2160
gaactccgga ttgaagaaac aaaccgccca atgaagaagg tgactgatta ctcctcctcc    2220
agtgaggagt cagaaagtag cgaggaagag gaggaagatg agagagcga cccatgat      2280 gggacagtgg ctgtcagcga catacccaga ctgataccaa caggagctcc aggcagcaac    2340
gagcagtaca atgtgggaat ggtggggacg catgggctgg agacctctca tgcggacagt    2400
ttcagcggca gtatttcaag agaaggaacc ttgatgatta gagagacgtc tggagagaag    2460
aagcgatctg gccacagtga cagcaatggc tttgctggcc acatcaacct ccctgacctg    2520
gtgcagcaga gccattctcc agctggaacc ccgactgagg gactggggcg cgtctcaacc    2580
cattcccagg agatggactc tgggactgaa tatggcatgg ggagcagcac caaagcctcc    2640
ttcaccccct tgtggaccc cagagtatac cagacgtctc ccactgatga agatgaagag    2700
gatgaggaat catcagccgc agctctgttt actagcgaac ttcttaggca agaacaggcc    2760
aaactcaatg aagcaagaaa gatttcggtg gtaaatgtaa acccaaccaa cattcggcct    2820
catagcgaca caccagaaat cagaaaatac aagaaacgat tcaactcaga atactttgt    2880 gcagctctgt ggggtgtaaa ccttctggtg gggactgaaa atggcctgat gcttttggac    2940
cgaagtgggc aaggcaaagt ctataatctg atcaaccgga ggcgatttca gcagatggat    3000
gtgctagagg gactgaatgt ccttgtgaca atttcaggaa agaagaataa gctacgagtt    3060
tactatcttt catggttaag aaacagaata ctacataatg acccagaagt agaaaagaaa    3120
caaggctgga tcactgttgg ggacttggaa ggctgtatac attataaagt tgttaaatat    3180
gaaaggatca aattttttgt gattgcctta agaatgctg tggaaatata tgcttgggct    3240
cctaaaccgt atcataaatt catggcattt aagtcttttg cagatctcca gcacaagcct    3300
ctgctagttg atctcacggt agaagaaggt caaagattaa aggttatttt tggttcacac    3360
actggtttcc atgtaattga tgttgattca ggaaactctt atgatatcta cataccatct    3420
catattcagg gcaatatcac tcctcatgct attgtcatct tgcctaaaac agatggaatg    3480
gaaatgcttg tttgctatga ggatgagggg gtgtatgtaa acacctatgg ccggataact    3540
aaggatgtgg tgctccaatg gggagaaatg cccacgtctg tggcctacat tcattccaat    3600
cagataatgg gctgggcga gaaagctatt gagatccggt cagtggaaac aggacatttg    3660
gatggagtat ttatgcataa gcgagctcaa aggttaaagt ttctatgtga aagaaatgat    3720
aaggtatttt ttgcatccgt gcgatctgga ggaagtagcc aagtgttttt catgaccctc    3780
aacagaaatt ccatgatgaa ctggtaa                                      3807
```

<210> SEQ ID NO 9
<211> LENGTH: 1332
<212> TYPE: PRT
<213> ORGANISM: Artificial sequence
<220> FEATURE:
<223> OTHER INFORMATION: synthetic

<400> SEQUENCE: 9

```
Met Ala Ser Asp Ser Pro Ala Arg Ser Leu Asp Glu Ile Asp Leu Ser
1               5                   10                  15
```

-continued

```
Ala Leu Arg Asp Pro Ala Gly Ile Phe Glu Leu Val Glu Leu Val Gly
                 20                  25                  30

Asn Gly Thr Tyr Gly Gln Val Tyr Lys Gly Arg His Val Lys Thr Gly
             35                  40                  45

Gln Leu Ala Ala Ile Lys Val Met Asp Val Thr Gly Asp Glu Glu Glu
         50                  55                  60

Glu Ile Lys Gln Glu Ile Asn Met Leu Lys Lys Tyr Ser His His Arg
 65                  70                  75                  80

Asn Ile Ala Thr Tyr Tyr Gly Ala Phe Ile Lys Lys Asn Pro Pro Gly
                 85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
            115                 120                 125

Trp Ile Ala Tyr Ile Cys Arg Glu Ile Leu Arg Gly Leu Ser His Leu
            130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
            195                 200                 205

Thr Tyr Asp Phe Lys Ser Asp Leu Trp Ser Leu Gly Ile Thr Ala Ile
            210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
            275                 280                 285

Ile Arg Asp Gln Pro Asn Glu Arg Gln Val Arg Ile Gln Leu Lys Asp
            290                 295                 300

His Ile Asp Arg Thr Lys Lys Lys Arg Gly Glu Lys Asp Glu Thr Glu
305                 310                 315                 320

Tyr Glu Tyr Ser Gly Ser Glu Glu Glu Glu Glu Asn Asp Ser Gly
                325                 330                 335

Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
            355                 360                 365

Arg Arg Gln Gln Leu Glu Gln Gln Gln Arg Glu Asn Glu Glu His Lys
            370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Gln Arg Arg Glu Lys Glu Leu Arg
            405                 410                 415

Lys Gln Gln Glu Arg Glu Gln Arg Arg His Tyr Glu Glu Gln Met Arg
            420                 425                 430
```

-continued

```
Arg Glu Glu Glu Arg Arg Ala Glu His Glu Gln Glu Tyr Lys Arg
        435                 440                 445
Lys Gln Leu Glu Glu Gln Arg Gln Ala Glu Arg Leu Gln Arg Gln Leu
    450                 455                 460
Lys Gln Glu Arg Asp Tyr Leu Val Ser Leu Gln His Gln Arg Gln Glu
465                 470                 475                 480
Gln Arg Pro Val Glu Lys Lys Pro Leu Tyr His Tyr Lys Glu Gly Met
            485                 490                 495
Ser Pro Ser Glu Lys Pro Ala Trp Ala Lys Glu Val Glu Glu Arg Ser
            500                 505                 510
Arg Leu Asn Arg Gln Ser Ser Pro Ala Met Pro His Lys Val Ala Asn
        515                 520                 525
Arg Ile Ser Asp Pro Asn Leu Pro Pro Arg Ser Glu Ser Phe Ser Ile
    530                 535                 540
Ser Gly Val Gln Pro Ala Arg Thr Pro Pro Met Leu Arg Pro Val Asp
545                 550                 555                 560
Pro Gln Ile Pro His Leu Val Ala Val Lys Ser Gln Gly Pro Ala Leu
            565                 570                 575
Thr Ala Ser Gln Ser Val His Glu Gln Pro Thr Lys Gly Leu Ser Gly
        580                 585                 590
Phe Gln Glu Ala Leu Asn Val Thr Ser His Arg Val Glu Met Pro Arg
    595                 600                 605
Gln Asn Ser Asp Pro Thr Ser Glu Asn Pro Pro Leu Pro Thr Arg Ile
610                 615                 620
Glu Lys Phe Asp Arg Ser Ser Trp Leu Arg Gln Glu Glu Asp Ile Pro
625                 630                 635                 640
Pro Lys Val Pro Gln Arg Thr Thr Ser Ile Ser Pro Ala Leu Ala Arg
            645                 650                 655
Lys Asn Ser Pro Gly Asn Gly Ser Ala Leu Gly Pro Arg Leu Gly Ser
        660                 665                 670
Gln Pro Ile Arg Ala Ser Asn Pro Asp Leu Arg Arg Thr Glu Pro Ile
    675                 680                 685
Leu Glu Ser Pro Leu Gln Arg Thr Ser Ser Gly Ser Ser Ser Ser Ser
690                 695                 700
Ser Thr Pro Ser Ser Gln Pro Ser Ser Gln Gly Gly Ser Gln Pro Gly
705                 710                 715                 720
Ser Gln Ala Gly Ser Ser Glu Arg Thr Arg Val Arg Ala Asn Ser Lys
            725                 730                 735
Ser Glu Gly Ser Pro Val Leu Pro His Glu Pro Ala Lys Val Lys Pro
            740                 745                 750
Glu Glu Ser Arg Asp Ile Thr Arg Pro Ser Arg Pro Ala Ser Tyr Lys
        755                 760                 765
Lys Ala Ile Asp Glu Asp Leu Thr Ala Leu Ala Lys Glu Leu Arg Glu
    770                 775                 780
Leu Arg Ile Glu Glu Thr Asn Arg Pro Met Lys Lys Val Thr Asp Tyr
785                 790                 795                 800
Ser Ser Ser Ser Glu Glu Ser Glu Ser Ser Glu Glu Glu Glu Glu Asp
            805                 810                 815
Gly Glu Ser Glu Thr His Asp Gly Thr Val Ala Val Ser Asp Ile Pro
        820                 825                 830
Arg Leu Ile Pro Thr Gly Ala Pro Gly Ser Asn Glu Gln Tyr Asn Val
    835                 840                 845
Gly Met Val Gly Thr His Gly Leu Glu Thr Ser His Ala Asp Ser Phe
```

```
            850                 855                 860
Ser Gly Ser Ile Ser Arg Glu Gly Thr Leu Met Ile Arg Glu Thr Ser
865                 870                 875                 880

Gly Glu Lys Lys Arg Ser Gly His Ser Asp Ser Asn Gly Phe Ala Gly
                    885                 890                 895

His Ile Asn Leu Pro Asp Leu Val Gln Gln Ser His Ser Pro Ala Gly
                900                 905                 910

Thr Pro Thr Glu Gly Leu Gly Arg Val Ser Thr His Ser Gln Glu Met
                915                 920                 925

Asp Ser Gly Thr Glu Tyr Gly Met Gly Ser Ser Thr Lys Ala Ser Phe
                930                 935                 940

Thr Pro Phe Val Asp Pro Arg Val Tyr Gln Thr Ser Pro Thr Asp Glu
945                 950                 955                 960

Asp Glu Glu Asp Glu Glu Ser Ser Ala Ala Ala Leu Phe Thr Ser Glu
                965                 970                 975

Leu Leu Arg Gln Glu Gln Ala Lys Leu Asn Glu Ala Arg Lys Ile Ser
                980                 985                 990

Val Val Asn Val Asn Pro Thr Asn Ile Arg Pro His Ser Asp Thr Pro
                995                 1000                1005

Glu Ile Arg Lys Tyr Lys Lys Arg Phe Asn Ser Glu Ile Leu Cys
1010                1015                1020

Ala Ala Leu Trp Gly Val Asn Leu Leu Val Gly Thr Glu Asn Gly
1025                1030                1035

Leu Met Leu Leu Asp Arg Ser Gly Gln Gly Lys Val Tyr Asn Leu
1040                1045                1050

Ile Asn Arg Arg Arg Phe Gln Gln Met Asp Val Leu Glu Gly Leu
1055                1060                1065

Asn Val Leu Val Thr Ile Ser Gly Lys Lys Asn Lys Leu Arg Val
1070                1075                1080

Tyr Tyr Leu Ser Trp Leu Arg Asn Arg Ile Leu His Asn Asp Pro
1085                1090                1095

Glu Val Glu Lys Lys Gln Gly Trp Ile Thr Val Gly Asp Leu Glu
1100                1105                1110

Gly Cys Ile His Tyr Lys Val Val Lys Tyr Glu Arg Ile Lys Phe
1115                1120                1125

Leu Val Ile Ala Leu Lys Asn Ala Val Glu Ile Tyr Ala Trp Ala
1130                1135                1140

Pro Lys Pro Tyr His Lys Phe Met Ala Phe Lys Ser Phe Ala Asp
1145                1150                1155

Leu Gln His Lys Pro Leu Leu Val Asp Leu Thr Val Glu Glu Gly
1160                1165                1170

Gln Arg Leu Lys Val Ile Phe Gly Ser His Thr Gly Phe His Val
1175                1180                1185

Ile Asp Val Asp Ser Gly Asn Ser Tyr Asp Ile Tyr Ile Pro Ser
1190                1195                1200

His Ile Gln Gly Asn Ile Thr Pro His Ala Ile Val Ile Leu Pro
1205                1210                1215

Lys Thr Asp Gly Met Glu Met Leu Val Cys Tyr Glu Asp Glu Gly
1220                1225                1230

Val Tyr Val Asn Thr Tyr Gly Arg Ile Thr Lys Asp Val Val Leu
1235                1240                1245

Gln Trp Gly Glu Met Pro Thr Ser Val Ala Tyr Ile His Ser Asn
1250                1255                1260
```

```
Gln Ile Met Gly Trp Gly Glu Lys Ala Ile Glu Ile Arg Ser Val
    1265            1270                1275

Glu Thr Gly His Leu Asp Gly Val Phe Met His Lys Arg Ala Gln
    1280            1285                1290

Arg Leu Lys Phe Leu Cys Glu Arg Asn Asp Lys Val Phe Phe Ala
    1295            1300                1305

Ser Val Arg Ser Gly Gly Ser Ser Gln Val Phe Phe Met Thr Leu
    1310            1315                1320

Asn Arg Asn Ser Met Met Asn Trp Glx
    1325            1330
```

<210> SEQ ID NO 10
<211> LENGTH: 1306
<212> TYPE: PRT
<213> ORGANISM: Artificial sequence
<220> FEATURE:
<223> OTHER INFORMATION: synthetic

<400> SEQUENCE: 10

```
Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
                20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Gly Asp Glu Glu Glu
        50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
                100                 105                 110

Val Thr Asp Leu Ile Lys Asn Thr Lys Gly Asn Thr Leu Lys Glu Glu
            115                 120                 125

Trp Ile Ala Tyr Ile Cys Arg Glu Ile Leu Arg Gly Leu Ser His Leu
        130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
                180                 185                 190

Tyr Trp Met Ala Pro Glu Val Ile Ala Cys Asp Glu Asn Pro Asp Ala
            195                 200                 205

Thr Tyr Asp Phe Lys Ser Asp Leu Trp Ser Leu Gly Ile Thr Ala Ile
        210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
                260                 265                 270

Asn His Ser Gln Arg Pro Ala Thr Glu Gln Leu Met Lys His Pro Phe
            275                 280                 285
```

-continued

```
Ile Arg Asp Gln Pro Asn Glu Arg Gln Val Arg Ile Gln Leu Lys Asp
    290                 295                 300
His Ile Asp Arg Thr Lys Lys Arg Gly Glu Lys Asp Glu Thr Glu
305                 310                 315                 320
Tyr Glu Tyr Ser Gly Ser Glu Glu Glu Glu Asn Asp Ser Gly
                325                 330                 335
Glu Pro Ser Ser Ile Leu Asn Leu Pro Gly Glu Ser Thr Leu Arg Arg
                340                 345                 350
Asp Phe Leu Arg Leu Gln Leu Ala Asn Lys Glu Arg Ser Glu Ala Leu
        355                 360                 365
Arg Arg Gln Gln Leu Glu Gln Gln Arg Glu Asn Glu Glu His Lys
370                 375                 380
Arg Gln Leu Leu Ala Glu Arg Gln Lys Arg Ile Glu Glu Gln Lys Glu
385                 390                 395                 400
Gln Arg Arg Arg Leu Glu Glu Gln Arg Arg Glu Lys Glu Leu Arg
                405                 410                 415
Lys Gln Gln Glu Arg Glu Gln Arg Arg His Tyr Glu Gln Met Arg
            420                 425                 430
Arg Glu Glu Arg Arg Arg Ala Glu His Glu Gln Glu Tyr Ile Arg
            435                 440                 445
Arg Gln Leu Glu Glu Glu Gln Arg Gln Leu Glu Ile Leu Gln Gln Gln
    450                 455                 460
Leu Leu His Glu Gln Ala Leu Leu Glu Tyr Lys Arg Lys Gln Leu
465                 470                 475                 480
Glu Glu Gln Arg Gln Ala Glu Arg Leu Gln Arg Gln Leu Lys Gln Glu
                485                 490                 495
Arg Asp Tyr Leu Val Ser Leu Gln His Gln Arg Gln Glu Gln Arg Pro
            500                 505                 510
Val Glu Lys Lys Pro Leu Tyr His Tyr Lys Glu Gly Met Ser Pro Ser
            515                 520                 525
Glu Lys Pro Ala Trp Ala Lys Glu Ile Pro His Leu Val Ala Val Lys
    530                 535                 540
Ser Gln Gly Pro Ala Leu Thr Ala Ser Gln Ser Val His Glu Gln Pro
545                 550                 555                 560
Thr Lys Gly Leu Ser Gly Phe Gln Glu Ala Leu Asn Val Thr Ser His
                565                 570                 575
Arg Val Glu Met Pro Arg Gln Asn Ser Asp Pro Thr Ser Glu Asn Pro
            580                 585                 590
Pro Leu Pro Thr Arg Ile Glu Lys Phe Asp Arg Ser Ser Trp Leu Arg
            595                 600                 605
Gln Glu Glu Asp Ile Pro Pro Lys Val Pro Gln Arg Thr Thr Ser Ile
    610                 615                 620
Ser Pro Ala Leu Ala Arg Lys Asn Ser Pro Gly Asn Gly Ser Ala Leu
625                 630                 635                 640
Gly Pro Arg Leu Gly Ser Gln Pro Ile Arg Ala Ser Asn Pro Asp Leu
                645                 650                 655
Arg Arg Thr Glu Pro Ile Leu Glu Ser Pro Leu Gln Arg Thr Ser Ser
            660                 665                 670
Gly Ser Ser Ser Ser Ser Thr Pro Ser Ser Gln Pro Ser Ser Gln
            675                 680                 685
Gly Gly Ser Gln Pro Gly Ser Gln Ala Gly Ser Ser Glu Arg Thr Arg
    690                 695                 700
```

```
Val Arg Ala Asn Ser Lys Ser Glu Gly Ser Pro Val Leu Pro His Glu
705                 710                 715                 720

Pro Ala Lys Val Lys Pro Glu Ser Arg Asp Ile Thr Arg Pro Ser
            725                 730                 735

Arg Pro Ala Ser Tyr Lys Lys Ala Ile Asp Glu Asp Leu Thr Ala Leu
                740                 745                 750

Ala Lys Glu Leu Arg Glu Leu Arg Ile Glu Glu Thr Asn Arg Pro Met
            755                 760                 765

Lys Lys Val Thr Asp Tyr Ser Ser Ser Gly Glu Ser Glu Ser Ser
770                 775                 780

Glu Glu Glu Glu Glu Asp Gly Glu Ser Glu Thr His Asp Gly Thr Val
785                 790                 795                 800

Ala Val Ser Asp Ile Pro Arg Leu Ile Pro Thr Gly Ala Pro Gly Ser
                805                 810                 815

Asn Glu Gln Tyr Asn Val Gly Met Val Gly Thr His Gly Leu Glu Thr
                820                 825                 830

Ser His Ala Asp Ser Phe Ser Gly Ser Ile Ser Arg Glu Gly Thr Leu
                835                 840                 845

Met Ile Arg Glu Thr Ser Gly Glu Lys Lys Arg Ser Gly His Ser Asp
850                 855                 860

Ser Asn Gly Phe Ala Gly His Ile Asn Leu Pro Asp Leu Val Gln Gln
865                 870                 875                 880

Ser His Ser Pro Ala Gly Thr Pro Thr Glu Gly Leu Gly Arg Val Ser
                885                 890                 895

Thr His Ser Gln Glu Met Asp Ser Gly Thr Glu Tyr Gly Met Gly Ser
                900                 905                 910

Ser Thr Lys Ala Ser Phe Thr Pro Phe Val Asp Pro Arg Val Tyr Gln
        915                 920                 925

Thr Ser Pro Thr Asp Glu Asp Glu Glu Asp Glu Glu Ser Ser Ala Ala
        930                 935                 940

Ala Leu Phe Thr Ser Glu Leu Leu Arg Gln Glu Gln Ala Lys Leu Asn
945                 950                 955                 960

Glu Ala Arg Lys Ile Ser Val Val Asn Val Asn Pro Thr Asn Ile Arg
            965                 970                 975

Pro His Ser Asp Thr Pro Glu Ile Arg Lys Tyr Lys Lys Arg Phe Asn
            980                 985                 990

Ser Glu Ile Leu Cys Ala Ala Leu Trp Gly Val Asn Leu Leu Val Gly
            995                 1000                1005

Thr Glu Asn Gly Leu Met Leu Leu Asp Arg Ser Gly Gln Gly Lys
    1010                1015                1020

Val Tyr Asn Leu Ile Asn Arg Arg Arg Phe Gln Gln Met Asp Val
    1025                1030                1035

Leu Glu Gly Leu Asn Val Leu Val Thr Ile Ser Gly Lys Lys Asn
    1040                1045                1050

Lys Leu Arg Val Tyr Tyr Leu Ser Trp Leu Arg Asn Arg Ile Leu
    1055                1060                1065

His Asn Asp Pro Glu Val Glu Lys Lys Gln Gly Trp Ile Thr Val
    1070                1075                1080

Gly Asp Leu Glu Gly Cys Ile His Tyr Lys Val Val Lys Tyr Glu
    1085                1090                1095

Arg Ile Lys Phe Leu Val Ile Ala Leu Lys Asn Ala Val Glu Ile
    1100                1105                1110

Tyr Ala Trp Ala Pro Lys Pro Tyr His Lys Phe Met Ala Phe Lys
```

-continued

```
            1115                1120                1125

Ser Phe Ala Asp Leu Gln His Lys Pro Leu Leu Val Asp Leu Thr
    1130                1135                1140

Val Glu Glu Gly Gln Arg Leu Lys Val Ile Phe Gly Ser His Thr
    1145                1150                1155

Gly Phe His Val Ile Asp Val Asp Ser Gly Asn Ser Tyr Asp Ile
    1160                1165                1170

Tyr Ile Pro Ser His Ile Gln Gly Asn Ile Thr Pro His Ala Ile
    1175                1180                1185

Val Ile Leu Pro Lys Thr Asp Gly Met Glu Met Leu Val Cys Tyr
    1190                1195                1200

Glu Asp Glu Gly Val Tyr Val Asn Thr Tyr Gly Arg Ile Thr Lys
    1205                1210                1215

Asp Val Val Leu Gln Trp Gly Glu Met Pro Thr Ser Val Ala Tyr
    1220                1225                1230

Ile His Ser Asn Gln Ile Met Gly Trp Gly Glu Lys Ala Ile Glu
    1235                1240                1245

Ile Arg Ser Val Glu Thr Gly His Leu Asp Gly Val Phe Met His
    1250                1255                1260

Lys Arg Ala Gln Arg Leu Lys Phe Leu Cys Glu Arg Asn Asp Lys
    1265                1270                1275

Val Phe Phe Ala Ser Val Arg Ser Gly Gly Ser Ser Gln Val Phe
    1280                1285                1290

Phe Met Thr Leu Asn Arg Asn Ser Met Met Asn Trp Glx
    1295                1300                1305
```

<210> SEQ ID NO 11
<211> LENGTH: 1353
<212> TYPE: PRT
<213> ORGANISM: Artificial sequence
<220> FEATURE:
<223> OTHER INFORMATION: synthetic

<400> SEQUENCE: 11

```
Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
                20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Gly Asp Glu Glu Glu
        50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
                100                 105                 110

Val Thr Asp Leu Ile Lys Asn Thr Lys Gly Asn Thr Leu Lys Glu Glu
            115                 120                 125

Trp Ile Ala Tyr Ile Cys Arg Glu Ile Leu Arg Gly Leu Ser His Leu
        130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
```

-continued

```
                165                 170                 175
        Gln Leu Asp Arg Thr Val Gly Arg Arg Asn Thr Phe Ile Gly Thr Pro
                    180                 185                 190

Tyr Trp Met Ala Pro Glu Val Ile Ala Cys Asp Glu Asn Pro Asp Ala
                    195                 200                 205

Thr Tyr Asp Phe Lys Ser Asp Leu Trp Ser Leu Gly Ile Thr Ala Ile
                    210                 215                 220

Glu Met Ala Glu Gly Ala Pro Pro Leu Cys Asp Met His Pro Met Arg
        225                 230                 235                 240

Ala Leu Phe Leu Ile Pro Arg Asn Pro Ala Pro Arg Leu Lys Ser Lys
                    245                 250                 255

Lys Trp Ser Lys Lys Phe Gln Ser Phe Ile Glu Ser Cys Leu Val Lys
                    260                 265                 270

Asn His Ser Gln Arg Pro Ala Thr Glu Gln Leu Met Lys His Pro Phe
                    275                 280                 285

Ile Arg Asp Gln Pro Asn Glu Arg Gln Val Arg Ile Gln Leu Lys Asp
                    290                 295                 300

His Ile Asp Arg Thr Lys Lys Lys Arg Gly Glu Lys Asp Glu Thr Glu
        305                 310                 315                 320

Tyr Glu Tyr Ser Gly Ser Glu Glu Glu Glu Glu Asn Asp Ser Gly
                    325                 330                 335

Glu Pro Ser Ser Ile Leu Asn Leu Pro Gly Glu Ser Thr Leu Arg Arg
                    340                 345                 350

Asp Phe Leu Arg Leu Gln Leu Ala Asn Lys Glu Arg Ser Glu Ala Leu
                    355                 360                 365

Arg Arg Gln Gln Leu Glu Gln Gln Arg Glu Asn Glu Glu His Lys
        370                 375                 380

Arg Gln Leu Leu Ala Glu Arg Gln Lys Arg Ile Glu Glu Gln Lys Glu
        385                 390                 395                 400

Gln Arg Arg Arg Leu Glu Glu Gln Arg Arg Glu Lys Glu Leu Arg
                    405                 410                 415

Lys Gln Gln Glu Arg Glu Gln Arg His Tyr Glu Glu Gln Met Arg
                    420                 425                 430

Arg Glu Glu Glu Arg Arg Arg Ala Glu His Glu Gln Glu Tyr Ile Arg
                    435                 440                 445

Arg Gln Leu Glu Glu Glu Gln Arg Gln Leu Glu Ile Leu Gln Gln Gln
                    450                 455                 460

Leu Leu His Glu Gln Ala Leu Leu Leu Glu Tyr Lys Arg Lys Gln Leu
        465                 470                 475                 480

Glu Glu Gln Arg Gln Ala Glu Arg Leu Gln Arg Gln Leu Lys Gln Glu
                    485                 490                 495

Arg Asp Tyr Leu Val Ser Leu Gln His Gln Arg Gln Glu Gln Arg Pro
                    500                 505                 510

Val Glu Lys Lys Pro Leu Tyr His Tyr Lys Glu Gly Met Ser Pro Ser
                    515                 520                 525

Glu Lys Pro Ala Trp Ala Lys Glu Val Glu Glu Arg Ser Arg Leu Asn
                    530                 535                 540

Arg Gln Ser Ser Pro Ala Met Pro His Lys Val Ala Asn Arg Ile Ser
        545                 550                 555                 560

Asp Pro Asn Leu Pro Pro Arg Ser Glu Ser Phe Ser Ile Ser Gly Val
                    565                 570                 575

Gln Pro Ala Arg Thr Pro Pro Met Leu Arg Pro Val Asp Pro Gln Ile
                    580                 585                 590
```

-continued

```
Pro His Leu Val Ala Val Lys Ser Gln Gly Pro Ala Leu Thr Ala Ser
        595                 600                 605

Gln Ser Val His Glu Gln Pro Thr Lys Gly Leu Ser Gly Phe Gln Glu
        610                 615                 620

Ala Leu Asn Val Thr Ser His Arg Val Glu Met Pro Arg Gln Asn Ser
625                 630                 635                 640

Asp Pro Thr Ser Glu Asn Pro Leu Pro Thr Arg Ile Glu Lys Phe
                645                 650                 655

Asp Arg Ser Ser Trp Leu Arg Gln Glu Glu Asp Ile Pro Pro Lys Val
            660                 665                 670

Pro Gln Arg Thr Thr Ser Ile Ser Pro Ala Leu Ala Arg Lys Asn Ser
        675                 680                 685

Pro Gly Asn Gly Ser Ala Leu Gly Pro Arg Leu Gly Ser Gln Pro Ile
    690                 695                 700

Arg Ala Ser Asn Pro Asp Leu Arg Arg Thr Glu Pro Ile Leu Glu Ser
705                 710                 715                 720

Pro Leu Gln Arg Thr Ser Ser Gly Ser Ser Ser Ser Ser Thr Pro
                725                 730                 735

Ser Ser Gln Pro Ser Ser Gln Gly Gly Ser Gln Pro Gly Ser Gln Ala
            740                 745                 750

Gly Ser Ser Glu Arg Thr Arg Val Arg Ala Asn Ser Lys Ser Glu Gly
        755                 760                 765

Ser Pro Val Leu Pro His Glu Pro Ala Lys Val Lys Pro Glu Glu Ser
    770                 775                 780

Arg Asp Ile Thr Arg Pro Ser Arg Pro Ala Asp Leu Thr Ala Leu Ala
785                 790                 795                 800

Lys Glu Leu Arg Glu Leu Arg Ile Glu Glu Thr Asn Arg Pro Met Lys
                805                 810                 815

Lys Val Thr Asp Tyr Ser Ser Ser Glu Glu Ser Glu Ser Ser Glu
            820                 825                 830

Glu Glu Glu Glu Asp Gly Glu Ser Glu Thr His Asp Gly Thr Val Ala
        835                 840                 845

Val Ser Asp Ile Pro Arg Leu Ile Pro Thr Gly Ala Pro Gly Ser Asn
850                 855                 860

Glu Gln Tyr Asn Val Gly Met Val Gly Thr His Gly Leu Glu Thr Ser
865                 870                 875                 880

His Ala Asp Ser Phe Ser Gly Ser Ile Ser Arg Glu Gly Thr Leu Met
                885                 890                 895

Ile Arg Glu Thr Ser Gly Glu Lys Lys Arg Ser Gly His Ser Asp Ser
            900                 905                 910

Asn Gly Phe Ala Gly His Ile Asn Leu Pro Asp Leu Val Gln Gln Ser
        915                 920                 925

His Ser Pro Ala Gly Thr Pro Thr Glu Gly Leu Gly Arg Val Ser Thr
    930                 935                 940

His Ser Gln Glu Met Asp Ser Gly Thr Glu Tyr Gly Met Gly Ser Ser
945                 950                 955                 960

Thr Lys Ala Ser Phe Thr Pro Phe Val Asp Pro Arg Val Tyr Gln Thr
                965                 970                 975

Ser Pro Thr Asp Glu Asp Glu Glu Asp Glu Glu Ser Ser Ala Ala Ala
            980                 985                 990

Leu Phe Thr Ser Glu Leu Leu Arg  Gln Glu Gln Ala Lys  Leu Asn Glu
        995                 1000                1005
```

-continued

```
Ala Arg Lys Ile Ser Val Val Asn Val Asn Pro Thr Asn Ile Arg
    1010                1015                1020
Pro His Ser Asp Thr Pro Glu Ile Arg Lys Tyr Lys Lys Arg Phe
    1025                1030                1035
Asn Ser Glu Ile Leu Cys Ala Ala Leu Trp Gly Val Asn Leu Leu
    1040                1045                1050
Val Gly Thr Glu Asn Gly Leu Met Leu Leu Asp Arg Ser Gly Gln
    1055                1060                1065
Gly Lys Val Tyr Asn Leu Ile Asn Arg Arg Phe Gln Gln Met
    1070                1075                1080
Asp Val Leu Glu Gly Leu Asn Val Leu Val Thr Ile Ser Gly Lys
    1085                1090                1095
Lys Asn Lys Leu Arg Val Tyr Tyr Leu Ser Trp Leu Arg Asn Arg
    1100                1105                1110
Ile Leu His Asn Asp Pro Glu Val Glu Lys Lys Gln Gly Trp Ile
    1115                1120                1125
Thr Val Gly Asp Leu Glu Gly Cys Ile His Tyr Lys Val Val Lys
    1130                1135                1140
Tyr Glu Arg Ile Lys Phe Leu Val Ile Ala Leu Lys Asn Ala Val
    1145                1150                1155
Glu Ile Tyr Ala Trp Ala Pro Lys Pro Tyr His Lys Phe Met Ala
    1160                1165                1170
Phe Lys Ser Phe Ala Asp Leu Gln His Lys Pro Leu Leu Val Asp
    1175                1180                1185
Leu Thr Val Glu Glu Gly Gln Arg Leu Lys Val Ile Phe Gly Ser
    1190                1195                1200
His Thr Gly Phe His Val Ile Asp Val Asp Ser Gly Asn Ser Tyr
    1205                1210                1215
Asp Ile Tyr Ile Pro Ser His Ile Gln Gly Asn Ile Thr Pro His
    1220                1225                1230
Ala Ile Val Ile Leu Pro Lys Thr Asp Gly Met Glu Met Leu Val
    1235                1240                1245
Cys Tyr Glu Asp Glu Gly Val Tyr Val Asn Thr Tyr Gly Arg Ile
    1250                1255                1260
Thr Lys Asp Val Val Leu Gln Trp Gly Glu Met Pro Thr Ser Val
    1265                1270                1275
Ala Tyr Ile His Ser Asn Gln Ile Met Gly Trp Gly Glu Lys Ala
    1280                1285                1290
Ile Glu Ile Arg Ser Val Glu Thr Gly His Leu Asp Gly Val Phe
    1295                1300                1305
Met His Lys Arg Ala Gln Arg Leu Lys Phe Leu Cys Glu Arg Asn
    1310                1315                1320
Asp Lys Val Phe Phe Ala Ser Val Arg Ser Gly Gly Ser Ser Gln
    1325                1330                1335
Val Phe Phe Met Thr Leu Asn Arg Asn Ser Met Met Asn Trp Glx
    1340                1345                1350
```

<210> SEQ ID NO 12
<211> LENGTH: 1277
<212> TYPE: PRT
<213> ORGANISM: Artificial sequence
<220> FEATURE:
<223> OTHER INFORMATION: synthetic

<400> SEQUENCE: 12

```
Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
            20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Gly Asp Glu Glu Glu
50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
            85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
            115                 120                 125

Trp Ile Ala Tyr Ile Cys Arg Glu Ile Leu Arg Gly Leu Ser His Leu
130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
            165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
            195                 200                 205

Thr Tyr Asp Phe Lys Ser Asp Leu Trp Ser Leu Gly Ile Thr Ala Ile
210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
            245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
            275                 280                 285

Ile Arg Asp Gln Pro Asn Glu Arg Gln Val Arg Ile Gln Leu Lys Asp
            290                 295                 300

His Ile Asp Arg Thr Lys Lys Arg Gly Glu Lys Asp Glu Thr Glu
305                 310                 315                 320

Tyr Glu Tyr Ser Gly Ser Glu Glu Glu Glu Glu Asn Asp Ser Gly
            325                 330                 335

Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
            355                 360                 365

Arg Arg Gln Gln Leu Glu Gln Gln Arg Glu Asn Glu Glu His Lys
            370                 375                 380

Arg Gln Leu Leu Ala Glu Arg Lys Arg Ile Glu Glu Gln Lys Glu
385                 390                 395                 400

Gln Arg Arg Arg Leu Glu Glu Gln Arg Arg Glu Lys Glu Leu Arg
            405                 410                 415

Lys Gln Gln Glu Arg Glu Gln Arg Arg His Tyr Glu Glu Gln Met Arg
```

-continued

```
                420                 425                 430
Arg Glu Glu Arg Arg Ala Glu His Glu Gln Glu Tyr Lys Arg
        435                 440                 445
Lys Gln Leu Glu Gln Arg Gln Ala Glu Arg Leu Gln Arg Gln Leu
450                 455                 460
Lys Gln Glu Arg Asp Tyr Leu Val Ser Leu Gln His Gln Arg Gln Glu
465                 470                 475                 480
Gln Arg Pro Val Glu Lys Pro Leu Tyr His Tyr Lys Glu Gly Met
                485                 490                 495
Ser Pro Ser Glu Lys Pro Ala Trp Ala Lys Glu Ile Pro His Leu Val
        500                 505                 510
Ala Val Lys Ser Gln Gly Pro Ala Leu Thr Ala Ser Gln Ser Val His
        515                 520                 525
Glu Gln Pro Thr Lys Gly Leu Ser Gly Phe Gln Glu Ala Leu Asn Val
530                 535                 540
Thr Ser His Arg Val Glu Met Pro Arg Gln Asn Ser Asp Pro Thr Ser
545                 550                 555                 560
Glu Asn Pro Pro Leu Pro Thr Arg Ile Glu Lys Phe Asp Arg Ser Ser
                565                 570                 575
Trp Leu Arg Gln Glu Glu Asp Ile Pro Pro Lys Val Pro Gln Arg Thr
        580                 585                 590
Thr Ser Ile Ser Pro Ala Leu Ala Arg Lys Asn Ser Pro Gly Asn Gly
        595                 600                 605
Ser Ala Leu Gly Pro Arg Leu Gly Ser Gln Pro Ile Arg Ala Ser Asn
        610                 615                 620
Pro Asp Leu Arg Arg Thr Glu Pro Ile Leu Glu Ser Pro Leu Gln Arg
625                 630                 635                 640
Thr Ser Ser Gly Ser Ser Ser Ser Thr Pro Ser Ser Gln Pro
                645                 650                 655
Ser Ser Gln Gly Gly Ser Gln Pro Gly Ser Gln Ala Gly Ser Ser Glu
                660                 665                 670
Arg Thr Arg Val Arg Ala Asn Ser Lys Ser Glu Gly Ser Pro Val Leu
        675                 680                 685
Pro His Glu Pro Ala Lys Val Lys Pro Glu Glu Ser Arg Asp Ile Thr
        690                 695                 700
Arg Pro Ser Arg Pro Ala Ser Tyr Lys Lys Ala Ile Asp Glu Asp Leu
705                 710                 715                 720
Thr Ala Leu Ala Lys Glu Leu Arg Glu Leu Arg Ile Glu Glu Thr Asn
                725                 730                 735
Arg Pro Met Lys Lys Val Thr Asp Tyr Ser Ser Ser Ser Glu Glu Ser
                740                 745                 750
Glu Ser Ser Glu Glu Glu Glu Asp Gly Glu Ser Glu Thr His Asp
        755                 760                 765
Gly Thr Val Ala Val Ser Asp Ile Pro Arg Leu Ile Pro Thr Gly Ala
770                 775                 780
Pro Gly Ser Asn Glu Gln Tyr Asn Val Gly Met Val Gly Thr His Gly
785                 790                 795                 800
Leu Glu Thr Ser His Ala Asp Ser Phe Ser Gly Ser Ile Ser Arg Glu
                805                 810                 815
Gly Thr Leu Met Ile Arg Glu Thr Ser Gly Glu Lys Lys Arg Ser Gly
                820                 825                 830
His Ser Asp Ser Asn Gly Phe Ala Gly His Ile Asn Leu Pro Asp Leu
        835                 840                 845
```

-continued

```
Val Gln Gln Ser His Ser Pro Ala Gly Thr Pro Thr Glu Gly Leu Gly
    850                 855                 860
Arg Val Ser Thr His Ser Gln Glu Met Asp Ser Gly Thr Glu Tyr Gly
865                 870                 875                 880
Met Gly Ser Ser Thr Lys Ala Ser Phe Thr Pro Phe Val Asp Pro Arg
                885                 890                 895
Val Tyr Gln Thr Ser Pro Thr Asp Glu Asp Glu Asp Glu Glu Ser
            900                 905                 910
Ser Ala Ala Ala Leu Phe Thr Ser Glu Leu Leu Arg Gln Glu Gln Ala
            915                 920                 925
Lys Leu Asn Glu Ala Arg Lys Ile Ser Val Val Asn Val Asn Pro Thr
            930                 935                 940
Asn Ile Arg Pro His Ser Asp Thr Pro Glu Ile Arg Lys Tyr Lys Lys
945                 950                 955                 960
Arg Phe Asn Ser Glu Ile Leu Cys Ala Ala Leu Trp Gly Val Asn Leu
                965                 970                 975
Leu Val Gly Thr Glu Asn Gly Leu Met Leu Leu Asp Arg Ser Gly Gln
            980                 985                 990
Gly Lys Val Tyr Asn Leu Ile Asn Arg Arg Arg Phe Gln Gln Met Asp
        995                 1000                1005
Val Leu Glu Gly Leu Asn Val Leu Val Thr Ile Ser Gly Lys Lys
    1010                1015                1020
Asn Lys Leu Arg Val Tyr Tyr Leu Ser Trp Leu Arg Asn Arg Ile
    1025                1030                1035
Leu His Asn Asp Pro Glu Val Glu Lys Lys Gln Gly Trp Ile Thr
    1040                1045                1050
Val Gly Asp Leu Glu Gly Cys Ile His Tyr Lys Val Val Lys Tyr
    1055                1060                1065
Glu Arg Ile Lys Phe Leu Val Ile Ala Leu Lys Asn Ala Val Glu
    1070                1075                1080
Ile Tyr Ala Trp Ala Pro Lys Pro Tyr His Lys Phe Met Ala Phe
    1085                1090                1095
Lys Ser Phe Ala Asp Leu Gln His Lys Pro Leu Leu Val Asp Leu
    1100                1105                1110
Thr Val Glu Glu Gly Gln Arg Leu Lys Val Ile Phe Gly Ser His
    1115                1120                1125
Thr Gly Phe His Val Ile Asp Val Asp Ser Gly Asn Ser Tyr Asp
    1130                1135                1140
Ile Tyr Ile Pro Ser His Ile Gln Gly Asn Ile Thr Pro His Ala
    1145                1150                1155
Ile Val Ile Leu Pro Lys Thr Asp Gly Met Glu Met Leu Val Cys
    1160                1165                1170
Tyr Glu Asp Glu Gly Val Tyr Val Asn Thr Tyr Gly Arg Ile Thr
    1175                1180                1185
Lys Asp Val Val Leu Gln Trp Gly Glu Met Pro Thr Ser Val Ala
    1190                1195                1200
Tyr Ile His Ser Asn Gln Ile Met Gly Trp Gly Glu Lys Ala Ile
    1205                1210                1215
Glu Ile Arg Ser Val Glu Thr Gly His Leu Asp Gly Val Phe Met
    1220                1225                1230
His Lys Arg Ala Gln Arg Leu Lys Phe Leu Cys Glu Arg Asn Asp
    1235                1240                1245
```

-continued

```
Lys Val Phe Phe Ala Ser Val Arg Ser Gly Gly Ser Ser Gln Val
    1250                1255                1260

Phe Phe Met Thr Leu Asn Arg Asn Ser Met Met Asn Trp Glx
    1265                1270                1275

<210> SEQ ID NO 13
<211> LENGTH: 1324
<212> TYPE: PRT
<213> ORGANISM: Artificial sequence
<220> FEATURE:
<223> OTHER INFORMATION: synthetic

<400> SEQUENCE: 13

Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
                20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Gly Asp Glu Glu Glu
        50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190

Tyr Trp Met Ala Pro Glu Val Ile Ala Cys Asp Glu Asn Pro Asp Ala
        195                 200                 205

Thr Tyr Asp Phe Lys Ser Asp Leu Trp Ser Leu Gly Ile Thr Ala Ile
    210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
                245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
        275                 280                 285

Ile Arg Asp Gln Pro Asn Glu Arg Gln Val Arg Ile Gln Leu Lys Asp
    290                 295                 300

His Ile Asp Arg Thr Lys Lys Arg Gly Glu Lys Asp Glu Thr Glu
305                 310                 315                 320

Tyr Glu Tyr Ser Gly Ser Glu Glu Glu Glu Asn Asp Ser Gly
                325                 330                 335
```

-continued

```
Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
            355                 360                 365

Arg Arg Gln Gln Leu Glu Gln Gln Arg Glu Asn Glu Glu His Lys
            370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Gln Arg Arg Glu Lys Glu Leu Arg
                405                 410                 415

Lys Gln Gln Glu Arg Glu Gln Arg Arg His Tyr Glu Glu Gln Met Arg
            420                 425                 430

Arg Glu Glu Arg Arg Ala Glu His Glu Gln Glu Tyr Lys Arg
            435                 440                 445

Lys Gln Leu Glu Glu Gln Arg Gln Ala Glu Arg Leu Gln Arg Gln Leu
            450                 455                 460

Lys Gln Glu Arg Asp Tyr Leu Val Ser Leu Gln His Gln Arg Gln Glu
465                 470                 475                 480

Gln Arg Pro Val Glu Lys Lys Pro Leu Tyr His Tyr Lys Glu Gly Met
                485                 490                 495

Ser Pro Ser Glu Lys Pro Ala Trp Ala Lys Glu Val Glu Glu Arg Ser
            500                 505                 510

Arg Leu Asn Arg Gln Ser Ser Pro Ala Met Pro His Lys Val Ala Asn
            515                 520                 525

Arg Ile Ser Asp Pro Asn Leu Pro Pro Arg Ser Glu Ser Phe Ser Ile
            530                 535                 540

Ser Gly Val Gln Pro Ala Arg Thr Pro Pro Met Leu Arg Pro Val Asp
545                 550                 555                 560

Pro Gln Ile Pro His Leu Val Ala Val Lys Ser Gln Gly Pro Ala Leu
                565                 570                 575

Thr Ala Ser Gln Ser Val His Glu Gln Pro Thr Lys Gly Leu Ser Gly
            580                 585                 590

Phe Gln Glu Ala Leu Asn Val Thr Ser His Arg Val Glu Met Pro Arg
            595                 600                 605

Gln Asn Ser Asp Pro Thr Ser Glu Asn Pro Pro Leu Pro Thr Arg Ile
            610                 615                 620

Glu Lys Phe Asp Arg Ser Ser Trp Leu Arg Gln Glu Glu Asp Ile Pro
625                 630                 635                 640

Pro Lys Val Pro Gln Arg Thr Thr Ser Ile Ser Pro Ala Leu Ala Arg
                645                 650                 655

Lys Asn Ser Pro Gly Asn Gly Ser Ala Leu Gly Pro Arg Leu Gly Ser
            660                 665                 670

Gln Pro Ile Arg Ala Ser Asn Pro Asp Leu Arg Arg Thr Glu Pro Ile
            675                 680                 685

Leu Glu Ser Pro Leu Gln Arg Thr Ser Ser Gly Ser Ser Ser Ser
            690                 695                 700

Ser Thr Pro Ser Ser Gln Pro Ser Ser Gln Gly Ser Gln Pro Gly
705                 710                 715                 720

Ser Gln Ala Gly Ser Ser Glu Arg Thr Arg Val Arg Ala Asn Ser Lys
                725                 730                 735

Ser Glu Gly Ser Pro Val Leu Pro His Glu Pro Ala Lys Val Lys Pro
            740                 745                 750

Glu Glu Ser Arg Asp Ile Thr Arg Pro Ser Arg Pro Ala Asp Leu Thr
```

-continued

```
            755                 760                 765
Ala Leu Ala Lys Glu Leu Arg Glu Leu Arg Ile Glu Glu Thr Asn Arg
    770                 775                 780

Pro Met Lys Lys Val Thr Asp Tyr Ser Ser Ser Glu Glu Ser Glu
785                 790                 795                 800

Ser Ser Glu Glu Glu Glu Asp Gly Glu Ser Glu Thr His Asp Gly
                805                 810                 815

Thr Val Ala Val Ser Asp Ile Pro Arg Leu Ile Pro Thr Gly Ala Pro
            820                 825                 830

Gly Ser Asn Glu Gln Tyr Asn Val Gly Met Val Gly Thr His Gly Leu
            835                 840                 845

Glu Thr Ser His Ala Asp Ser Phe Ser Gly Ser Ile Ser Arg Glu Gly
    850                 855                 860

Thr Leu Met Ile Arg Glu Thr Ser Gly Glu Lys Lys Arg Ser Gly His
865                 870                 875                 880

Ser Asp Ser Asn Gly Phe Ala Gly His Ile Asn Leu Pro Asp Leu Val
                885                 890                 895

Gln Gln Ser His Ser Pro Ala Gly Thr Pro Thr Glu Gly Leu Gly Arg
            900                 905                 910

Val Ser Thr His Ser Gln Glu Met Asp Ser Gly Thr Glu Tyr Gly Met
            915                 920                 925

Gly Ser Ser Thr Lys Ala Ser Phe Thr Pro Phe Val Asp Pro Arg Val
    930                 935                 940

Tyr Gln Thr Ser Pro Thr Asp Glu Asp Glu Glu Asp Glu Glu Ser Ser
945                 950                 955                 960

Ala Ala Ala Leu Phe Thr Ser Glu Leu Leu Arg Gln Glu Gln Ala Lys
                965                 970                 975

Leu Asn Glu Ala Arg Lys Ile Ser Val Val Asn Val Asn Pro Thr Asn
            980                 985                 990

Ile Arg Pro His Ser Asp Thr Pro  Glu Ile Arg Lys Tyr  Lys Lys Arg
            995                 1000                1005

Phe Asn  Ser Glu Ile Leu Cys  Ala Ala Leu Trp Gly  Val Asn Leu
    1010                1015                1020

Leu Val  Gly Thr Glu Asn Gly  Leu Met Leu Leu Asp  Arg Ser Gly
    1025                1030                1035

Gln Gly  Lys Val Tyr Asn Leu  Ile Asn Arg Arg Arg  Phe Gln Gln
    1040                1045                1050

Met Asp  Val Leu Glu Gly Leu  Asn Val Leu Val Thr  Ile Ser Gly
    1055                1060                1065

Lys Lys  Asn Lys Leu Arg Val  Tyr Tyr Leu Ser Trp  Leu Arg Asn
    1070                1075                1080

Arg Ile  Leu His Asn Asp Pro  Glu Val Glu Lys Lys  Gln Gly Trp
    1085                1090                1095

Ile Thr  Val Gly Asp Leu Glu  Gly Cys Ile His Tyr  Lys Val Val
    1100                1105                1110

Lys Tyr  Glu Arg Ile Lys Phe  Leu Val Ile Ala Leu  Lys Asn Ala
    1115                1120                1125

Val Glu  Ile Tyr Ala Trp Ala  Pro Lys Pro Tyr His  Lys Phe Met
    1130                1135                1140

Ala Phe  Lys Ser Phe Ala Asp  Leu Gln His Lys Pro  Leu Leu Val
    1145                1150                1155

Asp Leu  Thr Val Glu Glu Gly  Gln Arg Leu Lys Val  Ile Phe Gly
    1160                1165                1170
```

```
Ser His Thr Gly Phe His Val Ile Asp Val Asp Ser Gly Asn Ser
    1175                1180                1185

Tyr Asp Ile Tyr Ile Pro Ser His Ile Gln Gly Asn Ile Thr Pro
    1190                1195                1200

His Ala Ile Val Ile Leu Pro Lys Thr Asp Gly Met Glu Met Leu
    1205                1210                1215

Val Cys Tyr Glu Asp Glu Gly Val Tyr Val Asn Thr Tyr Gly Arg
    1220                1225                1230

Ile Thr Lys Asp Val Val Leu Gln Trp Gly Glu Met Pro Thr Ser
    1235                1240                1245

Val Ala Tyr Ile His Ser Asn Gln Ile Met Gly Trp Gly Glu Lys
    1250                1255                1260

Ala Ile Glu Ile Arg Ser Val Glu Thr Gly His Leu Asp Gly Val
    1265                1270                1275

Phe Met His Lys Arg Ala Gln Arg Leu Lys Phe Leu Cys Glu Arg
    1280                1285                1290

Asn Asp Lys Val Phe Phe Ala Ser Val Arg Ser Gly Gly Ser Ser
    1295                1300                1305

Gln Val Phe Phe Met Thr Leu Asn Arg Asn Ser Met Met Asn Trp
    1310                1315                1320

Glx

<210> SEQ ID NO 14
<211> LENGTH: 1298
<212> TYPE: PRT
<213> ORGANISM: Artificial sequence
<220> FEATURE:
<223> OTHER INFORMATION: synthetic

<400> SEQUENCE: 14

Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
                20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Gly Asp Glu Glu Glu
        50                  55                  60

Glu Ile Lys Gln Glu Ile Asn Met Leu Lys Lys Tyr Ser His His Arg
65                  70                  75                  80

Asn Ile Ala Thr Tyr Tyr Gly Ala Phe Ile Lys Lys Asn Pro Pro Gly
                85                  90                  95

Met Asp Asp Gln Leu Trp Leu Val Met Glu Phe Cys Gly Ala Gly Ser
            100                 105                 110

Val Thr Asp Leu Ile Lys Asn Thr Lys Gly Asn Thr Leu Lys Glu Glu
        115                 120                 125

Trp Ile Ala Tyr Ile Cys Arg Glu Ile Leu Arg Gly Leu Ser His Leu
    130                 135                 140

His Gln His Lys Val Ile His Arg Asp Ile Lys Gly Gln Asn Val Leu
145                 150                 155                 160

Leu Thr Glu Asn Ala Glu Val Lys Leu Val Asp Phe Gly Val Ser Ala
                165                 170                 175

Gln Leu Asp Arg Thr Val Gly Arg Arg Asn Thr Phe Ile Gly Thr Pro
            180                 185                 190
```

-continued

```
Tyr Trp Met Ala Pro Glu Val Ile Ala Cys Asp Glu Asn Pro Asp Ala
            195                 200                 205

Thr Tyr Asp Phe Lys Ser Asp Leu Trp Ser Leu Gly Ile Thr Ala Ile
            210                 215                 220

Glu Met Ala Glu Gly Ala Pro Pro Leu Cys Asp Met His Pro Met Arg
225                 230                 235                 240

Ala Leu Phe Leu Ile Pro Arg Asn Pro Ala Pro Arg Leu Lys Ser Lys
            245                 250                 255

Lys Trp Ser Lys Lys Phe Gln Ser Phe Ile Glu Ser Cys Leu Val Lys
            260                 265                 270

Asn His Ser Gln Arg Pro Ala Thr Glu Gln Leu Met Lys His Pro Phe
            275                 280                 285

Ile Arg Asp Gln Pro Asn Glu Arg Gln Val Arg Ile Gln Leu Lys Asp
            290                 295                 300

His Ile Asp Arg Thr Lys Lys Arg Gly Glu Lys Asp Glu Thr Glu
305                 310                 315                 320

Tyr Glu Tyr Ser Gly Ser Glu Glu Glu Glu Asn Asp Ser Gly
            325                 330                 335

Glu Pro Ser Ser Ile Leu Asn Leu Pro Gly Glu Ser Thr Leu Arg Arg
            340                 345                 350

Asp Phe Leu Arg Leu Gln Leu Ala Asn Lys Glu Arg Ser Glu Ala Leu
            355                 360                 365

Arg Arg Gln Gln Leu Glu Gln Gln Arg Glu Asn Glu Glu His Lys
370                 375                 380

Arg Gln Leu Leu Ala Glu Arg Gln Lys Arg Ile Glu Glu Gln Lys Glu
385                 390                 395                 400

Gln Arg Arg Arg Leu Glu Glu Gln Gln Arg Arg Glu Lys Glu Leu Arg
            405                 410                 415

Lys Gln Gln Glu Arg Glu Gln Arg Arg His Tyr Glu Gln Met Arg
            420                 425                 430

Arg Glu Glu Glu Arg Arg Arg Ala Glu His Glu Gln Glu Tyr Ile Arg
            435                 440                 445

Arg Gln Leu Glu Glu Glu Gln Arg Gln Leu Glu Ile Leu Gln Gln Gln
            450                 455                 460

Leu Leu His Glu Gln Ala Leu Leu Leu Glu Tyr Lys Arg Lys Gln Leu
465                 470                 475                 480

Glu Glu Gln Arg Gln Ala Glu Arg Leu Gln Arg Gln Leu Lys Gln Glu
            485                 490                 495

Arg Asp Tyr Leu Val Ser Leu Gln His Gln Arg Gln Glu Gln Arg Pro
            500                 505                 510

Val Glu Lys Lys Pro Leu Tyr His Tyr Lys Glu Gly Met Ser Pro Ser
            515                 520                 525

Glu Lys Pro Ala Trp Ala Lys Glu Ile Pro His Leu Val Ala Val Lys
530                 535                 540

Ser Gln Gly Pro Ala Leu Thr Ala Ser Gln Ser Val His Glu Gln Pro
545                 550                 555                 560

Thr Lys Gly Leu Ser Gly Phe Gln Glu Ala Leu Asn Val Thr Ser His
            565                 570                 575

Arg Val Glu Met Pro Arg Gln Asn Ser Asp Pro Thr Ser Glu Asn Pro
            580                 585                 590

Pro Leu Pro Thr Arg Ile Glu Lys Phe Asp Arg Ser Ser Trp Leu Arg
            595                 600                 605

Gln Glu Glu Asp Ile Pro Pro Lys Val Pro Gln Arg Thr Thr Ser Ile
```

-continued

```
            610                 615                 620
Ser Pro Ala Leu Ala Arg Lys Asn Ser Pro Gly Asn Gly Ser Ala Leu
625                 630                 635                 640
Gly Pro Arg Leu Gly Ser Gln Pro Ile Arg Ala Ser Asn Pro Asp Leu
                    645                 650                 655
Arg Arg Thr Glu Pro Ile Leu Glu Ser Pro Leu Gln Arg Thr Ser Ser
                    660                 665                 670
Gly Ser Ser Ser Ser Ser Thr Pro Ser Ser Gln Pro Ser Ser Gln
                    675                 680                 685
Gly Gly Ser Gln Pro Gly Ser Gln Ala Gly Ser Ser Glu Arg Thr Arg
            690                 695                 700
Val Arg Ala Asn Ser Lys Ser Glu Gly Ser Pro Val Leu Pro His Glu
705                 710                 715                 720
Pro Ala Lys Val Lys Pro Glu Glu Ser Arg Asp Ile Thr Arg Pro Ser
                    725                 730                 735
Arg Pro Ala Asp Leu Thr Ala Leu Ala Lys Glu Leu Arg Glu Leu Arg
                    740                 745                 750
Ile Glu Glu Thr Asn Arg Pro Met Lys Lys Val Thr Asp Tyr Ser Ser
            755                 760                 765
Ser Ser Glu Glu Ser Glu Ser Ser Glu Glu Glu Glu Asp Gly Glu
770                 775                 780
Ser Glu Thr His Asp Gly Thr Val Ala Val Ser Asp Ile Pro Arg Leu
785                 790                 795                 800
Ile Pro Thr Gly Ala Pro Gly Ser Asn Glu Gln Tyr Asn Val Gly Met
                    805                 810                 815
Val Gly Thr His Gly Leu Glu Thr Ser His Ala Asp Ser Phe Ser Gly
            820                 825                 830
Ser Ile Ser Arg Glu Gly Thr Leu Met Ile Arg Glu Thr Ser Gly Glu
            835                 840                 845
Lys Lys Arg Ser Gly His Ser Asp Ser Asn Gly Phe Ala Gly His Ile
850                 855                 860
Asn Leu Pro Asp Leu Val Gln Gln Ser His Ser Pro Ala Gly Thr Pro
865                 870                 875                 880
Thr Glu Gly Leu Gly Arg Val Ser Thr His Ser Gln Glu Met Asp Ser
                    885                 890                 895
Gly Thr Glu Tyr Gly Met Gly Ser Ser Thr Lys Ala Ser Phe Thr Pro
            900                 905                 910
Phe Val Asp Pro Arg Val Tyr Gln Thr Ser Pro Thr Asp Glu Asp Glu
            915                 920                 925
Glu Asp Glu Glu Ser Ser Ala Ala Ala Leu Phe Thr Ser Glu Leu Leu
            930                 935                 940
Arg Gln Glu Gln Ala Lys Leu Asn Glu Ala Arg Lys Ile Ser Val Val
945                 950                 955                 960
Asn Val Asn Pro Thr Asn Ile Arg Pro His Ser Asp Thr Pro Glu Ile
                    965                 970                 975
Arg Lys Tyr Lys Lys Arg Phe Asn Ser Glu Ile Leu Cys Ala Ala Leu
            980                 985                 990
Trp Gly Val Asn Leu Leu Val Gly  Thr Glu Asn Gly Leu  Met Leu Leu
            995                 1000                1005
Asp Arg  Ser Gly Gln Gly Lys  Val Tyr Asn Leu Ile  Asn Arg Arg
        1010                1015                1020
Arg Phe  Gln Gln Met Asp Val  Leu Glu Gly Leu Asn  Val Leu Val
        1025                1030                1035
```

-continued

```
Thr Ile Ser Gly Lys Lys Asn Lys Leu Arg Val Tyr Tyr Leu Ser
    1040                1045                1050

Trp Leu Arg Asn Arg Ile Leu His Asn Asp Pro Glu Val Glu Lys
    1055                1060                1065

Lys Gln Gly Trp Ile Thr Val Gly Asp Leu Gly Cys Ile His
    1070                1075                1080

Tyr Lys Val Val Lys Tyr Glu Arg Ile Lys Phe Leu Val Ile Ala
    1085                1090                1095

Leu Lys Asn Ala Val Glu Ile Tyr Ala Trp Ala Pro Lys Pro Tyr
    1100                1105                1110

His Lys Phe Met Ala Phe Lys Ser Phe Ala Asp Leu Gln His Lys
    1115                1120                1125

Pro Leu Leu Val Asp Leu Thr Val Glu Glu Gly Gln Arg Leu Lys
    1130                1135                1140

Val Ile Phe Gly Ser His Thr Gly Phe His Val Ile Asp Val Asp
    1145                1150                1155

Ser Gly Asn Ser Tyr Asp Ile Tyr Ile Pro Ser His Ile Gln Gly
    1160                1165                1170

Asn Ile Thr Pro His Ala Ile Val Ile Leu Pro Lys Thr Asp Gly
    1175                1180                1185

Met Glu Met Leu Val Cys Tyr Glu Asp Glu Gly Val Tyr Val Asn
    1190                1195                1200

Thr Tyr Gly Arg Ile Thr Lys Asp Val Val Leu Gln Trp Gly Glu
    1205                1210                1215

Met Pro Thr Ser Val Ala Tyr Ile His Ser Asn Gln Ile Met Gly
    1220                1225                1230

Trp Gly Glu Lys Ala Ile Glu Ile Arg Ser Val Glu Thr Gly His
    1235                1240                1245

Leu Asp Gly Val Phe Met His Lys Arg Ala Gln Arg Leu Lys Phe
    1250                1255                1260

Leu Cys Glu Arg Asn Asp Lys Val Phe Phe Ala Ser Val Arg Ser
    1265                1270                1275

Gly Gly Ser Ser Gln Val Phe Phe Met Thr Leu Asn Arg Asn Ser
    1280                1285                1290

Met Met Asn Trp Glx
    1295

<210> SEQ ID NO 15
<211> LENGTH: 1269
<212> TYPE: PRT
<213> ORGANISM: Artificial sequence
<220> FEATURE:
<223> OTHER INFORMATION: synthetic

<400> SEQUENCE: 15

Met Ala Ser Asp Ser Pro Ala Arg Ser Leu Asp Glu Ile Asp Leu Ser
1               5                   10                  15

Ala Leu Arg Asp Pro Ala Gly Ile Phe Glu Leu Val Glu Leu Val Gly
                20                  25                  30

Asn Gly Thr Tyr Gly Gln Val Tyr Lys Gly Arg His Val Lys Thr Gly
            35                  40                  45

Gln Leu Ala Ala Ile Lys Val Met Asp Val Thr Gly Asp Glu Glu Glu
        50                  55                  60

Glu Ile Lys Gln Glu Ile Asn Met Leu Lys Lys Tyr Ser His His Arg
65                  70                  75                  80
```

-continued

```
Asn Ile Ala Thr Tyr Tyr Gly Ala Phe Ile Lys Lys Asn Pro Pro Gly
                 85                  90                  95
Met Asp Asp Gln Leu Trp Leu Val Met Glu Phe Cys Gly Ala Gly Ser
             100                 105                 110
Val Thr Asp Leu Ile Lys Asn Thr Lys Gly Asn Thr Leu Lys Glu Glu
             115                 120                 125
Trp Ile Ala Tyr Ile Cys Arg Glu Ile Leu Arg Gly Leu Ser His Leu
             130                 135                 140
His Gln His Lys Val Ile His Arg Asp Ile Lys Gly Gln Asn Val Leu
145                 150                 155                 160
Leu Thr Glu Asn Ala Glu Val Lys Leu Val Asp Phe Gly Val Ser Ala
                 165                 170                 175
Gln Leu Asp Arg Thr Val Gly Arg Arg Asn Thr Phe Ile Gly Thr Pro
             180                 185                 190
Tyr Trp Met Ala Pro Glu Val Ile Ala Cys Asp Glu Asn Pro Asp Ala
             195                 200                 205
Thr Tyr Asp Phe Lys Ser Asp Leu Trp Ser Leu Gly Ile Thr Ala Ile
             210                 215                 220
Glu Met Ala Glu Gly Ala Pro Pro Leu Cys Asp Met His Pro Met Arg
225                 230                 235                 240
Ala Leu Phe Leu Ile Pro Arg Asn Pro Ala Pro Arg Leu Lys Ser Lys
                 245                 250                 255
Lys Trp Ser Lys Lys Phe Gln Ser Phe Ile Glu Ser Cys Leu Val Lys
             260                 265                 270
Asn His Ser Gln Arg Pro Ala Thr Glu Gln Leu Met Lys His Pro Phe
             275                 280                 285
Ile Arg Asp Gln Pro Asn Glu Arg Gln Val Arg Ile Gln Leu Lys Asp
             290                 295                 300
His Ile Asp Arg Thr Lys Lys Arg Gly Glu Lys Asp Glu Thr Glu
305                 310                 315                 320
Tyr Glu Tyr Ser Gly Ser Glu Glu Glu Glu Asn Asp Ser Gly
             325                 330                 335
Glu Pro Ser Ser Ile Leu Asn Leu Pro Gly Glu Ser Thr Leu Arg Arg
             340                 345                 350
Asp Phe Leu Arg Leu Gln Leu Ala Asn Lys Glu Arg Ser Glu Ala Leu
             355                 360                 365
Arg Arg Gln Gln Leu Glu Gln Gln Gln Arg Glu Asn Glu Glu His Lys
             370                 375                 380
Arg Gln Leu Leu Ala Glu Arg Gln Lys Arg Ile Glu Glu Gln Lys Glu
385                 390                 395                 400
Gln Arg Arg Arg Leu Glu Glu Gln Gln Arg Arg Glu Lys Glu Leu Arg
             405                 410                 415
Lys Gln Gln Glu Arg Glu Gln Arg Arg His Tyr Glu Glu Gln Met Arg
             420                 425                 430
Arg Glu Glu Glu Arg Arg Arg Ala Glu His Glu Gln Glu Tyr Lys Arg
             435                 440                 445
Lys Gln Leu Glu Glu Gln Arg Gln Ala Glu Arg Leu Gln Arg Gln Leu
             450                 455                 460
Lys Gln Glu Arg Asp Tyr Leu Val Ser Leu Gln His Gln Arg Gln Glu
465                 470                 475                 480
Gln Arg Pro Val Glu Lys Lys Pro Leu Tyr His Tyr Lys Glu Gly Met
             485                 490                 495
```

-continued

Ser Pro Ser Glu Lys Pro Ala Trp Ala Lys Glu Ile Pro His Leu Val
        500                 505                 510

Ala Val Lys Ser Gln Gly Pro Ala Leu Thr Ala Ser Gln Ser Val His
        515                 520                 525

Glu Gln Pro Thr Lys Gly Leu Ser Gly Phe Gln Glu Ala Leu Asn Val
        530                 535                 540

Thr Ser His Arg Val Glu Met Pro Arg Gln Asn Ser Asp Pro Thr Ser
545                 550                 555                 560

Glu Asn Pro Pro Leu Pro Thr Arg Ile Glu Lys Phe Asp Arg Ser Ser
                565                 570                 575

Trp Leu Arg Gln Glu Glu Asp Ile Pro Pro Lys Val Pro Gln Arg Thr
            580                 585                 590

Thr Ser Ile Ser Pro Ala Leu Ala Arg Lys Asn Ser Pro Gly Asn Gly
            595                 600                 605

Ser Ala Leu Gly Pro Arg Leu Gly Ser Gln Pro Ile Arg Ala Ser Asn
        610                 615                 620

Pro Asp Leu Arg Arg Thr Glu Pro Ile Leu Glu Ser Pro Leu Gln Arg
625                 630                 635                 640

Thr Ser Ser Gly Ser Ser Ser Ser Ser Thr Pro Ser Ser Gln Pro
                645                 650                 655

Ser Ser Gln Gly Gly Ser Gln Pro Gly Ser Gln Ala Gly Ser Ser Glu
        660                 665                 670

Arg Thr Arg Val Arg Ala Asn Ser Lys Ser Glu Gly Ser Pro Val Leu
        675                 680                 685

Pro His Glu Pro Ala Lys Val Lys Pro Glu Glu Ser Arg Asp Ile Thr
        690                 695                 700

Arg Pro Ser Arg Pro Ala Asp Leu Thr Ala Leu Ala Lys Glu Leu Arg
705                 710                 715                 720

Glu Leu Arg Ile Glu Glu Thr Asn Arg Pro Met Lys Lys Val Thr Asp
                725                 730                 735

Tyr Ser Ser Ser Ser Glu Glu Ser Glu Ser Ser Glu Glu Glu Glu
            740                 745                 750

Asp Gly Glu Ser Glu Thr His Asp Gly Thr Val Ala Val Ser Asp Ile
        755                 760                 765

Pro Arg Leu Ile Pro Thr Gly Ala Pro Gly Ser Asn Glu Gln Tyr Asn
        770                 775                 780

Val Gly Met Val Gly Thr His Gly Leu Glu Thr Ser His Ala Asp Ser
785                 790                 795                 800

Phe Ser Gly Ser Ile Ser Arg Glu Gly Thr Leu Met Ile Arg Glu Thr
                805                 810                 815

Ser Gly Glu Lys Lys Arg Ser Gly His Ser Asp Ser Asn Gly Phe Ala
            820                 825                 830

Gly His Ile Asn Leu Pro Asp Leu Val Gln Gln Ser His Ser Pro Ala
        835                 840                 845

Gly Thr Pro Thr Glu Gly Leu Gly Arg Val Ser Thr His Ser Gln Glu
        850                 855                 860

Met Asp Ser Gly Thr Glu Tyr Gly Met Gly Ser Ser Thr Lys Ala Ser
865                 870                 875                 880

Phe Thr Pro Phe Val Asp Pro Arg Val Tyr Gln Thr Ser Pro Thr Asp
                885                 890                 895

Glu Asp Glu Glu Asp Glu Glu Ser Ala Ala Ala Leu Phe Thr Ser
            900                 905                 910

Glu Leu Leu Arg Gln Glu Gln Ala Lys Leu Asn Glu Ala Arg Lys Ile

```
                      915                 920                 925
Ser  Val  Val  Asn  Val  Asn  Pro  Thr  Asn  Ile  Arg  Pro  His  Ser  Asp  Thr
     930                 935                 940

Pro  Glu  Ile  Arg  Lys  Tyr  Lys  Lys  Arg  Phe  Asn  Ser  Glu  Ile  Leu  Cys
945                      950                 955                      960

Ala  Ala  Leu  Trp  Gly  Val  Asn  Leu  Leu  Val  Gly  Thr  Glu  Asn  Gly  Leu
               965                 970                      975

Met  Leu  Leu  Asp  Arg  Ser  Gly  Gln  Gly  Lys  Val  Tyr  Asn  Leu  Ile  Asn
          980                 985                      990

Arg  Arg  Arg  Phe  Gln  Gln  Met  Asp  Val  Leu  Glu  Gly  Leu  Asn  Val  Leu
          995                 1000                     1005

Val  Thr  Ile  Ser  Gly  Lys  Lys  Asn  Lys  Leu  Arg  Val  Tyr  Tyr  Leu
     1010                1015                1020

Ser  Trp  Leu  Arg  Asn  Arg  Ile  Leu  His  Asn  Asp  Pro  Glu  Val  Glu
     1025                1030                1035

Lys  Lys  Gln  Gly  Trp  Ile  Thr  Val  Gly  Asp  Leu  Glu  Gly  Cys  Ile
     1040                1045                1050

His  Tyr  Lys  Val  Val  Lys  Tyr  Glu  Arg  Ile  Lys  Phe  Leu  Val  Ile
     1055                1060                1065

Ala  Leu  Lys  Asn  Ala  Val  Glu  Ile  Tyr  Ala  Trp  Ala  Pro  Lys  Pro
     1070                1075                1080

Tyr  His  Lys  Phe  Met  Ala  Phe  Lys  Ser  Phe  Ala  Asp  Leu  Gln  His
     1085                1090                1095

Lys  Pro  Leu  Leu  Val  Asp  Leu  Thr  Val  Glu  Glu  Gly  Gln  Arg  Leu
     1100                1105                1110

Lys  Val  Ile  Phe  Gly  Ser  His  Thr  Gly  Phe  His  Val  Ile  Asp  Val
     1115                1120                1125

Asp  Ser  Gly  Asn  Ser  Tyr  Asp  Ile  Tyr  Ile  Pro  Ser  His  Ile  Gln
     1130                1135                1140

Gly  Asn  Ile  Thr  Pro  His  Ala  Ile  Val  Ile  Leu  Pro  Lys  Thr  Asp
     1145                1150                1155

Gly  Met  Glu  Met  Leu  Val  Cys  Tyr  Glu  Asp  Glu  Gly  Val  Tyr  Val
     1160                1165                1170

Asn  Thr  Tyr  Gly  Arg  Ile  Thr  Lys  Asp  Val  Val  Leu  Gln  Trp  Gly
     1175                1180                1185

Glu  Met  Pro  Thr  Ser  Val  Ala  Tyr  Ile  His  Ser  Asn  Gln  Ile  Met
     1190                1195                1200

Gly  Trp  Gly  Glu  Lys  Ala  Ile  Glu  Ile  Arg  Ser  Val  Glu  Thr  Gly
     1205                1210                1215

His  Leu  Asp  Gly  Val  Phe  Met  His  Lys  Arg  Ala  Gln  Arg  Leu  Lys
     1220                1225                1230

Phe  Leu  Cys  Glu  Arg  Asn  Asp  Lys  Val  Phe  Phe  Ala  Ser  Val  Arg
     1235                1240                1245

Ser  Gly  Gly  Ser  Ser  Gln  Val  Phe  Phe  Met  Thr  Leu  Asn  Arg  Asn
     1250                1255                1260

Ser  Met  Met  Asn  Trp  Glx
     1265
```

<210> SEQ ID NO 16
<211> LENGTH: 9
<212> TYPE: PRT
<213> ORGANISM: Artificial sequence
<220> FEATURE:
<223> OTHER INFORMATION: synthetic -continued

```
<400> SEQUENCE: 16

Arg Thr Val Leu Gly Val Ile Gly Asp
1               5

<210> SEQ ID NO 17
<211> LENGTH: 9
<212> TYPE: PRT
<213> ORGANISM: Artificial Sequence
<220> FEATURE:
<223> OTHER INFORMATION: synthetic

<400> SEQUENCE: 17

Arg Thr Ala Leu Gly Asp Ile Gly Asn
1               5

<210> SEQ ID NO 18
<211> LENGTH: 27
<212> TYPE: PRT
<213> ORGANISM: Rattus sp.

<400> SEQUENCE: 18

Tyr Met Thr Val Ser Ile Ile Asp Arg Phe Met Gln Asp Ser Cys Val
1               5                   10                  15

Pro Lys Lys Met Leu Gln Leu Val Gly Val Thr
            20                  25

<210> SEQ ID NO 19
<211> LENGTH: 28
<212> TYPE: PRT
<213> ORGANISM: Mus sp.

<400> SEQUENCE: 19

Lys Phe Arg Leu Leu Gln Glu Thr Met Tyr Met Thr Val Ser Ile Ile
1               5                   10                  15

Asp Arg Phe Met Gln Asn Ser Cys Val Pro Lys Lys
            20                  25

<210> SEQ ID NO 20
<211> LENGTH: 27
<212> TYPE: PRT
<213> ORGANISM: Mus sp.

<400> SEQUENCE: 20

Arg Ala Ile Leu Ile Asp Trp Leu Ile Gln Val Gln Met Lys Phe Arg
1               5                   10                  15

Leu Leu Gln Glu Thr Met Tyr Met Thr Val Ser
            20                  25

<210> SEQ ID NO 21
<211> LENGTH: 27
<212> TYPE: PRT
<213> ORGANISM: Mus sp.

<400> SEQUENCE: 21

Asp Arg Phe Leu Gln Ala Gln Leu Val Cys Arg Lys Lys Leu Gln Val
1               5                   10                  15

Val Gly Ile Thr Ala Leu Leu Leu Ala Ser Lys
            20                  25

<210> SEQ ID NO 22
<211> LENGTH: 18
<212> TYPE: PRT
<213> ORGANISM: Mus sp.
```

<400> SEQUENCE: 22

Met Ser Val Leu Arg Gly Lys Leu Gln Leu Val Gly Thr Ala Ala Met
1               5                   10                  15

Leu Leu

<210> SEQ ID NO 23
<211> LENGTH: 26
<212> TYPE: DNA
<213> ORGANISM: Artificial sequence
<220> FEATURE:
<223> OTHER INFORMATION: synthetic

<400> SEQUENCE: 23
tgcgcttata ttccagaagt agagct                                   26

<210> SEQ ID NO 24
<211> LENGTH: 20
<212> TYPE: DNA
<213> ORGANISM: Artificial sequence
<220> FEATURE:
<223> OTHER INFORMATION: synthetic

<400> SEQUENCE: 24
ctgtctctgc tcctcctcta                                          20

<210> SEQ ID NO 25
<211> LENGTH: 10
<212> TYPE: PRT
<213> ORGANISM: Artificial sequence
<220> FEATURE:
<223> OTHER INFORMATION: synthetic

<400> SEQUENCE: 25

Ala Tyr Pro Tyr Asp Val Pro Asp Tyr Ala
1               5                   10

<210> SEQ ID NO 26
<211> LENGTH: 31
<212> TYPE: DNA
<213> ORGANISM: Artificial sequence
<220> FEATURE:
<223> OTHER INFORMATION: synthetic

<400> SEQUENCE: 26
agcttgcagc catcagggtt atggatgtca c                             31

<210> SEQ ID NO 27
<211> LENGTH: 31
<212> TYPE: DNA
<213> ORGANISM: Artificial sequence
<220> FEATURE:
<223> OTHER INFORMATION: synthetic

<400> SEQUENCE: 27
gtgacatcca taaccttgat ggctgcaagc t                             31

<210> SEQ ID NO 28
<211> LENGTH: 9
<212> TYPE: PRT
<213> ORGANISM: Artificial sequence
<220> FEATURE:
<223> OTHER INFORMATION: synthetic

<400> SEQUENCE: 28

```
Asp Tyr Lys Asp Asp Asp Lys Gly
 1               5

<210> SEQ ID NO 29
<211> LENGTH: 14
<212> TYPE: PRT
<213> ORGANISM: Artificial sequence
<220> FEATURE:
<223> OTHER INFORMATION: synthetic

<400> SEQUENCE: 29

Ala Ser Met Glu Gln Lys Leu Ile Ser Glu Glu Asp Leu Asn
 1               5                  10

<210> SEQ ID NO 30
<211> LENGTH: 6
<212> TYPE: PRT
<213> ORGANISM: Artificial sequence
<220> FEATURE:
<223> OTHER INFORMATION: synthetic

<400> SEQUENCE: 30

Pro Cys Pro Pro Ser Arg
 1               5

<210> SEQ ID NO 31
<211> LENGTH: 6
<212> TYPE: PRT
<213> ORGANISM: Artificial sequence
<220> FEATURE:
<223> OTHER INFORMATION: synthetic

<400> SEQUENCE: 31

Pro Arg Val Pro Val Arg
 1               5

<210> SEQ ID NO 32
<211> LENGTH: 6
<212> TYPE: PRT
<213> ORGANISM: Artificial sequence
<220> FEATURE:
<223> OTHER INFORMATION: synthetic

<400> SEQUENCE: 32

Pro Asn Leu Pro Pro Arg
 1               5

<210> SEQ ID NO 33
<211> LENGTH: 6
<212> TYPE: PRT
<213> ORGANISM: Artificial sequence
<220> FEATURE:
<223> OTHER INFORMATION: synthetic

<400> SEQUENCE: 33

Pro Lys Val Pro Gln Arg
 1               5

<210> SEQ ID NO 34
<211> LENGTH: 1360
<212> TYPE: PRT
<213> ORGANISM: Artificial sequence
<220> FEATURE:
<223> OTHER INFORMATION: synthetic

<400> SEQUENCE: 34

Met Ala Ser Asp Ser Pro Ala Arg Ser Leu Asp Glu Ile Asp Leu Ser
```

```
1               5                  10                 15
Ala Leu Arg Asp Pro Ala Gly Ile Phe Glu Leu Val Glu Leu Val Gly
                20                 25                 30
Asn Gly Thr Tyr Gly Gln Val Tyr Lys Gly Arg His Val Lys Thr Gly
                35                 40                 45
Gln Leu Ala Ala Ile Lys Val Met Asp Val Thr Gly Asp Glu Glu Glu
                50                 55                 60
Glu Ile Lys Gln Glu Ile Asn Met Leu Lys Lys Tyr Ser His His Arg
65                         70                 75                 80
Asn Ile Ala Thr Tyr Tyr Gly Ala Phe Ile Lys Lys Asn Pro Pro Gly
                        85                 90                 95
Met Asp Asp Gln Leu Trp Leu Val Met Glu Phe Cys Gly Ala Gly Ser
                100                105                110
Val Thr Asp Leu Ile Lys Asn Thr Lys Gly Asn Thr Leu Lys Glu Glu
                115                120                125
Trp Ile Ala Tyr Ile Cys Arg Glu Ile Leu Arg Gly Leu Ser His Leu
130                        135                140
His Gln His Lys Val Ile His Arg Asp Ile Lys Gly Gln Asn Val Leu
145                        150                155                160
Leu Thr Glu Asn Ala Glu Val Lys Leu Val Asp Phe Gly Val Ser Ala
                165                170                175
Gln Leu Asp Arg Thr Val Gly Arg Arg Asn Thr Phe Ile Gly Thr Pro
                180                185                190
Tyr Trp Met Ala Pro Glu Val Ile Ala Cys Asp Glu Asn Pro Asp Ala
                195                200                205
Thr Tyr Asp Phe Lys Ser Asp Leu Trp Ser Leu Gly Ile Thr Ala Ile
                210                215                220
Glu Met Ala Glu Gly Ala Pro Pro Leu Cys Asp Met His Pro Met Arg
225                        230                235                240
Ala Leu Phe Leu Ile Pro Arg Asn Pro Ala Pro Arg Leu Lys Ser Lys
                245                250                255
Lys Trp Ser Lys Lys Phe Gln Ser Phe Ile Glu Ser Cys Leu Val Lys
                260                265                270
Asn His Ser Gln Arg Pro Ala Thr Glu Gln Leu Met Lys His Pro Phe
                275                280                285
Ile Arg Asp Gln Pro Asn Glu Arg Gln Val Arg Ile Gln Leu Lys Asp
                290                295                300
His Ile Asp Arg Thr Lys Lys Lys Arg Gly Glu Lys Asp Glu Thr Glu
305                        310                315                320
Tyr Glu Tyr Ser Gly Ser Glu Glu Glu Glu Asn Asp Ser Gly
                        325                330                335
Glu Pro Ser Ser Ile Leu Asn Leu Pro Gly Glu Ser Thr Leu Arg Arg
                340                345                350
Asp Phe Leu Arg Leu Gln Leu Ala Asn Lys Glu Arg Ser Glu Ala Leu
                355                360                365
Arg Arg Gln Gln Leu Glu Gln Gln Arg Glu Asn Glu Glu His Lys
                370                375                380
Arg Gln Leu Leu Ala Glu Arg Gln Lys Arg Ile Glu Glu Gln Lys Glu
385                        390                395                400
Gln Arg Arg Arg Leu Glu Glu Gln Arg Arg Glu Lys Glu Leu Arg
                        405                410                415
Lys Gln Gln Glu Arg Glu Gln Arg Arg His Tyr Glu Glu Gln Met Arg
                420                425                430
```

```
Arg Glu Glu Glu Arg Arg Ala Glu His Glu Gln Glu Tyr Ile Arg
        435                 440                 445

Arg Gln Leu Glu Glu Gln Arg Gln Leu Glu Ile Leu Gln Gln Gln
450                 455                 460

Leu Leu His Glu Gln Ala Leu Leu Glu Tyr Lys Arg Lys Gln Leu
465                 470                 475                 480

Glu Glu Gln Arg Gln Ala Glu Arg Leu Gln Arg Gln Leu Lys Gln Glu
                485                 490                 495

Arg Asp Tyr Leu Val Ser Leu Gln His Gln Arg Gln Glu Gln Arg Pro
            500                 505                 510

Val Glu Lys Lys Pro Leu Tyr His Tyr Lys Glu Gly Met Ser Pro Ser
        515                 520                 525

Glu Lys Pro Ala Trp Ala Lys Glu Val Glu Glu Arg Ser Arg Leu Asn
530                 535                 540

Arg Gln Ser Ser Pro Ala Met Pro His Lys Val Ala Asn Arg Ile Ser
545                 550                 555                 560

Asp Pro Asn Leu Pro Pro Arg Ser Glu Ser Phe Ser Ile Ser Gly Val
            565                 570                 575

Gln Pro Ala Arg Thr Pro Met Leu Arg Pro Val Asp Pro Gln Ile
        580                 585                 590

Pro His Leu Val Ala Val Lys Ser Gln Gly Pro Ala Leu Thr Ala Ser
        595                 600                 605

Gln Ser Val His Glu Gln Pro Thr Lys Gly Leu Ser Gly Phe Gln Glu
        610                 615                 620

Ala Leu Asn Val Thr Ser His Arg Val Glu Met Pro Arg Gln Asn Ser
625                 630                 635                 640

Asp Pro Thr Ser Glu Asn Pro Pro Leu Pro Thr Arg Ile Glu Lys Phe
            645                 650                 655

Asp Arg Ser Ser Trp Leu Arg Gln Glu Glu Asp Ile Pro Pro Lys Val
            660                 665                 670

Pro Gln Arg Thr Thr Ser Ile Ser Pro Ala Leu Ala Arg Lys Asn Ser
        675                 680                 685

Pro Gly Asn Gly Ser Ala Leu Gly Pro Arg Leu Gly Ser Gln Pro Ile
        690                 695                 700

Arg Ala Ser Asn Pro Asp Leu Arg Arg Thr Glu Pro Ile Leu Glu Ser
705                 710                 715                 720

Pro Leu Gln Arg Thr Ser Ser Gly Ser Ser Ser Ser Ser Ser Thr Pro
                725                 730                 735

Ser Ser Gln Pro Ser Ser Gln Gly Gly Ser Gln Pro Gly Ser Gln Ala
            740                 745                 750

Gly Ser Ser Glu Arg Thr Arg Val Arg Ala Asn Ser Lys Ser Glu Gly
        755                 760                 765

Ser Pro Val Leu Pro His Glu Pro Ala Lys Val Lys Pro Glu Glu Ser
        770                 775                 780

Arg Asp Ile Thr Arg Pro Ser Arg Pro Ala Ser Tyr Lys Lys Ala Ile
785                 790                 795                 800

Asp Glu Asp Leu Thr Ala Leu Ala Lys Glu Leu Arg Glu Leu Arg Ile
                805                 810                 815

Glu Glu Thr Asn Arg Pro Met Lys Lys Val Thr Asp Tyr Ser Ser Ser
            820                 825                 830

Ser Glu Glu Ser Glu Ser Ser Glu Glu Glu Glu Asp Gly Glu Ser
        835                 840                 845
```

-continued

Glu Thr His Asp Gly Thr Val Ala Val Ser Asp Ile Pro Arg Leu Ile
    850                 855                 860

Pro Thr Gly Ala Pro Gly Ser Asn Glu Gln Tyr Asn Val Gly Met Val
865                 870                 875                 880

Gly Thr His Gly Leu Glu Thr Ser His Ala Asp Ser Phe Ser Gly Ser
                885                 890                 895

Ile Ser Arg Glu Gly Thr Leu Met Ile Arg Glu Thr Ser Gly Glu Lys
                900                 905                 910

Lys Arg Ser Gly His Ser Asp Ser Asn Gly Phe Ala Gly His Ile Asn
            915                 920                 925

Leu Pro Asp Leu Val Gln Gln Ser His Ser Pro Ala Gly Thr Pro Thr
930                 935                 940

Glu Gly Leu Gly Arg Val Ser Thr His Ser Gln Glu Met Asp Ser Gly
945                 950                 955                 960

Thr Glu Tyr Gly Met Gly Ser Ser Thr Lys Ala Ser Phe Thr Pro Phe
                965                 970                 975

Val Asp Pro Arg Val Tyr Gln Thr Ser Pro Thr Asp Glu Asp Glu Glu
                980                 985                 990

Asp Glu Glu Ser Ser Ala Ala Ala Leu Phe Thr Ser Glu Leu Leu Arg
        995                 1000                1005

Gln Glu Gln Ala Lys Leu Asn Glu Ala Arg Lys Ile Ser Val Val
    1010            1015                1020

Asn Val Asn Pro Thr Asn Ile Arg Pro His Ser Asp Thr Pro Glu
    1025            1030                1035

Ile Arg Lys Tyr Lys Lys Arg Phe Asn Ser Glu Ile Leu Cys Ala
    1040            1045                1050

Ala Leu Trp Gly Val Asn Leu Leu Val Gly Thr Glu Asn Gly Leu
    1055            1060                1065

Met Leu Leu Asp Arg Ser Gly Gln Gly Lys Val Tyr Asn Leu Ile
    1070            1075                1080

Asn Arg Arg Arg Phe Gln Gln Met Asp Val Leu Glu Gly Leu Asn
    1085            1090                1095

Val Leu Val Thr Ile Ser Gly Lys Lys Asn Lys Leu Arg Val Tyr
    1100            1105                1110

Tyr Leu Ser Trp Leu Arg Asn Arg Ile Leu His Asn Asp Pro Glu
    1115            1120                1125

Val Glu Lys Lys Gln Gly Trp Ile Thr Val Gly Asp Leu Glu Gly
    1130            1135                1140

Cys Ile His Tyr Lys Val Val Lys Tyr Glu Arg Ile Lys Phe Leu
    1145            1150                1155

Val Ile Ala Leu Lys Asn Ala Val Glu Ile Tyr Ala Trp Ala Pro
    1160            1165                1170

Lys Pro Tyr His Lys Phe Met Ala Phe Lys Ser Phe Ala Asp Leu
    1175            1180                1185

Gln His Lys Pro Leu Leu Val Asp Leu Thr Val Glu Glu Gly Gln
    1190            1195                1200

Arg Leu Lys Val Ile Phe Gly Ser His Thr Gly Phe His Val Ile
    1205            1210                1215

Asp Val Asp Ser Gly Asn Ser Tyr Asp Ile Tyr Ile Pro Ser His
    1220            1225                1230

Ile Gln Gly Asn Ile Thr Pro His Ala Ile Val Ile Leu Pro Lys
    1235            1240                1245

Thr Asp Gly Met Glu Met Leu Val Cys Tyr Glu Asp Glu Gly Val

-continued

```
                1250                1255                1260

Tyr Val Asn Thr Tyr Gly Arg Ile Thr Lys Asp Val Val Leu Gln
                1265                1270                1275

Trp Gly Glu Met Pro Thr Ser Val Ala Tyr Ile His Ser Asn Gln
            1280                1285                1290

Ile Met Gly Trp Gly Glu Lys Ala Ile Glu Ile Arg Ser Val Glu
            1295                1300                1305

Thr Gly His Leu Asp Gly Val Phe Met His Lys Arg Ala Gln Arg
            1310                1315                1320

Leu Lys Phe Leu Cys Glu Arg Asn Asp Lys Val Phe Phe Ala Ser
            1325                1330                1335

Val Arg Ser Gly Gly Ser Ser Gln Val Phe Phe Met Thr Leu Asn
            1340                1345                1350

Arg Asn Ser Met Met Asn Trp
            1355                1360

<210> SEQ ID NO 35
<211> LENGTH: 1233
<212> TYPE: PRT
<213> ORGANISM: Artificial sequence
<220> FEATURE:
<223> OTHER INFORMATION: synthetic

<400> SEQUENCE: 35

Met Ala Asn Asp Ser Pro Ala Lys Ser Leu Val Glu Ile Asp Leu Ser
1               5                   10                  15

Ser Leu Arg Asp Pro Ala Gly Ile Phe Glu Val Val Glu Leu Val Gly
                20                  25                  30

Asn Gly Thr Tyr Gly Gln Val Tyr Lys Gly Arg His Val Lys Thr Val
            35                  40                  45

Thr Ala Ala Ile Lys Val Met Asp Val Thr Gly Asp Glu Glu Glu Glu
        50                  55                  60

Ile Thr Leu Glu Ile Asn Met Leu Lys Lys Tyr Ser His His Arg Asn
65                  70                  75                  80

Ile Ala Thr Tyr Tyr Gly Ala Phe Ile Lys Lys Ser Pro Pro Gly His
                85                  90                  95

Asp Asp Gln Leu Trp Leu Val Met Glu Phe Cys Gly Ala Gly Ser Ile
            100                 105                 110

Thr Asp Leu Ile Val Asn Thr Lys Gly Asn Thr Leu Lys Glu Asp Trp
        115                 120                 125

Ile Ala Tyr Ile Ser Arg Glu Ile Leu Arg Gly Leu Ala His Leu His
    130                 135                 140

Ile His His Val Ile His Arg Asp Ile Lys Gly Gln Asn Val Leu Leu
145                 150                 155                 160

Thr Glu Asn Ala Glu Val Lys Leu Val Asp Phe Gly Val Ser Ala Gln
                165                 170                 175

Leu Asp Arg Thr Val Gly Arg Arg Asn Thr Phe Ile Gly Thr Pro Tyr
            180                 185                 190

Trp Met Ala Pro Glu Val Ile Ala Cys Asp Glu Asn Pro Asp Ala Thr
        195                 200                 205

Tyr Asp Tyr Arg Ser Asp Leu Trp Ser Cys Gly Ile Thr Ala Ile Glu
    210                 215                 220

Met Ala Glu Gly Cys Pro Pro Leu Cys Asp Met His Pro Met Arg Ala
225                 230                 235                 240

Leu Phe Leu Ile Pro Arg Asn Pro Pro Arg Leu Lys Ser Lys Lys
```

-continued

```
                        245                 250                 255

Trp Ser Lys Lys Phe Ser Phe Ile Glu Gly Cys Leu Val Lys Asn
                260                 265                 270

Tyr Met Gln Arg Pro Ser Thr Glu Gln Leu Leu Lys His Pro Phe Ile
        275                 280                 285

Arg Asp Gln Pro Asn Glu Arg Gln Val Arg Ile Gln Leu Lys Asp His
    290                 295                 300

Ile Asp Arg Thr Arg Lys Lys Arg Gly Glu Lys Asp Glu Thr Glu Tyr
305                 310                 315                 320

Glu Tyr Ser Gly Ser Glu Glu Glu Glu Val Pro Glu Glu Gln
                325                 330                 335

Glu Gly Glu Pro Ser Ser Ile Val Asn Val Pro Gly Glu Ser Thr Leu
                340                 345                 350

Arg Arg Asp Phe Leu Arg Leu Gln Gln Glu Asn Lys Glu Arg Ser Glu
                355                 360                 365

Ala Leu Arg Arg Gln Gln Leu Ser Gln Glu Gln Leu Arg Glu Gln Glu
        370                 375                 380

Glu Tyr Lys Arg Gln Leu Leu Ala Glu Arg Gln Lys Arg Ile Glu Cys
385                 390                 395                 400

Gln Lys Glu Gln Arg Arg Arg Leu Glu Glu Gln Arg Arg Glu Arg
                405                 410                 415

Glu Ala Arg Arg Gln Gln Glu Arg Glu Gln Arg Arg Arg Glu Gln Glu
                420                 425                 430

Glu Lys Arg Arg Leu Glu Glu Leu Glu Arg Arg Lys Glu Glu Glu
                435                 440                 445

Glu Arg Arg Arg Ala Glu Glu Arg Arg Val Glu Arg Glu Gln
                450                 455                 460

Glu Tyr Ile Arg Arg Gln Leu Glu Glu Gln Arg His Leu Glu Ile
465                 470                 475                 480

Leu Gln Gln Gln Leu Leu Gln Glu Gln Ala Met Leu Leu His Asp His
                485                 490                 495

Arg His Pro His Ala Gln Gln Pro Pro Pro Gln Gln Asp
                500                 505                 510

Arg Ser Lys Pro Ser Ser His Ala Pro Glu Pro Lys Pro His Tyr Asp
                515                 520                 525

Pro Ala Asp Asn Ala Arg Glu Val Gln Trp Ser His Leu Ala Ser Leu
    530                 535                 540

Lys Asn Asn Val Ser Pro Val Ser Arg Ser His Ser Phe Ser Asp Val
545                 550                 555                 560

Pro Ser Lys Phe Ala Ala His His His Leu Arg Ser Gln Asp Pro Cys
                565                 570                 575

Pro Pro Ser Arg Ser Glu Gly Leu Ser Gln Ser Ser Asp Ser Lys Ser
                580                 585                 590

Glu Val Pro Glu Pro Thr Arg Gln Lys Ala Trp Ser Arg Ser Asp Ser
                595                 600                 605

Asp Glu Val Pro Pro Arg Val Pro Val Arg Thr Thr Ser Arg Ser Pro
    610                 615                 620

Val Leu Ser Arg Arg Asp Ser Pro Leu Gln Gly Gly Asn Ser Gln
625                 630                 635                 640

Ala Gly Gln Arg Asn Ser Thr Ser Ser Ile Glu Pro Pro Leu Leu Trp
                645                 650                 655

Glu Arg Val Glu Lys Leu Val Pro Arg Pro Gly Ser Gly Ser Ser Ser
                660                 665                 670
```

-continued

```
Gly Ser Ser Asn Ser Gly Ser Gln Pro Gly Ser His Pro Cys Ser Gln
            675                 680                 685
Ser Gly Ser Gly Glu Arg Phe Arg Val Arg Ser Ser Lys Ser Glu
        690                 695                 700
Gly Ser Pro Ser Pro Arg Gln Glu Ser Ala Ala Lys Lys Pro Asp Asp
705                 710                 715                 720
Lys Lys Glu Val Phe Arg Ser Leu Lys Pro Ala Gly Glu Val Asp Leu
                725                 730                 735
Thr Ala Leu Ala Lys Glu Leu Arg Ala Val Glu Asp Val Arg Pro Pro
            740                 745                 750
His Lys Val Thr Asp Tyr Ser Ser Ser Glu Glu Ser Gly Thr Thr
            755                 760                 765
Asp Glu Phe Glu Glu Pro Val His Gln Glu Gly Ala Asp Asp Ser Thr
            770                 775                 780
Ser Gly Pro Glu Asp Thr Arg Ala Ala Ser Pro Asn Leu Ser Asn Gly
785                 790                 795                 800
Glu Thr Glu Ser Val Lys Thr Met Ile Val His Asp Asp Val Glu Ser
                805                 810                 815
Glu Pro Ala Met Thr Pro Ser Lys Glu Gly Thr Leu Ile Val Arg Gln
            820                 825                 830
Thr Gln Ser Ala Ser Ser Thr Leu Gln Lys His Lys Ser Ser Ser Ser
            835                 840                 845
Phe Thr Pro Asp Phe Thr Asp Pro Arg Leu Leu Leu Gln Ile Ser Pro
            850                 855                 860
Ser Gly Thr Thr Val Thr Ser Val Val Gly Phe Ser Cys Asp Gly Leu
865                 870                 875                 880
Arg Pro Glu Ala Ile Arg Gln Asp Pro Thr Arg Lys Gly Ser Val Val
                885                 890                 895
Asn Val Asn Pro Thr Asn Thr Arg Pro Gln Ser Asp Thr Pro Glu Ile
                900                 905                 910
Arg Lys Tyr Lys Lys Arg Phe Asn Ser Glu Ile Leu Cys Ala Ala Leu
            915                 920                 925
Trp Gly Val Asn Leu Leu Val Gly Thr Glu Ser Gly Leu Met Leu Leu
            930                 935                 940
Asp Arg Ser Gly Gln Gly Lys Val Tyr Pro Leu Ile Ser Arg Arg Arg
945                 950                 955                 960
Phe Gln Gln Met Asp Val Leu Glu Gly Leu Asn Val Leu Val Thr Ile
                965                 970                 975
Ser Gly Lys Lys Asp Lys Leu Arg Val Tyr Tyr Leu Ser Trp Leu Arg
            980                 985                 990
Asn Arg Ile Leu His Asn Asp Pro  Glu Val Glu Lys Lys  Gln Gly Trp
            995                 1000                1005
Thr Thr  Val Gly Asp Leu Glu  Gly Cys Val His Tyr  Lys Val Val
            1010                1015                1020
Lys Tyr  Glu Arg Ile Lys Phe  Leu Val Ile Ala Leu  Lys Ser Ser
            1025                1030                1035
Val Glu  Val Tyr Ala Trp Ala  Pro Lys Pro Tyr His  Lys Phe Met
            1040                1045                1050
Ala Phe  Lys Ser Phe Gly Glu  Leu Leu His Lys Pro  Leu Leu Val
            1055                1060                1065
Asp Leu  Thr Val Glu Glu Gly  Gln Arg Leu Lys Val  Ile Tyr Gly
            1070                1075                1080
```

```
Ser Cys Ala Gly Phe His Ala Val Asp Val Asp Ser Gly Ser Val
    1085                1090                1095

Tyr Asp Ile Tyr Leu Pro Thr His Ile Gln Cys Ser Ile Lys Pro
    1100                1105                1110

His Ala Ile Tyr Ile Leu Pro Asn Thr Asp Gly Met Glu Leu Leu
    1115                1120                1125

Val Cys Tyr Glu Asp Glu Gly Val Tyr Val Asn Thr Tyr Gly Arg
    1130                1135                1140

Ile Thr Lys Asp Val Val Leu Gln Trp Gly Glu Met Pro Thr Ser
    1145                1150                1155

Val Ala Tyr Ile His Ser Asn Gln Thr Met Gly Trp Gly Glu Lys
    1160                1165                1170

Ala Ile Glu Ile Arg Ser Val Glu Thr Gly His Leu Asp Gly Val
    1175                1180                1185

Phe Met His Lys Arg Ala Gln Arg Leu Lys Phe Leu Cys Gly Arg
    1190                1195                1200

Asn Asp Lys Val Phe Phe Ser Ser Val Arg Ser Gly Gly Ser Ser
    1205                1210                1215

Gln Val Tyr Phe Met Thr Leu Gly Arg Thr Ser Leu Leu Ser Trp
    1220                1225                1230
```

<210> SEQ ID NO 36
<211> LENGTH: 6
<212> TYPE: PRT
<213> ORGANISM: Artificial sequence
<220> FEATURE:
<223> OTHER INFORMATION: synthetic

<400> SEQUENCE: 36

```
Pro Pro Leu Pro Thr Arg
1               5
```

GERMINAL CENTER KINASE CELL CYCLE PROTEINS

This application is a divisional of U.S. Ser. No. 09/425,324 filed Oct. 21, 1999.

FIELD OF THE INVENTION

The present invention is directed to compositions involved in cell cycle regulation and methods of use. More particularly, the present invention is directed to genes encoding proteins and proteins involved in cell cycle regulation. Methods of use include use in assays screening for modulators of the cell cycle and use as therapeutics.

BACKGROUND OF THE INVENTION

Cells cycle through various stages of growth, starting with the M phase, where mitosis and cytoplasmic division (cytokinesis) occurs. The M phase is followed by the G1 phase, in which the cells resume a high rate of biosynthesis and growth. The S phase begins with DNA synthesis, and ends when the DNA content of the nucleus has doubled. The cell then enters G2 phase, which ends when mitosis starts, signaled by the appearance of condensed chromosomes. Terminally differentiated cells are arrested in the G1 phase, and no longer undergo cell division.

The hallmark of a malignant cell is uncontrolled proliferation. This phenotype is acquired through the accumulation of gene mutations, the majority of which promote passage through the cell cycle. Cancer cells ignore growth regulatory signals and remain committed to cell division. Classic oncogenes, such as ras, lead to inappropriate transition from G1 to S phase of the cell cycle, mimicking proliferative extracellular signals. Cell cycle checkpoint controls ensure faithful replication and segregation of the genome. The loss of cell cycle checkpoint control results in genomic instability, greatly accelerating the accumulation of mutations which drive malignant transformation. Thus, modulating cell cycle checkpoint pathways and other such pathways with therapeutic agents could exploit the differences between normal and tumor cells, both improving the selectivity of radio- and chemotherapy, and leading to novel cancer treatments. As another example, it would be useful to control entry into apoptosis.

On the other hand, it is also sometimes desirable to enhance proliferation of cells in a controlled manner. For example, proliferation of cells is useful in wound healing and where growth of tissue is desirable. Thus, identifying modulators which promote, enhance or deter the inhibition of proliferation is desirable.

Proteins of general interest that have been reported on include kinases. The Ste20 family of kinases can be divided into two structurally distinct subfamilies. The first subfamily contains a C-terminal catalytic domain and an N-terminal binding site for the small G proteins Rac1 and Cdc42 (Herskowitz, Cell, 80:187–197 (1995)). The yeast serine/threonine kinase Ste20 and its mammalian homologue, p21 Activated Kinase 1 (PAK1), belong to this subfamily. Ste20 initiates a mitogen-activated protein kinase (MAPK) cascade that includes Ste11 (MAPKKK), Ste7 (MAPKK), FUS3/KSS1 (MAPK) in response to activation of the small G protein Cdc42, as well as signals from the hetero-trimeric G proteins coupled to pheromone receptors (Herskowitz, Cell, 80:187–197 (1995)). Similar to Ste20, PAK1 has been reported to be a Cdc42 and Rac1 effector molecule and specifically regulates the c-Jun N-terminal kinase (JNK) pathway, one of the mammalian MAPK pathways (Bagrodia, et. al., J. Biol. Chem., 270:27995–27998 (1995); Kyriakis, et al., J. Biol. Chem., 271:24313–24316 (1996)). The JNK pathway is activated by a variety of stress inducing agents, including osmotic and heat shock, UV irradiation, protein inhibitors and pro-inflammatory cytokines such as tumor necrosis factor (TNF) (Ip, et al., Curr. Opin. Cell Biol., 10:205–219 (1998)). JNKs are activated through threonine and tyrosine phosphorylation by MEK4 and MEK7 (MAPKK), which are in turn phosphorylated and activated by MAPKKKs including MEK kinase 1 (MEKK1), and mixed lineage kinases MLK2 and MLK3 (Ip, et al., Curr. Opin. Cell Biol., 10:205–219 (1998)). In addition to the activation of the JNK pathway, PAK1 has also been reported to be a regulator of the actin cytoskeleton (Sells, et al., Curr. Biol., 7:202–210 (1997)).

The second subgroup of Ste20 family of kinases is represented by the family of germinal center kinases (GCK) (Kyriakis, J. Biol. Chem., 274:5259–5262 (1999)). In contrast to Ste20 and PAK1, GCK family members have an N-terminal kinase domain and a C-terminal regulatory region. Many GCK family members, including GCK, germinal center kinase related protein (GCKR), meatopoietic protein kinase (HPK) 1, GCK-like kinase (GLK), HPK/GCK-like kinase (HGK) and NCK interacting kinase (NIK), have also been reported to activate the JNK pathway when overexpressed in 293 cells (Pombo, et al., Nature, 377:750–754 (1995); Shi, et al., J. Biol. Chem., 272:32102–32107 (1997); Kiefer, et al., EMBO J., 15:7013–7025 (1996); Diener, et al., Proc. Natl. Acad. Sci. USA, 94:9687–9692 (1997); Yao, et al., J. Biol. Chem., 274:2118–2125 (1999); Su, et al., EMBO J., 16:1279–1290 (1997)). Among those, GCK and GCKR have been implicated in mediating TNF-induced JNK activation through TNF receptor associated factor 2 (Traf2) (Pombo, et al., Nature, 377:750–754 (1995); Diener, et al., Proc. Natl. Acad. Sci. USA, 94:9687–9692 (1997); Yuasa, et al., J. Biol. Chem., 273:22681–22692 (1998)). NCK interacting kinase (NIK) interacts with the SH2-SH3 domain containing adapter protein NCK and has been proposed to link protein tyrosine kinase signals to JNK activation (Su, et al., EMBO J., 16:1279–1290 (1997)).

One study reports on a GCK family kinase from Dictyostelium that can phosphorylate Severin in vitro. (Eichinger, et al., J. Biol. Chem., 273:12952–12959 (1998)). Severin is an F-actin fragmenting and capping enzyme that regulates Dictyostelium motility. However, there has not been any studies indicating the involvement of mammalian GCKs in cytoskeleton regulation.

Despite the desirability of identifying cell cycle components and modulators, there is a deficit in the field of such compounds. Accordingly, it would be advantageous to provide compositions and methods useful in screening for modulators of the cell cycle. It would also be advantageous to provide novel compositions which are involved in the cell cycle.

SUMMARY OF THE INVENTION

The present invention provides cell cycle proteins and nucleic acids which encode such proteins. Also provided are methods for screening for a bioactive agent capable of modulating the cell cycle. The method comprises combining a cell cycle protein and a candidate bioactive agent and a cell or a population of cells, and determining the effect on the cell in the presence and absence of the candidate agent. Therapeutics for regulating or modulating the cell cycle are also provided.

In one aspect, a recombinant nucleic acid encoding a cell cycle protein of the present invention comprises a nucleic acid that hybridizes under high stringency conditions to a sequence complementary to that set forth in FIG. 21, 22, 23, 24, 25, 26, 27 or 28 (SEQ ID NOS:1–8). In a preferred embodiment, the cell cycle protein provided herein binds to Traf2 or Nck. Most preferably, the cell cycle protein binds to Traf2 and binds to Nck.

In one embodiment, a recombinant nucleic acid is provided which comprises a nucleic acid sequence as set forth in FIG. 21, 22, 23, 24, 25, 26, 27 or 28 (SEQ ID NOS:1–8). In another embodiment, a recombinant nucleic acid encoding a cell cycle protein is provided which comprises a nucleic acid sequence having at least 85% sequence identity to a sequence as set forth in FIG. 21, 22, 23, 24, 25, 26, 27 or 28. In a further embodiment, provided herein is a recombinant nucleic acid encoding an amino acid sequence as depicted in FIG. 1 for Tnik (SEQ ID NO:34), or FIG. 29, 30, 31, 32, 33, 34 or 35 (SEQ ID NOS:9–15).

In another aspect of the invention, expression vectors are provided. The expression vectors comprise one or more of the recombinant nucleic acids provided herein operably linked to regulatory sequences recognized by a host cell transformed with the nucleic acid. Further provided herein are host cells comprising the vectors and recombinant nucleic acids provided herein. Moreover, provided herein are processes for producing a cell cycle protein comprising culturing a host cell as described herein under conditions suitable for expression of the cell cycle protein. In one embodiment, the process includes recovering the cell cycle protein.

Also provided herein are recombinant cell cycle proteins encoded by the nucleic acids of the present invention. In one aspect, a recombinant polypeptide is provided herein which comprises an amino acid sequence having at least 80% sequence identity with a sequence as set forth in FIG. 21, 22, 23, 24, 25, 26, 27 or 28 (SEQ ID NOS:1–8). In one embodiment, a recombinant cell cycle protein is provided which comprises an amino acid sequence as set forth in FIG. 1 for Tnik (SEQ ID NO:34), or FIG. 29, 30, 31, 32, 33, 34 or 35 (SEQ ID NOS:9–15).

In another aspect, the present invention provides isolated polypeptides which specifically bind to a cell cycle protein as described herein. Examples of such isolated polypeptides include antibodies. Such an antibody can be a monoclonal antibody. In one embodiment, such an antibody reduces or eliminates the biological function of said cell cycle protein.

Further provided herein are methods for screening for a bioactive agent capable of binding to a cell cycle protein. In one embodiment the method comprises combining a cell cycle protein and a candidate bioactive agent, and determining the binding of said candidate bioactive agent to said cell cycle protein.

In another aspect, provided herein is a method for screening for a bioactive agent capable of interfering with the binding of a cell cycle protein and a Traf, preferably Traf2, or Nck protein. In one embodiment, such a method comprises combining a cell cycle protein, a candidate bioactive agent and a Traf or Nck protein, and determining the binding of the cell cycle protein and the Traf or Nck protein. If desired, the cell cycle protein and the Traf or Nck protein can be combined first.

Further provided herein are methods for screening for a bioactive agent capable of modulating the activity of cell cycle protein. In one embodiment the method comprises adding a candidate bioactive agent to a cell comprising a recombinant nucleic acid encoding a cell cycle protein, and determining the effect of the candidate bioactive agent on the cell. In a preferred embodiment, a library of candidate bioactive agents is added to a plurality of cells comprising a recombinant nucleic acid encoding a cell cycle protein.

Other aspects of the invention will become apparent to the skilled artisan by the following description of the invention.

BRIEF DESCRIPTION OF THE DRAWINGS

FIG. 1 shows a sequence alignment of Tnik (top sequence; SEQ ID NO:34) to NIK (bottom sequence; SEQ ID NO:35). Identical residues are shaded with black and homologous residues are shaded with gray and dotted below. The three alternatively spliced exons are marked by (−) above the Tnik sequence.

FIG. 2 shows a picture of a gel showing polymerase chain reaction (PCR) products of Tnik fragments from human spleen, heart and brain cDNAs. Oligos corresponding to nucleotides 1264–1281 and nucleotides 2427–2410 were used as primers.

FIG. 3 shows a diagram of NIK and Tnik spliced isoforms. The percent homology between Tnik and NIK in individual domains is indicated. The three alternatively spliced exons are hatched and the amino acid boundaries corresponding to the three exons are indicated.

FIG. 4 shows a picture of a gel with the results of an in vitro kinase assay of Tnik. Phoenix-A cells in 6-well plates were transiently transfected with 3 μg of HA-Tnik(VvT) (lanes 1 and 3) or HA-Tnik(KM) (lane 2 and 4). Expressed proteins were immunoprecipitated with an anti-HA antibody. Immune complexes were subjected to in vitro kinase assay (lanes 1, 2) or immunoblotting with an anti-HA antibody (lanes 3, 4).

FIGS. 5A and 5B shows a picture of the results of expression of Tnik message in human tissues. FIG. 5A: Human multi-tissue Northern blot (Clontech) was hybridized with a probe corresponding to nts 1264–2427 in the Tnik coding region. FIG. 5B: The same blot was stripped and re-blotted with an β-actin probe to control for the amount of mRNA on each lane.

FIG. 6 shows the interaction of Tnik with Traf2 by a gel showing co-immunoprecipitation of Tnik with endogenous Traf2. Phoenix-A cells in 100 mm dishes were transiently transfected with 10 μg of vector (lane 1) or HA-Tnik (lane 2). Top panel: Cell lysates were immunoprecipitated with an anti-HA mAb and blotted with an anti-Traf2 pAb. Middle and bottom panels: One tenth of cell lysates were blotted with an anti-HA mAb or an anti-Traf2 pAb to control for protein expression.

FIG. 7 shows a schematic diagram of Tnik mutants.

FIGS. 8A–8C show results which show the mapping of domains on Tnik that mediated its interaction with Traf2. FLAG-Traf2 was co-transfected into Phoenix-A cells with HA-Tnik mutants. Top panel: Cell lysates were immunoprecipitated with an anti-HA pAb and blotted with an anti-FLAG mAb. Middle and bottom panels: Cell lysates were immunoblotted with an anti-FLAG mAb or an anti-HA mAb.

FIG. 9 shows a schematic diagram of Traf2 mutants.

FIG. 10 shows the mapping of domains on Traf2 that mediated its interaction with Tnik. HA-Tnik was co-transfected into Phoenix-A cells with FLAG-Traf2 mutants and the cell lysates were analyzed as in FIG. 8.

FIG. 11 shows the results showing interaction of Tnik with NCK by co-immunoprecipitation of Tnik with endogenous NCK. Phoenix-A cells in 100 mm dishes were transiently transfected with 10 μg of vector (lane 1) or HA-Tnik (lane 2). Top panel: Cell lysates were immunoprecipitated with an anti-HA pAb and blotted with an anti-NCK mAb. Middle and bottom panels: One tenth of cell lysates were blotted with an anti-NCK mAb or an anti-HA mAb.

FIG. 12 shows the mapping of domains on Tnik that mediated its interaction with NCK. FLAG-NCK was co-transfected into Phoenix-A cells with HA-Tnik mutants. Top panel: Cell lysates were immunoprecipitated with an anti-HA pAb and blotted with an anti-FLAG mAb. Middle and bottom panels: Cell lysates were immunoblotted with an anti-FLAG mAb or an anti-HA mAb to control for protein expression.

FIG. 13 shows the results showing specific activation of the JNK pathway by Tnik by overexpression of Tnik activated JNK2. 1 μg of Myc-JNK2 was co-transfected into Phoenix-A cells in 6-well plates with 3 μg of vector (lanes 1–2), 1, 2 or 3 μg of Tnik plus 2, 1 or 0 μg of vector (lanes 3–5), or 1 μg of Traf2 plus 2 μg of vector (lane 6). Top panel: Myc-JNK2 was immunoprecipitated from cell lysates by an anti-Myc mAb and subjected to an in vitro kinase assay with GST-cJun as an exogenous substrate. In lane 2, 100 ng/ml of TNFα was added for 15 min before the cells were lysed. Bottom panel: One tenth of cell lysates were immunoblotted with an anti-Myc mAb to control for expression levels of Myc-JNK2.

FIG. 14 shows overexpression of Tnik did not activate extracellular signal regulated kinase (ERK) 1. 1 μg of Myc-ERK1 was co-transfected into Phoenix-A cells in 6-well plates with 3 μg of vector (lane 1), 1, 2 or 3 μg of Tnik plus 2, 1 or 0 μg of vector (lanes 2–4), or 0.05 μg of MEKK1 plus 2.95 μg of vector (lane 5). Top panel: Myc-ERK1 was immunoprecipitated from cell lysates by an anti-Myc mAb and subjected to an in vitro kinase assay with MBP as an exogenous substrate. Bottom panel: One tenth of the cell lysates were immunoblotted with an anti-Myc mAb to control for expression levels of Myc-ERK1.

FIG. 15 shows overexpression of Tnik did not activate p38. 1 μg of FLAG-p38 was co-transfected into Phoenix-A cells in 6-well plates with 3 μg of vector (lane 1), 1, 2 or 3 μg of Tnik plus 2, 1 or 0 μg of vector (lanes 2–4), or 0.05 μg of MEKK1 plus 2.95 μg of vector (lane 5). Top panel: FLAG-p38 was immunoprecipitated from cell lysates by an anti-FLAG mAb and subjected to an in vitro kinase assay with GST-ATF2 as an exogenous substrate. Bottom panel: One tenth of cell lysates were immunoblotted with an anti-FLAG mAb to control for expression levels of FLAG-p38.

FIG. 16 shows that the C-terminal GCKH (germinal center kinase homology region) domain of Tnik is both necessary and sufficient for JNK activation. 1 μg of Myc-JNK2 was co-transfected into Phoenix-A cells in 6-well plates with 3 μg of vector (lanes 1, 2), 3 μg of the indicated Tnik mutants (lanes 3–9) or 0.05 μg of MEKK1 plus 2.95 μg of vector (lane 10). In vitro kinase assay and immunoblotting were performed as described in A. These experiments were repeated at least three times.

FIG. 17 shows the results showing regulation of the cytoskeleton by Tnik. The results showing inhibition of cell spreading by Tnik. 0.4 μg of GFP was co-transfected into Phoenix-A cells with 3 μg of Vector, Tnik(WT), Tnik(KM), Tnik(N1), Tnik(C1) or JNK2. 24 hours after transfection, cells were examined under fluorescent microscope.

FIG. 18 shows the results showing Tnik overexpression did not induce apoptosis. 3 μg of Vector, Tnik(WT), Tnik (KM) or RIP was transfected into Phoenix-A cells for 24 hours. Transfected cells were stained with Hoechst 33258 and examined under fluorescent microscope.

FIG. 19 shows a picture of a gel showing Tnik overexpression induced redistribution of actin. Phoenix-A cells were transfected with 3 μg of vector, HA-Tnik(WT) or HA-Tnik(KM) and lysed with 1% Triton X-100 as described in EXPERIMENTAL PROCEDURES. Cell lysates (4×10⁴ cells) from either Triton X-100 soluble (lanes 1–3) or insoluble (lanes 4–6) fractions were resolved on SDS-PAGE and immunoblotted with an anti-β-actin mAb.

FIG. 20 shows a picture of a gel showing phosphorylation of Gelsolin by Tnik in vitro. Phoenix-A cells were transiently transfected with 3 μg of HA-Tnik(WT) (lane 1) or HA-Tnik(KM) (lane 2). Cell lysates were subjected to anti-HA immunoprecipitation and an in vitro kinase assay using Gelsolin (Sigma) as an exogenous substrate.

FIG. 21 shows the nucleic acid sequence of SEQ ID NO:1, encoding a cell cycle protein, Tnik, isoform 1.

FIG. 22 shows the nucleic acid sequence of SEQ ID NO:2, encoding a cell cycle protein, Tnik, isoform 2.

Figure 23A:
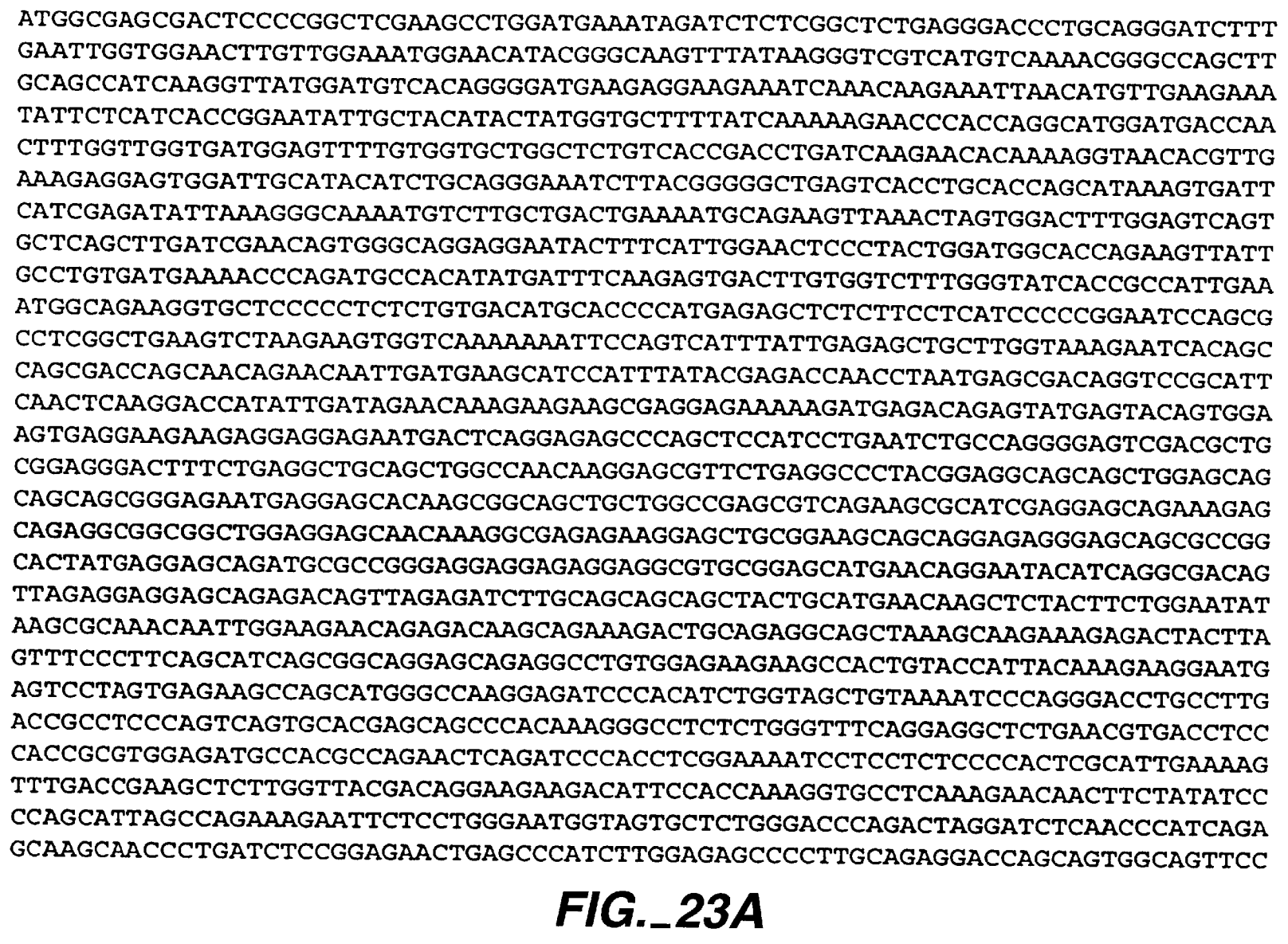

FIG. 23 shows the nucleic acid sequence of SEQ ID NO:3, encoding a cell cycle protein, Tnik, isoform 3.

FIG. 24 shows the nucleic acid sequence of SEQ ID NO:4, encoding a cell cycle protein, Tnik, isoform 4.

FIG. 25 shows the nucleic acid sequence of SEQ ID NO:5, encoding a cell cycle protein, Tnik, isoform 5.

FIG. 26 shows the nucleic acid sequence of SEQ ID NO:6, encoding a cell cycle protein, Tnik, isoform 6.

FIG. 27 shows the nucleic acid sequence of SEQ ID NO:7, encoding a cell cycle protein, Tnik, isoform 7.

FIG. 28 shows the nucleic acid sequence of SEQ ID NO:8, encoding a cell cycle protein, Tnik, isoform 8.

FIG. 29 shows the amino acid sequence of SEQ ID NO:9, of Tnik, isoform 2.

FIG. 30 shows the amino acid sequence of SEQ ID NO:10, of Tnik, isoform 3.

FIG. 31 shows the amino acid sequence of SEQ ID NO:11, of Tnik, isoform 4.

FIG. 32 shows the amino acid sequence of SEQ ID NO:12, of Tnik, isoform 5.

FIG. 33 shows the amino acid sequence of SEQ ID NO:13, of Tnik, isoform 6.

FIG. 34 shows the amino acid sequence of SEQ ID NO:14, of Tnik, isoform 7.

FIG. 35 shows the amino acid sequence of SEQ ID NO:15, of Tnik, isoform 8.

DETAILED DESCRIPTION OF THE INVENTION

The present invention provides cell cycle proteins and nucleic acids which encode such proteins. Also provided are methods for screening for a bioactive agent capable of modulating the cell cycle. The method comprises combining a cell cycle protein and a candidate bioactive agent and a cell or a population of cells, and determining the effect on the cell in the presence and absence of the candidate agent. Other screening assays including binding assays are also provided herein as described below. Therapeutics for regulating or modulating the cell cycle are also provided and described herein. Diagnostics, as further described below, are also provided herein.

A cell cycle protein of the present invention may be identified in several ways. "Protein" in this sense includes proteins, polypeptides, and peptides. The cell cycle proteins of the invention fall into two general classes: proteins that are completely novel, i.e. are not part of a public database as of the time of discovery, although they may have homology to either known proteins or peptides encoded by expressed sequence tags (ESTs). Alternatively, the cell cycle proteins are known proteins, but that were not known to be involved in the cell cycle; i.e. they are identified herein as having a novel biological function. Accordingly, a cell cycle protein may be initially identified by its association with a protein known to be involved in the cell cycle. Wherein the cell cycle proteins and nucleic acids are novel, compositions and methods of use are provided herein. In the case that the cell cycle proteins and nucleic acids were known but not known to be involved in cell cycle activity as described herein, methods of use, i.e. functional screens, are provided.

In one embodiment provided herein, a cell cycle protein as defined herein has one or more of the following characteristics: binding to Traf, preferably Traf2, binding to Nck; and cell cycle protein activity as described herein.

In one embodiment, the cell cycle protein is termed Tnik herein. One or more of the characteristics described below can apply to any of the cell cycle proteins provided herein, however, Tnik is used for illustrative purposes. Tnik is a member of the germinal center kinases. Preferably, Tnik binds to Traf or Nck. Preferably, the Traf protein is Traf2. In a preferred embodiment, Tnik binds to Traf and Nck.

Regarding Traf, regulation of CD40 signaling through multiple Traf binding sites and Traf hetero-oligomerization is described in, e.g., Pullen, et al., *Biochemistry*, 37(34):11836–45 (1998); Pullen, et al., *J Biol Chem.*, 274 (20):14246–54 (1999); Ishida, et al., *PNAS USA*, 93(18):9437–42 (1996); Kashiwada, et al., *J Exp Med*, 187(2):237–44(1998). Additionally, cell cycle and apoptosis-related proteins, kinases, and carcinomas are described in Muzio, et al., *J Dent Res.*, 78(7):1345–53 (1999); Jimenez, et al., *Nature*, 400(6739):81–8 3 (1999); and Hsieh, *Int J Oncol.*, 15(2):245–252 (1999). Moreover, Traf2 mediated activation of NF-kappa B by TNF receptor 2 and CD40 has been reported on. Rothe, et al., *Science*, 269(5229):1424–7 (1995). Regarding Traf2, also see, Takeuchi, et al., *JBC*, 271(33):19935–42 (1996) and Natoli, et al., *J Biol Chem*, 272(42):26079–82 (1997).

Regarding Nck, Nck has been reported on. For example, it has been reported that the adaptor protein Nck links receptor tyrosine kinases with the serine-threonine kinase Pak1. Nck is an adaptor protein composed of a single SH2 domain and three SH3 domains. Upon growth factor stimulation, Nck is recruited to receptor tyrosine kinases via its SH2 domain, probably initiating one or more signaling cascades. Galisteo, et al., *J Biol Chem.* 271(35):20997–1000 (1996). Also see, Chen, et al., *J Biol Chem.*, 273(39):25171–8 (1998) which reports on Nck family genes, chromosomal localization and expression.

As indicated below, Tnik shares homology with fragments of clone K1AA0551, GENBANK Accession number AB011123. Preferred embodiments of Tnik herein include the full length protein. In another preferred embodiment, Tnik comprises one or more cell cycle bioactivities as described below. In yet other embodiments wherein bioactivities are not required, Tnik excludes portions of the sequence which overlap with K1AA0551.

Thus, in some embodiments, the portions of homology with K1AA0551 may be excluded. For example, in Tnik Isoform number 1, the KIAA5501 fragment begins about with base pair number 1 at about position number 82 on Tnik and ends about with base pair number 4002 at about position number 4083 on Tnik. In Tnik isoform number 2, the KIAA5501 fragment begins about with base pair number 1338 at about position number 1332 on Tnik and ends about with base pair number 4002 at about position number 3996 on Tnik. In Tnik Isoform number 3, the KIAA5501 fragment begins about with base pair number 1691 at about position number 1607 on Tnik and ends about with base pair number 4002 at about position number 3918 on Tnik. In the Tnik isoform number 4, the KIAA5501 fragment begins about with base pair number 1 at about position number 82 on Tnik and ends about with base pair number 2301 at about position number 2382 on Tnik. In Tnik isoform number 5, the KIAA5501 fragment begins about with base pair number 1691 at about position number 1520 on Tnik and ends about with base pair number 4002 at about position number 3831 on Tnik. In Tnik isoform number 6, the KIAA5501 fragment begins about with base pair number 2326 at about position number 2296 on Tnik and ends about with base pair number 4002 at about position number 3972 on Tnik. In Tnik isoform number 7, the KIAA5501 fragment begins about with base pair number 2326 at about position number 2218 on Tnik and ends about with base pair number 4002 at about position number 3894 on Tnik. In Tnik isoform number 8, the KIAA5501 fragment begins about with base pair number 2326 at about position number 2131 on Tnik and ends about with base pair number 4002 at about position number 3807 on Tnik.

In a preferred embodiment, the cell cycle protein has a N-terminal kinase domain corresponding approximately to positions 1–305 of Tnik shown in the figures, an intermediate region, corresponding approximately to amino acid positions 306 through 1017 of Tnik as shown in the figures, and a C-terminal germinal center kinase homology region corresponding approximately to amino acids 1018 through 1360 of Tnik as shown in the figures. In one embodiment herein, the cell cycle protein consists essentially of one or more of the N-terminal kinase domain, intermediate region, and C-terminal germinal center kinase homology region.

In one embodiment, the cell cycle protein has one or more of the following characteristics: an intermediate region which shares greater than 40%, more preferably greater than 65%, more preferably, greater than 75%, more preferably greater than 85%, more preferably greater than 95% homology to the corresponding amino acids as shown in FIG. 1 (SEQ ID NOS:34–35) or encoded by any of the nucleic acids of FIGS. 21–28 (SEQ ID NOS:1–8); an N-terminal kinase domain of the cell cycle protein which shares greater than 90%, more preferably 95% homology to the corresponding amino acids as shown in FIG. 1 or encoded by any one of the nucleic acids of FIGS. 21–28; a C-terminal germinal center kinase homology region which has greater than 90%, more preferably 95% homology to the corresponding amino acids as shown in any one of FIGS. 1 and 29–35 (SEQ ID NOS:9–15). The embodiments provided herein explicitly include any combination of these characteristics. Moreover, the homology of the cell cycle protein may be greater in one region corresponding to one or more of the isoforms but not the other.

The homology to, for example, NIK can be found as described below. In one embodiment, homology is found using the following database and parameters homology. The method used to generate 90% and 40% homology is: Program: DNA Star Windows 32 version 3.18; Method: Jotun Hein; Multiple Alignment Parameters: Gap Penalty=11, Gap Length Penalty=3; Pairwise Alignment Parameters: K tuple=2.

In one embodiment, cell cycle nucleic acids or cell cycle proteins are initially identified by substantial nucleic acid and/or amino acid sequence identity or similarity to the sequence(s) provided herein. In a preferred embodiment, cell cycle nucleic acids or cell cycle proteins have sequence identity or similarity to the sequences provided herein as described below and one or more of the cell cycle protein bioactivities as further described below. Such sequence identity or similarity can be based upon the overall nucleic acid or amino acid sequence.

In a preferred embodiment, a protein is a "cell cycle protein" as defined herein if the overall sequence identity of the amino acid sequence of FIG. 1 for Tnik (SEQ ID NO:34), or FIG. 29, 30, 31, 32, 33, 34 or 35 (SEQ ID NOS:9–15) is preferably greater than about 75%, more preferably greater than about 80%, even more preferably greater than about 85% and most preferably greater than 90%. In some embodiments the sequence identity will be as high as about 93 to 95 or 98%.

In another preferred embodiment, a cell cycle protein has an overall sequence similarity with the amino acid sequence of FIG. 1 for Tnik (SEQ ID NO:34), or FIG. 29, 30, 31, 32, 33, 34 or 35 (SEQ ID NOS:9–15), of greater than about 80%, more preferably greater than about 85%, even more preferably greater than about 90% and most preferably greater than 93%. In some embodiments the sequence identity will be as high as about 95 to 98 or 99%.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith, et al., *Adv. Appl. Math.* 2:482 (1981), by the sequence identity alignment algorithm of Needleman, et al., *J. Mol. Biol.*, 48:443 (1970), by the search for similarity method of Pearson, et al., *PNAS USA,* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux, et al., *Nucl. Acid Res.,* 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng, et al., *J. Mol. Evol.,* 35:351–360 (1987); the method is similar to that described by Higgins, et al., *CABIOS,* 5:151–153 (1989). Useful PILEUP parameters including a default gap weight of 3.00, a default gap length weight of 0.10, and weighted end gaps.

Another example of a useful algorithm is the BLAST algorithm, described in Altschul, et al., *J. Mol. Biol,.* 215:403–410, (1990) and Karlin, et al., *PNAS USA,* 90:5873–5787 (1993). A particularly useful BlAST program is the WU-BLAST-2 program which was obtained from Altschul, et al., *Methods in Enzymology,* 266:460–480 (1996). WU-BLAST-2 uses several search parameters, most of which are set to the default values. The adjustable parameters are set with the following values: overlap span= 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul, et al., *Nucleic Acids Res.,* 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the cell cycle protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequences in the Figures, it is understood that in one embodiment, the percentage of sequence identity will be determined based on the number of identical amino acids in relation to the total number of amino acids. Thus, for example, sequence identity of sequences shorter than that shown in the Figure, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

Cell cycle proteins of the present invention may be shorter or longer than the amino acid sequence encoded by the nucleic acid shown in the Figure. Thus, in a preferred embodiment, included within the definition of cell cycle proteins are portions or fragments of the amino acid sequence encoded by the nucleic acid sequence provided herein. In one embodiment herein, fragments of cell cycle proteins are considered cell cycle proteins if a) they share at least one antigenic epitope; b) have at least the indicated sequence identity; c) and preferably have cell cycle biological activity as further defined herein. In some cases, where the sequence is used diagnostically, that is, when the presence or absence of cell cycle protein nucleic acid is determined, only the indicated sequence identity is required. The nucleic acids of the present invention may also be shorter or longer than the sequence in the Figure. The nucleic acid fragments include any portion of the nucleic acids provided herein which have a sequence not exactly previously identified; fragments having sequences with the indicated sequence identity to that portion not previously identified are provided in an embodiment herein.

In addition, as is more fully outlined below, cell cycle proteins can be made that are longer than those depicted in the Figure; for example, by the addition of epitope or purification tags, the addition of other fusion sequences, or the elucidation of additional coding and non-coding sequences. As described below, the fusion of a cell cycle peptide to a fluorescent peptide, such as Green Fluorescent Peptide (GFP), is particularly preferred.

Cell cycle proteins may also be identified as encoded by cell cycle nucleic acids which hybridize to the sequence depicted in the Figure, or the complement thereof, as outlined herein. Hybridization conditions are further described below.

In a preferred embodiment, when a cell cycle protein is to be used to generate antibodies, a cell cycle protein must share at least one epitope or determinant with the full length protein. By "epitope" or "determinant" herein is meant a portion of a protein which will generate and/or bind an antibody. Thus, in most instances, antibodies made to a smaller cell cycle protein will be able to bind to the full length protein. In a preferred embodiment, the epitope is unique; that is, antibodies generated to a unique epitope show little or no cross-reactivity. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies.

In a preferred embodiment, the antibodies to a cell cycle protein are capable of reducing or eliminating the biological function of the cell cycle proteins described herein, as is described below. That is, the addition of anti-cell cycle protein antibodies (either polyclonal or preferably monoclonal) to cell cycle proteins (or cells containing cell cycle proteins) may reduce or eliminate the cell cycle activity. Generally, at least a 25% decrease in activity is preferred, with at least about 50% being particularly preferred and about a 95–100% decrease being especially preferred.

The cell cycle antibodies of the invention specifically bind to cell cycle proteins. In a preferred embodiment, the antibodies specifically bind to cell cycle proteins. By "specifically bind" herein is meant that the antibodies bind to the protein with a binding constant in the range of at least $10^{-4}$–$10^{-6}$ M$^{-1}$, with a preferred range being $10^{-7}$–$10^{-9}$ M$^{-1}$. Antibodies are further described below.

In the case of the nucleic acid, the overall sequence identity of the nucleic acid sequence is commensurate with amino acid sequence identity but takes into account the degeneracy in the genetic code and codon bias of different organisms. Accordingly, the nucleic acid sequence identity may be either lower or higher than that of the protein sequence. Thus the sequence identity of the nucleic acid sequence as compared to the nucleic acid sequence of the Figure is preferably greater than 75%, more preferably greater than about 80%, particularly greater than about 85% and most preferably greater than 90%. In some embodiments the sequence identity will be as high as about 93 to 95 or 98%.

In a preferred embodiment, a cell cycle nucleic acid encodes a cell cycle protein. As will be appreciated by those in the art, due to the degeneracy of the genetic code, an extremely large number of nucleic acids may be made, all of which encode the cell cycle proteins of the present invention. Thus, having identified a particular amino acid sequence, those skilled in the art could make any number of different nucleic acids, by simply modifying the sequence of one or more codons in a way which does not change the amino acid sequence of the cell cycle protein.

In one embodiment, the nucleic acid is determined through hybridization studies. Thus, for example, nucleic acids which hybridize under high stringency to the nucleic acid sequence shown in the Figure, or its complement is considered a cell cycle nucleic acid. High stringency conditions are known in the art; see for example Maniatis, et al., *Molecular Cloning: A Laboratory Manual*, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

The cell cycle proteins and nucleic acids of the present invention are preferably recombinant. As used herein and further defined below, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. As will be appreciated by those in the art, the depiction of a single strand ("Watson") also defines the sequence of the other strand ("Crick"); thus the sequences depicted in the Figures also include the complement of the sequence. By the term "recombinant nucleic acid" herein is meant nucleic acid, originally formed in vitro, in general, by the manipulation of nucleic acid by endonucleases, in a form not normally found in nature. Thus an isolated cell cycle nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a cell cycle protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In one embodiment, the present invention provides cell cycle protein variants. These variants fall into one or more of three classes: substitutional, insertional or deletional variants. These variants ordinarily are prepared by site specific mutagenesis of nucleotides in the DNA encoding a cell cycle protein, using cassette or PCR mutagenesis or other techniques well known in the art, to produce DNA encoding the variant, and thereafter expressing the DNA in recombinant cell culture as outlined above. However, variant cell cycle protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the cell cycle protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed cell cycle variants screened for the optimal combination of desired activity. Techniques for making substitution mutations at predetermined sites in DNA having a known sequence are well known, for example, M13 primer mutagenesis and PCR mutagenesis. Screening of the mutants is done using assays of cell cycle protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the cell cycle protein are desired, substitutions are generally made in accordance with the following chart:

Chart I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the cell cycle proteins as needed. Alternatively, the variant may be designed such that the biological activity of the cell cycle protein is altered. For example, glycosylation sites may be altered or removed.

Covalent modifications of cell cycle polypeptides are included within the scope of this invention. One type of covalent modification includes reacting targeted amino acid residues of a cell cycle polypeptide with an organic derivatizing agent that is capable of reacting with selected side chains or the N-or C-terminal residues of a cell cycle polypeptide. Derivatization with bifunctional agents is useful, for instance, for crosslinking cell cycle to a water-insoluble support matrix or surface for use in the method for purifying anti-cell cycle antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azido-salicylic acid, homobifunctional imidoesters, including disuccinimidyl esters such as 3,3'-dithiobis-(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, *Proteins: Structure and Molecular Properties*, W. H. Freeman & Co., San Francisco, pp. 79–86 (1983)], acetylation of the N-terminal amine, and amidation of any C-terminal carboxyl group.

Another type of covalent modification of the cell cycle polypeptide included within the scope of this invention comprises altering the native glycosylation pattern of the polypeptide. "Altering the native glycosylation pattern" is intended for purposes herein to mean deleting one or more carbohydrate moieties found in native sequence cell cycle polypeptide, and/or adding one or more glycosylation sites that are not present in the native sequence cell cycle polypeptide.

Addition of glycosylation sites to cell cycle polypeptides may be accomplished by altering the amino acid sequence thereof. The alteration may be made, for example, by the addition of, or substitution by, one or more serine or threonine residues to the native sequence cell cycle polypeptide (for O-linked glycosylation sites). The cell cycle amino acid sequence may optionally be altered through changes at the DNA level, particularly by mutating the DNA encoding the cell cycle polypeptide at preselected bases such that codons are generated that will translate into the desired amino acids.

Another means of increasing the number of carbohydrate moieties on the cell cycle polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the cell cycle polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge, et al., *Anal. Biochem.*, 118:131 (1981). Enzymatic cleavage of carbohydrate moieties on polypeptides can be achieved by the use of a variety of endo-and exo-glycosidases as described by Thotakura, et al., *Meth. Enzymol.*, 138:350 (1987).

Another type of covalent modification of cell cycle comprises linking the cell cycle polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Cell cycle polypeptides of the present invention may also be modified in a way to form chimeric molecules comprising a cell cycle polypeptide fused to another, heterologous polypeptide or amino acid sequence. In one embodiment, such a chimeric molecule comprises a fusion of a cell cycle polypeptide with a tag polypeptide which provides an epitope to which an anti-tag antibody can selectively bind. The epitope tag is generally placed at the amino-or carboxyl-terminus of the cell cycle polypeptide. The presence of such epitope-tagged forms of a cell cycle polypeptide can be detected using an antibody against the tag polypeptide. Also, provision of the epitope tag enables the cell cycle polypeptide to be readily purified by affinity purification using an anti-tag antibody or another type of affinity matrix that binds to the epitope tag. In an alternative embodiment, the chimeric molecule may comprise a fusion of a cell cycle polypeptide with an immunoglobulin or a particular region of an immunoglobulin. For a bivalent form of the chimeric molecule, such a fusion could be to the Fc region of an IgG molecule as discussed further below.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field, et al., *Mol. Cell. Biol.*, 8:2159–2165 (1988)]; the c-myc tag and the 8F9, 3C7, 6E10, G4, B7 and 9E10 antibodies thereto [Evan, et al., *Molecular and Cellular Biology*, 5:3610–3616 (1985)]; and the Herpes Simplex virus glycoprotein D (gD) tag and its antibody [Paborsky, et al., *Protein Engineering*, 3(6):547–553 (1990)]. Other tag polypeptides include the Flag-peptide [Hopp, et al., *BioTechnology*, 6:1204–1210 (1988)]; the KT3 epitope peptide [Martin, et al., *Science*, 255:192–194 (1992)]; tubulin epitope peptide [Skinner, et al., *J. Biol. Chem.*, 266:15163–15166 (1991)]; and the T7 gene 10 protein peptide tag [Lutz-Freyermuth, et al., *Proc. Natl. Acad. Sci. USA*, 87:6393–6397 (1990)].

In an embodiment herein, cell cycle proteins of the cell cycle family and cell cycle proteins from other organisms are cloned and expressed as outlined below. Thus, probe or degenerate polymerase chain reaction (PCR) primer sequences may be used to find other related cell cycle proteins from humans or other organisms. As will be appreciated by those in the art, particularly useful probe and/or PCR primer sequences include the unique areas of the cell cycle nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art. It is therefore also understood that provided along with the sequences in the sequences listed herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant cell cycle nucleic acid can be further-used as a probe to identify and isolate other cell cycle nucleic acids. It can also be used as a "precursor" nucleic acid to make modified or variant cell cycle nucleic acids and proteins.

Using the nucleic acids of the present invention which encode a cell cycle protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the cell cycle protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the cell cycle protein; for example, transcriptional and translational regulatory nucleic acid sequences from Bacillus are preferably used to express the cell cycle protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

Cell cycle proteins of the present invention are produced by culturing a host cell transformed with an expression vector containing nucleic acid encoding a cell cycle protein, under the appropriate conditions to induce or cause expression of the cell cycle protein. The conditions appropriate for cell cycle protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis,* SF9 cells, C129 cells, 293 cells, Neurospora, BHK, CHO, COS, and HeLa cells, fibroblasts, Schwanoma cell lines, immortalized mammalian myeloid and lymphoid cell lines, tumor lines.

In a preferred embodiment, the cell cycle proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for cell cycle protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, cell cycle proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of cell cycle protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli,* the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the cell cycle protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, cell cycle proteins are produced in insect cells. Expression vectors for the transformation of insect cells, and in particular, baculovirus-based expression vectors, are well known in the art.

In a preferred embodiment, cell cycle protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The cell cycle protein may also be made as a fusion protein, using techniques well known in the art. Thus, for example, for the creation of monoclonal antibodies, if the desired epitope is small, the cell cycle protein may be fused to a carrier protein to form an immunogen. Alternatively, the cell cycle protein may be made as a fusion protein to increase expression, or for other reasons. For example, when the cell cycle protein is a cell cycle peptide, the nucleic acid encoding the peptide may be linked to other nucleic acid for expression purposes. Similarly, cell cycle proteins of the invention can be linked to protein labels, such as green fluorescent protein (GFP), red fluorescent protein (RFP), blue fluorescent protein (BFP), yellow fluorescent protein (YFP), etc.

In one embodiment, the cell cycle nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the cell cycle protein is purified or isolated after expression. Cell cycle proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the cell cycle protein may be purified using a standard anti-cell cycle antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the cell cycle protein. In some instances no purification will be necessary.

Once expressed and purified if necessary, the cell cycle proteins and nucleic acids are useful in a number of applications.

The nucleotide sequences (or their complement) encoding cell cycle proteins have various applications in the art of molecular biology, including uses as hybridization probes, in chromosome and gene mapping and in the generation of anti-sense RNA and DNA. Cell cycle protein nucleic acid will also be useful for the preparation of cell cycle proteins by the recombinant techniques described herein.

The full-length native sequence cell cycle protein gene, or portions thereof, may be used as hybridization probes for a cDNA library to isolate other genes (for instance, those encoding naturally-occurring variants of cell cycle protein or cell cycle protein from other species)-which have a desired sequence identity to the cell cycle protein coding sequence. Optionally, the length of the probes will be about 20 to about 50 bases. The hybridization probes may be derived from the nucleotide sequences herein or from genomic sequences including promoters, enhancer elements and introns of native sequences as provided herein. By way of example, a screening method will comprise isolating the coding region of the cell cycle protein gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the cell cycle protein gene of the present invention can be used to screen libraries of human cDNA, genomic DNA or mRNA to determine which members of such libraries the probe hybridizes.

Nucleotide sequences encoding a cell cycle protein can also be used to construct hybridization probes for mapping the gene which encodes that cell cycle protein and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Nucleic acids which encode cell cycle protein or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a cell cycle protein can be used to clone genomic DNA encoding a cell cycle protein in accordance with established techniques and the genomic sequences used to generate transgenic animals that contain cells which express the desired DNA. Methods for generating transgenic animals, particularly animals such as mice or rats, have become conventional in the art and are described, for example, in U.S. Pat. Nos. 4,736,866 and 4,870,009. Typically, particular cells would be targeted for the cell cycle protein transgene incorporation with tissue-specific enhancers. Transgenic animals that include a copy of a transgene encoding a cell cycle protein introduced into the germ line of the animal at an embryonic stage can be used to examine the effect of increased expression of the desired nucleic acid. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of the cell cycle protein can be used to construct a cell cycle protein "knock out" animal which has a defective or altered gene encoding a cell cycle protein as a result of homologous recombination between the endogenous gene encoding a cell cycle protein and altered genomic DNA encoding a cell cycle protein introduced into an embryonic cell of the animal. For example, cDNA encoding a cell cycle protein can be used to clone genomic DNA encoding a cell cycle protein in accordance with established techniques. A portion of the genomic DNA encoding a cell cycle protein can be deleted or replaced with another gene, such as a gene encoding a selectable marker which can be used to monitor integration. Typically, several kilobases of unaltered flanking DNA (both at the 5' and 3' ends) are included in the vector [see e.g., Thomas, et al., Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li, et al., Cell, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the cell cycle protein.

It is understood that the models described herein can be varied. For example, "knock-in" models can be formed, or the models can be cell-based rather than animal models.

Nucleic acid encoding the cell cycle polypeptides, antagonists or agonists may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik, et al., Proc. Natl. Acad. Sci. USA, 83:4143–4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau, et al., *Trends in Biotechnology,* 11:205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu, et al., *J. Biol. Chem.,* 262:4429–4432 (1987); and Wagner, et al., *Proc. Natl. Acad. Sci. USA,* 87:3410–3414 (1990). For review of gene marking and gene therapy protocols see Anderson, et al., *Science* 256:808–813 (1992).

In a preferred embodiment, the cell cycle proteins, nucleic acids, variants, modified proteins, cells and/or transgenics containing the said nucleic acids or proteins are used in screening assays. Identification of the cell cycle protein provided herein permits the design of drug screening assays for compounds that bind or interfere with the binding to the cell cycle protein and for compounds which modulate cell cycle activity.

The assays described herein preferably utilize the human cell cycle protein, although other mammalian proteins may also be used, including rodents (mice, rats, hamsters, guinea pigs, etc.), farm animals (cows, sheep, pigs, horses, etc.) and primates. These latter embodiments may be preferred in the development of animal models of human disease. In some embodiments, as outlined herein, variant or derivative cell cycle proteins may be used, including deletion cell cycle proteins as outlined above.

In a preferred embodiment, the methods comprise combining a cell cyle protein and a candidate bioactive agent, and determining the binding of the candidate agent to the cell cycle protein. In other embodiments, further discussed below, binding interference or bioactivity is determined.

The term "candidate bioactive agent" or "exogenous compound" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, i.e., at zero concentration or below the level of detection. In addition, positive controls, i.e. the use of agents known to alter cell cycling, may be used. For example, p21 is a molecule known to arrest cells in the G1 cell phase, by binding G1 cyclin-CDK complexes.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., *Tetrahedron*, 49(10):1925 (1993) and references therein; Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321 (1989)), O-methylphophoroamidite linkages (see Eckstein, Oligonucleotides and Analogues: A Practical Approach, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al., *Nature*, 380:207 (1996), all of which are incorporated by reference)). Other analog nucleic acids include those with positive backbones (Denpcy, et al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowski, et al., *Angew. Chem. Intl. Ed. English*, 30:423 (1991); Letsinger, et al., *J. Am. Chem. Soc.*, 110:4470 (1988); Letsinger, et al., *Nucleoside & Nucleotide*, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); *Tetrahedron Lett.*, 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., *Chem. Soc. Rev., pp.* 169–176 (1995)). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties, a wide variety of which are available in the literature.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, which provide the candidate bioactive agents in a conformationally restricted or stable form; b) targeting sequences, which allow the localization of the candidate bioactive agent into a subcellular or extracellular compartment; c) rescue sequences which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f) any combination of a), b), c), d), and e), as well as linker sequences as needed.

In one embodiment of the methods described herein, portions of cell cycle proteins are utilized; in a preferred embodiment, portions having cell cycle activity are used. Cell cycle activity is described further below and includes binding activity to Traf or Nck or cell cycle protein modulators as further described below. In addition, the assays described herein may utilize either isolated cell cycle proteins or cells comprising the cell cycle proteins.

Generally, in a preferred embodiment of the methods herein, for example for binding assays, the cell cycle protein or the candidate agent is non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. In some embodiments, Traf2 or Nck can be used. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used; examples of such are described below.

In a preferred embodiment, the cell cycle protein is bound to the support, and a candidate bioactive agent is added to the assay. Alternatively, the candidate agent is bound to the support and the cell cycle protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the cell cycle protein may be done in a number of ways. In a preferred embodiment, the candidate bioactive agent is labelled, and binding determined directly. For example, this may be done by attaching all or a portion of the cell cycle protein to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. cell cycle protein), such as an antibody, peptide, binding partner, ligand, etc. In a preferred embodiment, the competitor is Traf, preferably Traf2, or Nck. Under certain circumstances, there may be competitive binding as between the bioactive agent and the binding moiety, with the binding moiety displacing the bioactive agent. This assay can be used to determine candidate agents which interfere with binding between cell cycle proteins and Traf2 or Nck. "Interference of binding" as used herein means that native binding of the cell cycle protein differs in the presence of the candidate agent. The binding can be eliminated or can be with a reduced affinity. Therefore, in one embodiment, interference is caused by, for example, a conformation change, rather than direct competition for the native binding site.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the cell cycle protein and thus is capable of binding to, and potentially modulating, the activity of the cell cycle protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the cell cycle protein with a higher affinity. Thus, if the candidate bioactive agent is labeled, the presence of the label on the support, coupled with a lack of competitor binding, may indicate that the candidate agent is capable of binding to the cell cycle protein.

In a preferred embodiment, the methods comprise differential screening to identity bioactive agents that are capable of modulating the activity of the cell cycle proteins. Such assays can be done with the cell cycle protein or cells comprising said cell cycle protein. In one embodiment, the methods comprise combining an cell cycle protein and a competitor in a first sample. A second sample comprises a candidate bioactive agent, an cell cycle protein and a competitor. The binding of the competitor is determined for both samples, and a change, or difference in binding between the two samples indicates the presence of an agent capable of binding to the cell cycle protein and potentially modulating its activity. That is, if the binding of the competitor is different in the second sample relative to the first sample, the agent is capable of binding to the cell cycle protein.

Alternatively, a preferred embodiment utilizes differential screening to identify drug candidates that bind to the native cell cycle protein, but cannot bind to modified cell cycle proteins. The structure of the cell cycle protein may be modeled, and used in rational drug design to synthesize agents that interact with that site. Drug candidates that affect cell cycle bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of cell cycle may also be done. In a preferred embodiment, methods for screening for a bioactive agent capable of modulating the activity of cell cycle comprise the steps of adding a candidate bioactive agent to a sample of a cell cycle protein (or cells comprising a cell cycle protein) and determining an alteration in the biological activity of the cell cycle protein. "Modulating the activity of a cell cycle protein" includes an increase in activity, a decrease in activity, or a change in the type or kind of activity present. Thus, in this embodiment, the candidate agent should both bind to cell cycle (although this may not be necessary), and alter its biological or biochemical activity as defined herein. The methods include both in vitro screening methods, as are generally outlined above, and in vivo screening of cells for alterations in the presence, distribution, activity or amount of cell cycle protein.

Thus, in this embodiment, the methods comprise combining an cell cycle sample and a candidate bioactive agent, and evaluating the effect on the cell cycle. By "cell cycle activity" or "cell cycle protein activitiy" or grammatical equivalents herein is meant at least one of the cell cycle protein's biological activities, including, but not limited to, its ability to affect the cell cycle, bind to Traf2, bind to Nck, activate the JNK pathway, disrupt of F-actin upon overexpression, inhibit cell spreading upon overexpression, phosphorylate targets, phosphorylate Gelsolin, and regulate of the cytoskeleton. In some embodiments, fragments of the cell cycle protein are preferred, particularly fragments having one or more cell cycle protein activities.

In a preferred embodiment, the activity of the cell cycle protein is decreased; in another preferred embodiment, the activity of the cell cycle protein is increased. Thus, bioactive agents that are antagonists are preferred in some embodiments, and bioactive agents that are agonists may be preferred in other embodiments. As used herein, increased or overexpressed means an increase of at least 10%, more preferably 25–50%, more preferably 50%–75%, and more preferably at least a 100% to 500% increase over the native state. As used herein, decreased or underexpressed means a decrease of at least 10%, more preferably 25–50%, more preferably 50%–75%, and more preferably at least a 100% to 500% decrease over the native state, i.e., compared to without administeration of the cell cycle proteins, nucleic acids or candidate agents as described herein.

In a preferred embodiment, the invention provides methods for screening for bioactive agents capable of modulating the activity of an cell cycle protein. The methods comprise adding a candidate bioactive agent, as defined above, to a cell comprising cell cycle proteins. Preferred cell types include almost any cell. The cells contain a recombinant nucleic acid that encodes an cell cycle protein. In a preferred embodiment, a library of candidate agents are tested on a plurality of cells.

Detection of cell cycle regulation may be done as will be appreciated by those in the art. In one embodiment, indicators of the cell cycle are used. There are a number of parameters that may be evaluated or assayed to allow-the detection of alterations in cell cycle regulation, including, but not limited to, cell viability assays, assays to determine whether cells are arrested at a particular cell cycle stage ("cell proliferation assays"), and assays to determine at which cell stage the cells have arrested ("cell phase assays"). By assaying or measuring one or more of these parameters, it is possible to detect not only alterations in cell cycle regulation, but alterations of different steps of the cell cycle regulation pathway. This may be done to evaluate native cells, for example to quantify the aggressiveness of a tumor cell type, or to evaluate the effect of candidate drug agents that are being tested for their effect on cell cycle regulation. In this manner, rapid, accurate screening of candidate agents may be performed to identify agents that modulate cell cycle regulation.

Thus, the present compositions and methods are useful to elucidate bioactive agents that can cause a cell or a population of cells to either move out of one growth phase and into another, or arrest in a growth phase. In some embodiments, the cells are arrested in a particular growth phase, and it is desirable to either get them out of that phase or into a new phase. Alternatively, it may be desirable to force a cell to arrest in a phase, for example G1, rather than continue to move through the cell cycle. Similarly, it may be desirable in some circumstances to accelerate a non-arrested but slowly moving population of cells into either the next phase or just through the cell cycle, or to delay the onset of the next phase. For example, it may be possible to alter the activities of certain enzymes, for example kinases, phosphatases, proteases or ubiquitination enzymes, that contribute to initiating cell phase changes.

In a preferred embodiment, the methods outlined herein are done on cells that are not arrested in the G1 phase; that is, they are rapidly or uncontrollably growing and replicating, such as tumor cells. In this manner, candidate agents are evaluated to find agents that can alter the cell cycle regulation, i.e. cause the cells to arrest at cell cycle checkpoints, such as in G1 (although arresting in other phases such as S, G2 or M are also desirable). Alternatively, candidate agents are evaluated to find agents that can cause proliferation of a population of cells, i.e. that allow cells that are generally arrested in G1 to start proliferating again; for example, peripheral blood cells, terminally differentiated cells, stem cells in culture, etc.

Accordingly, the invention provides methods for screening for alterations in cell cycle regulation of a population of cells. By "alteration" or "modulation" (used herein interchangeably), is generally meant one of two things. In a preferred embodiment, the alteration results in a change in the cell cycle of a cell, i.e. a proliferating cell arrests in any one of the phases, or an arrested cell moves out of its arrested phase and starts the cell cycle, as compared to another cell or in the same cell under different conditions. Alternatively, the progress of a cell through any particular phase may be altered; that is, there may be an acceleration or delay in the length of time it takes for the cells to move thorough a particular growth phase. For example, the cell may be normally undergo a G1 phase of several hours; the addition of an agent may prolong the G1 phase.

The measurements can be determined wherein all of the conditions are the same for each measurement, or under various conditions, with or without bioactive agents, or at different stages of the cell cycle process. For example, a measurement of cell cycle regulation can be determined in a cell or cell population wherein a candidate bioactive agent is present and wherein the candidate bioactive agent is absent. In another example, the measurements of cell cycle regulation are determined wherein the condition or environment of the cell or populations of cells differ from one another. For example, the cells may be evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the measurements of cell cycle regulation are determined at different stages of the cell cycle process. In yet another example, the measurements of cell cycle regulation are taken wherein the conditions are the same, and the alterations are between one cell or cell population and another cell or cell population.

By a "population of cells" or "library of cells" herein is meant at least two cells, with at least about $10^3$ being preferred, at least about $10^6$ being particularly preferred, and at least about $10^8$ to $10^9$ being especially preferred. The population or sample can contain a mixture of different cell types from either primary or secondary cultures although samples containing only a single cell type are preferred, for example, the sample can be from a cell line, particularly tumor cell lines, as outlined below. The cells may be in any cell phase, either synchronously or not, including M, G1, S, and G2. In a preferred embodiment, cells that are replicating or proliferating are used; this may allow the use of retroviral vectors for the introduction of candidate bioactive agents. Alternatively, non-replicating cells may be used, and other vectors (such as adenovirus and lentivirus vectors) can be used. In addition, although not required, the cells are compatible with dyes and antibodies.

Preferred cell types for use in the invention include, but are not limited to, mammalian cells, including animal (rodents, including mice, rats, hamsters and gerbils), primates, and human cells, particularly including tumor cells of all types, including breast, skin, lung, cervix, colonrectal, leukemia, brain, etc.

In a preferred embodiment, the methods comprise assaying one or more of several different cell parameters, including, but not limited to, cell viability, cell proliferation, and cell phase. Other parameters which can be assayed, singuraly or jointly include Traf2 activity modulation, Nck activity modulation, JNK pathway activity, F-actin disruption, cell spreading, phosphorylation of Gelsolin, and cytoskeleton activity, particularly including mitosis and cytokinesis.

In a preferred embodiment, cell viability is assayed, to ensure that a lack of cellular change is due to experimental conditions (i.e. the introduction of a candidate bioactive agent) not cell death. There are a variety of suitable cell viability assays which can be used, including, but not limited to, light scattering, viability dye staining, and exclusion dye staining.

In a preferred embodiment, a light scattering assay is used as the viability assay, as is well known in the art. For example, when viewed in the FACS, cells have particular characteristics as measured by their forward and 90 degree (side) light scatter properties. These scatter properties represent the size, shape and granule content of the cells. These properties account for two parameters to be measured as a readout for the viability. Briefly, the DNA of dying or dead cells generally condenses, which alters the 90° scatter; similarly, membrane blebbing can alter the forward scatter. Alterations in the intensity of light scattering, or the cell-refractive index indicate alterations in viability.

Thus, in general, for light scattering assays, a live cell population of a particular cell type is evaluated to determine it's forward and side scattering properties. This sets a standard for scattering that can subsequently be used.

In a preferred embodiment, the viability assay utilizes a viability dye. There are a number of known viability dyes that stain dead or dying cells, but do not stain growing cells. For example, annexin V is a member of a protein family which displays specific binding to phospholipid (phosphotidylserine) in a divalent ion dependent manner. This protein has been widely used for the measurement of apoptosis (programmed cell death) as cell surface exposure of phosphatidylserine is a hallmark early signal of this process. Suitable viability dyes include, but are not limited to, annexin, ethidium homodimer-1, DEAD Red, propidium iodide, SYTOX Green, etc., and others known in the art; see the Molecular Probes Handbook of Fluorescent Probes and Research Chemicals, Haugland, Sixth Edition, hereby incorporated by reference; see Apoptosis Assay on page 285 in particular, and Chapter 16.

Protocols for viability dye staining for cell viability are known, see Molecular Probes catalog, supra. In this embodiment, the viability dye such as annexin is labeled, either directly or indirectly, and combined with a cell population. Annexin is commercially available, i.e., from PharMingen, San Diego, Calif., or Caltag Laboratories, Millbrae, Calif. Preferably, the viability dye is provided in a solution wherein the dye is in a concentration of about 100 ng/ml to about 500 ng/ml, more preferably, about 500 ng/ml to about 1 µg/ml, and most preferably, from about 1 µg/ml to about 5 µg/ml. In a preferred embodiment, the viability dye is directly labeled; for example, annexin may be labeled with a fluorochrome such as fluorecein isothiocyanate (FITC), Alexa dyes, TRITC, AMCA, APC, tri-color, Cy-5, and others known in the art or commercially available. In an alternate preferred embodiment, the viability dye is labeled with a first label, such as a hapten such as biotin, and a secondary fluorescent label is used, such as fluorescent streptavidin. Other first and second labeling pairs can be used as will be appreciated by those in the art.

Once added, the viability dye is allowed to incubate with the cells for a period of time, and washed, if necessary. The cells are then sorted as outlined below to remove the non-viable cells.

In a preferred embodiment, exclusion dye staining is used as the viability assay. Exclusion dyes are those which are excluded from living cells, i.e. they are not taken up passively (they do not permeate the cell membrane of a live cell). However, due to the permeability of dead or dying cells, they are taken up by dead cells. Generally, but not always, the exclusion dyes bind to DNA, for example via intercalation. Preferably, the exclusion dye does not fluoresce, or fluoresces poorly, in the absence of DNA; this eliminates the need for a wash step. Alternatively, exclusion dyes that require the use of a secondary label may also be used. Preferred exclusion dyes include, but are not limited to, ethidium bromide; ethidium homodimer-1; propidium iodine; SYTOX green nucleic acid stain; Calcein AM, BCECF AM; fluorescein diacetate; TOTO® and TO-PRO™ (from Molecular Probes; supra, see chapter 16) and others known in the art.

Protocols for exclusion dye staining for cell viability are known, see the Molecular Probes catalog, supra. In general, the exclusion dye is added to the cells at a concentration of from about 100 ng/ml to about 500 ng/ml, more preferably, about 500 ng/ml to about 1 $\mu$g/ml, and most preferably, from about 0.1 $\mu$g/ml to about 5 $\mu$g/ml, with about 0.5 $\mu$g/ml being particularly preferred. The cells and the exclusion dye are incubated for some period of time, washed, if necessary, and then the cells sorted as outlined below, to remove non-viable cells from the population.

In addition, there are other cell viability assays which may be run, including for example enzymatic assays, which can measure extracellular enzymatic activity of either live cells (i.e. secreted proteases, etc.), or dead cells (i.e. the presence of intracellular enzymes in the media; for example, intracellular proteases, mitochondrial enzymes, etc.). See the Molecular Probes Handbook of Fluorescent Probes and Research Chemicals, Haugland, Sixth Edition, hereby incorporated by reference; see chapter 16 in particular.

In a preferred embodiment, at least one cell viability assay is run, with at least two different cell viability assays being preferred, when the fluors are compatible. When only 1 viability assay is run, a preferred embodiment utilizes light scattering assays (both forward and side scattering). When two viability assays are run, preferred embodiments utilize light scattering and dye exclusion, with light scattering and viability dye staining also possible, and all three being done in some cases as well. Viability assays thus allow the separation of viable cells from non-viable or dying cells.

In addition to a cell viability assay, a preferred embodiment utilizes a cell proliferation assay. By "proliferation assay" herein is meant an assay that allows the determination that a cell population is either proliferating, i.e. replicating, or not replicating.

In a preferred embodiment, the proliferation assay is a dye inclusion assay. A dye inclusion assay relies on dilution effects to distinguish between cell phases. Briefly, a dye (generally a fluorescent dye as outlined below) is introduced to cells and taken up by the cells. Once taken up, the dye is trapped in the cell, and does not diffuse out. As the cell population divides, the dye is proportionally diluted. That is, after the introduction of the inclusion dye, the cells are allowed to incubate for some period of time; cells that lose fluorescence over time are dividing, and the cells that remain fluorescent are arrested in a non-growth phase.

Generally, the introduction of the inclusion dye may be done in one of two ways. Either the dye cannot passively enter the cells (e.g. it is charged), and the cells must be treated to take up the dye; for example through the use of a electric pulse. Alternatively, the dye can passively enter the cells, but once taken up, it is modified such that it cannot diffuse out of the cells. For example, enzymatic modification of the inclusion dye may render it charged, and thus unable to diffuse out of the cells. For example, the Molecular Probes CellTracker™ dyes are fluorescent chloromethyl derivatives that freely diffuse into cells, and then glutathione S-transferase-mediated reaction produces membrane impermeant dyes.

Suitable inclusion dyes include, but are not limited to, the Molecular Probes line of CellTracker™ dyes, including, but not limited to CellTracker™ Blue, CellTracker™ Yellow-Green, CellTracker™ Green, CellTracker™ Orange, PKH26 (Sigma), and others known in the art; see the Molecular Probes Handbook, supra; chapter 15 in particular.

In general, inclusion dyes are provided to the cells at a concentration ranging from about 100 ng/ml to about 5 $\mu$g/ml, with from about 500 ng/ml to about 1 $\mu$g/ml being preferred. A wash step may or may not be used. In a preferred embodiment, a candidate bioactive agent is combined with the cells as described herein. The cells and the inclusion dye are incubated for some period of time, to allow cell division and thus dye dilution. The length of time will depend on the cell cycle time for the particular cells; in general, at least about 2 cell divisions are preferred, with at least about 3 being particularly preferred and at least about 4 being especially preferred. The cells are then sorted as outlined below, to create populations of cells that are replicating and those that are not. As will be appreciated by those in the art, in some cases, for example when screening for anti-proliferation agents, the bright (i.e. fluorescent) cells are collected; in other embodiments, for example for screening for proliferation agents, the low fluorescence cells are collected. Alterations are determined by measuring the fluorescence at either different time points or in different cell populations, and comparing the determinations to one another or to standards.

In a preferred embodiment, the proliferation assay is an antimetabolite assay. In general, antimetabolite assays find the most use when agents that cause cellular arrest in G1 or G2 resting phase is desired. In an antimetabolite proliferation assay, the use of a toxic antimetabolite that will kill dividing cells will result in survival of only those cells that are not dividing. Suitable antimetabolites include, but are not limited to, standard chemotherapeutic agents such as methotrexate, cisplatin, taxol, hydroxyurea, nucleotide analogs such as AraC, etc. In addition, antimetabolite assays may include the use of genes that cause cell death upon expression.

The concentration at which the antimetabolite is added will depend on the toxicity of the particular antimetabolite, and will be determined as is known in the art. The antimetabolite is added and the cells are generally incubated for some period of time; again, the exact period of time will depend on the characteristics and identity of the antimetabolite as well as the cell cycle time of the particular cell population. Generally, a time sufficient for at least one cell division to occur.

In a preferred embodiment, at least one proliferation assay is run, with more than one being preferred. Thus, a proliferation assay results in a population of proliferating cells and a population of arrested cells. Moreover, other proliferation assays may be used, i.e., colorimetric assays known in the art.

In a preferred embodiment, either after or simultaneously with one or more of the proliferation assays outlined above, at least one cell phase assay is done. A "cell phase" assay determines at which cell phase the cells are arrested, M, G1, S, or G2.

In a preferred embodiment, the cell phase assay is a DNA binding dye assay. Briefly, a DNA binding dye is introduced to the cells, and taken up passively. Once inside the cell, the DNA binding dye binds to DNA, generally by intercalation, although in some cases, the dyes can be either major or minor groove binding compounds. The amount of dye is thus directly correlated to the amount of DNA in the cell, which varies by cell phase; G2 and M phase cells have twice the DNA content of G1 phase cells, and S phase cells have an intermediate amount, depending on at what point in S phase the cells are. Suitable DNA binding dyes are permeant, and include, but are not limited to, Hoechst 33342 and 33258, acridine orange, 7-AAD, LDS 751, DAPI, and SYTO 16, Molecular Probes Handbook, supra; chapters 8 and 16 in particular.

In general, the DNA binding dyes are added in concentrations ranging from about 1 μg/ml to about 5 μg/ml. The dyes are added to the cells and allowed to incubate for some period of time; the length of time will depend in part on the dye chosen. In one embodiment, measurements are taken immediately after addition of the dye. The cells are then sorted as outlined below, to create populations of cells that contain different amounts of dye, and thus different amounts of DNA; in this way, cells that are replicating are separated from those that are not. As will be appreciated by those in the art, in some cases, for example when screening for anti-proliferation agents, cells with the least fluorescence (and thus a single copy of the genome) can be separated from those that are replicating and thus contain more than a single genome of DNA. Alterations are determined by measuring the fluorescence at either different time points or in different cell populations, and comparing the determinations to one another or to standards.

In a preferred embodiment, the cell phase assay is a cyclin destruction assay. In this embodiment, prior to screening (and generally prior to the introduction of a candidate bioactive agent, as outlined below), a fusion nucleic acid is introduced to the cells. The fusion nucleic acid comprises nucleic acid encoding a cyclin destruction box and a nucleic acid encoding a detectable molecule. "Cyclin destruction boxes" are known in the art and are sequences that cause destruction via the ubiquitination pathway of proteins containing the boxes during particular cell phases. That is, for example, G1 cyclins may be stable during G1 phase but degraded during S phase due to the presence of a G1 cyclin destruction box. Thus, by linking a cyclin destruction box to a detectable molecule, for example green fluorescent protein, the presence or absence of the detectable molecule can serve to identify the cell phase of the cell population. In a preferred embodiment, multiple boxes are used, preferably each with a different fluor, such that detection of the cell phase can occur.

A number of cyclin destruction boxes are known in the art, for example, cyclin A has a destruction box comprising the sequence RTVLGVIGD (SEQ ID NO:16); the destruction box of cyclin B1 comprises the sequence RTALGDIGN (SEQ ID NO:17). See Glotzer, et al., Nature, 349:132–138 (1991). Other destruction boxes are known as well: YMTVSIIDRFMQDSCVPKKMLQLVGVT (rat cyclin B; SEQ ID NO:18); KFRLLQETMYMTVSIIDRFMQN-SCVPKK (mouse cyclin B; SEQ ID NO:19); RAILID-WLIQVQMKFRLLQETMYMTVS (mouse cyclin B1; SEQ ID NO:20); DRFLQAQLVCRKKLQVVGITALLLASK (mouse cyclin B2; SEQ ID NO:21); and MSVL-RGKLQLVGTAALL (mouse cyclin A2; SEQ ID NO:22).

The nucleic acid encoding the cyclin destruction box is operably linked to nucleic acid encoding a detectable molecule. The fusion proteins are constructed by methods known in the art. For example, the nucleic acids encoding the destruction box is ligated to a nucleic acid encoding a detectable molecule. By "detectable molecule" herein is meant a molecule that allows a cell or compound comprising the detectable molecule to be distinguished from one that does not contain it, i.e., an epitope, sometimes called an antigen TAG, a specific enzyme, or a fluorescent molecule. Preferred fluorescent molecules include but are not limited to green fluorescent protein (GFP), blue fluorescent protein (BFP), yellow fluorescent protein (YFP), red fluorescent protein (RFP), and enzymes including luciferase and β-galactosidase. When antigen TAGs are used, preferred embodiments utilize cell surface antigens. The epitope is preferably any detectable peptide which is not generally found on the cytoplasmic membrane, although in some instances, if the epitope is one normally found on the cells, increases may be detected, although this is generally not preferred. Similarly, enzymatic detectable molecules may also be used; for example, an enzyme that generates a novel or chromogenic product.

Accordingly, the results of sorting after cell phase assays generally result in at least two populations of cells that are in different cell phases.

The proteins and nucleic acids provided herein can also be used for screening purposes wherein the protein-protein interactions of the cell cycle proteins can be identified. Genetic systems have been described to detect protein-protein interactions. The first work was done in yeast systems, namely the "yeast two-hybrid" system. The basic system requires a protein-protein interaction in order to turn on transcription of a reporter gene. Subsequent work was done in mammalian cells. See Fields, et al., Nature, 340:245 (1989); Vasavada, et al., PNAS USA, 88:10686 (1991); Fearon, et al., PNAS USA, 89:7958 (1992); Dang, et al., Mol. Cell. Biol., 11:954 (1991); Chien, et al., PNAS USA, 88:9578 (1991); and U.S. Pat. Nos. 5,283,173, 5,667,973, 5,468,614, 5,525,490, and 5,637,463. a preferred system is described in Ser. No. 09/050,863, filed Mar. 30, 1998 and Ser. No. 09/359,081 filed Jul. 22, 1999, entitled "Mammalian Protein Interaction Cloning System". For use in conjunction with these systems, a particularly useful shuttle vector is described in Ser. No. 09/133,944, filed Aug. 14, 1998, entitled "Shuttle Vectors".

In general, two nucleic acids are transformed into a cell, where one is a "bait" such as the gene encoding a cell cycle protein or a portion thereof, and the other encodes a test candidate. Only if the two expression products bind to one another will an indicator, such as a fluorescent protein, be expressed. Expression of the indicator indicates when a test candidate binds to the cell cycle protein and can be identified as an cell cycle protein. Using the same system and the identified cell cycle proteins the reverse can be performed. Namely, the cell cycle proteins provided herein can be used to identify new baits, or agents which interact with cell cycle proteins. Additionally, the two-hybrid system can be used wherein a test candidate is added in addition to the bait and the cell cycle protein encoding nucleic acids to determine agents which interfere with the bait, such as Traf2 or Nck, and the cell cycle protein.

In one embodiment, a mammalian two-hybrid system is preferred. Mammalian systems provide post-translational modifications of proteins which may contribute significantly to their ability to interact. In addition, a mammalian two-hybrid system can be used in a wide variety of mammalian cell types to mimic the regulation, induction, processing, etc. of specific proteins within a particular cell type. For example, proteins involved in a disease state (i.e., cancer, apoptosis related disorders) could be tested in the relevant disease cells. Similarly, for testing of random proteins, assaying them under the relevant cellular conditions will give the highest positive results. Furthermore, the mammalian cells can be tested under a variety of experimental conditions that may affect intracellular protein-protein interactions, such as in the presence of hormones, drugs, growth factors and cytokines, radiation, chemotherapeutics, cellular and chemical stimuli, etc., that may contribute to conditions which can effect protein-protein interactions, particularly those involved in cancer.

Assays involving binding such as the two-hybrid system may take into account non-specific binding proteins (NSB).

Expression in various cell types, and assays for cell cycle activity are described above. The activity assays, such as having an effect on Traf2 or Nck binding, cytoskeleton regulation, phosphorylation activity, disruption of F-actin or JNK pathway activation, can be performed to confirm the activity of cell cycle proteins which have already been identified by their sequence identity/similarity or binding to Traf2 or Nck as well as to further confirm the activity of lead compounds identified as modulators of the cell cycle proteins provided herein such as Tnik.

The components provided herein for the assays provided herein may also be combined to form kits. The kits can be based on the use of the protein and/or the nucleic acid encoding the cell cycle proteins. In one embodiment, other components are provided in the kit. Such components include one or more of packaging, instructions, antibodies, and labels. Additional assays such as those used in diagnostics are further described below.

In this way, bioactive agents are identified. Compounds with pharmacological activity are able to enhance or interfere with the activity of the cell cycle protein. The compounds having the desired pharmacological activity may be administered in a physiologically acceptable carrier to a host, as further described below.

The present discovery relating to the role of cell cycle proteins in the cell cycle thus provides methods for inducing or preventing cell proliferation in cells. In a preferred embodiment, the cell cycle proteins, and particularly cell cycle protein fragments, are useful in the study or treatment of conditions which are mediated by the cell cycle proteins, i.e. to diagnose, treat or prevent cell cycle associated disorders. Thus, "cell cycle associated disorders" or "disease state" include conditions involving both insufficient or excessive cell proliferation, preferably, cancer.

Thus, in one embodiment, cell cycle regulation in cells or organisms are provided. In one embodiment, the methods comprise administering to a cell or individual in need thereof, a cell cycle protein in a therapeutic amount. Alternatively, an anti-cell cycle antibody that reduces or eliminates the biological activity of the endogenous cell cycle protein is administered. In another embodiment, a bioactive agent as identified by the methods provided herein is administered. Alternatively, the methods comprise administering to a cell or individual a recombinant nucleic acid encoding an cell cycle protein. As will be appreciated by those in the art, this may be accomplished in any number of ways. In a preferred embodiment, the activity of cell cycle is increased by increasing the amount of cell cycle in the cell, for example by overexpressing the endogenous cell cycle or by administering a gene encoding a cell cycle protein, using known gene-therapy techniques, for example. In a preferred embodiment, the gene therapy techniques include the incorporation of the exogenous gene using enhanced homologous recombination (EHR), for example as described in PCT/US93/03868, hereby incorporated by reference in its entirety.

Without being bound by theory, it appears that cell cycle protein is an important protein in the cell cycle. Accordingly, disorders based on mutant or variant cell cycle genes may be determined. In one embodiment, the invention provides methods for identifying cells containing variant cell cycle genes comprising determining all or part of the sequence of at least one endogeneous cell cycle genes in a cell. As will be appreciated by those in the art, this may be done using any number of sequencing techniques. In a preferred embodiment, the invention provides methods of identifying the cell cycle genotype of an individual comprising determining all or part of the sequence of at least one cell cycle gene of the individual. This is generally done in at least one tissue of the individual, and may include the evaluation of a number of tissues or different samples of the same tissue. The method may include comparing the sequence of the sequenced cell cycle gene to a known cell cycle gene, i.e. a wild-type gene.

The sequence of all or part of the cell cycle gene can then be compared to the sequence of a known cell cycle gene to determine if any differences exist. This can be done using any number of known sequence identity programs, such as Bestfit, etc. In a preferred embodiment, the presence of a difference in the sequence between the cell cycle gene of the patient and the known cell cycle gene is indicative of a disease state or a propensity for a disease state.

In one embodiment, the invention provides methods for diagnosing a cell cycle related condition in an individual. The methods comprise measuring the activity of cell cycle in a tissue from the individual or patient, which may include a measurement of the amount or specific activity of a cell cycle protein. This activity is compared to the activity of cell cycle from either a unaffected second individual or from an unaffected tissue from the first individual. When these activities are different, the first individual may be at risk for a cell cycle associated disorder. In this way, for example, monitoring of various disease conditions may be done, by monitoring the levels of the protein or the expression of mRNA therefor. Similarly, expression levels may correlate to the prognosis.

In one aspect, the expression levels of cell cycle protein genes are determined in different patient samples or cells for which either diagnosis or prognosis information is desired. Gene expression monitoring is done on genes encoding cell cycle proteins. In one aspect, the expression levels of cell cycle protein genes are determined for different cellular states, such as normal cells and cells undergoing apoptosis or transformation. By comparing cell cycle protein gene expression levels in cells in different states, information including both up- and down-regulation of cell cycle protein genes is obtained, which can be used in a number of ways. For example, the evaluation of a particular treatment regime may be evaluated: does a chemotherapeutic drug act to improve the long-term prognosis in a particular patient. Similarly, diagnosis may be done or confirmed by comparing patient samples. Furthermore, these gene expression levels allow screening of drug candidates with an eye to mimicking or altering a particular expression level. This may be done by making biochips comprising sets of important cell cycle protein genes, such as those of the present invention, which can then be used in these screens. These methods can also be done on the protein basis; that is, protein expression levels of the cell cycle proteins can be evaluated for diagnostic purposes or to screen candidate agents. In addition, the cell cycle protein nucleic acid sequences can be administered for gene therapy purposes, including the administration of antisense nucleic acids, or the cell cycle proteins administered as therapeutic drugs.

Cell cycle protein sequences bound to biochips include both nucleic acid and amino acid sequences as defined above. In a preferred embodiment, nucleic acid probes to cell cycle protein nucleic acids (both the nucleic acid sequences having the sequences outlined in the Figures and/or the complements thereof are made. The nucleic acid probes attached to the biochip are designed to be substantially complementary to the cell cycle protein nucleic acids, i.e. the target sequence (either the target sequence of the sample or to other probe sequences, for example in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A "nucleic acid probe" is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. In some embodiments, much longer nucleic acids can be used, up to hundreds of bases (e.g., whole genes).

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably show fluorescence.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo-or hetero-bifunctional linkers as are well known (see 1994 Pierce Chemical Company catalog, technical section on cross-linkers, pages 155–200, incorporated herein by reference). In addition, in some cases, additional linkers, such as alkyl groups (including substituted and heteroalkyl groups) may be used.

In this embodiment, oligonucleotides, corresponding to the nucleic acid probe, are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affimetrix Gene-Chip™ technology.

"Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, normal versus apoptotic cell. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, *Nature Biotechnology,* 14:1675–1680 (1996), hereby expressly incorporated by reference. Other techniques include, but are not limited to, quantitative reverse transcriptase PCR, Northern analysis and RNase protection.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the cell cycle protein and standard immunoassays (ELISAs, etc.) or other techniques, including mass spectroscopy assays, 2D gel electrophoresis assays, etc.

In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding an cell cycle protein is detected by binding the digoxygenin with an anti-digoxygenin secondary antibody and developed with nitro blue tetrazolium and 5-bromo-4-chloro-3-indoyl phosphate.

In another preferred method, expression of cell cycle protein is performed using in situ imaging techniques employing antibodies to cell cycle proteins. In this method cells are contacted with from one to many antibodies to the cell cycle protein(s). Following washing to remove non-specific antibody binding, the presence of the antibody or antibodies is detected. In one embodiment the antibody is detected by incubating with a secondary antibody that contains a detectable label. In another method the primary antibody to the cell cycle protein(s) contains a detectable label. In another preferred embodiment each one of multiple primary antibodies contains a distinct and detectable label. This method finds particular use in simultaneous screening for a plurality of cell cycle proteins. The label may be detected in a fluorometer which has the ability to detect and distinguish emissions of different wavelengths. In addition, a fluorescence activated cell sorter (FACS) can be used in this method. As will be appreciated by one of ordinary skill in the art, numerous other histological imaging techniques are useful in the invention and the antibodies can be used in ELISA, immunoblotting (Western blotting), immunoprecipitation, BIACORE technology, and the like.

In one embodiment, the cell cycle proteins of the present invention may be used to generate polyclonal and monoclonal antibodies to cell cycle proteins, which are useful as described herein. Similarly, the cell cycle proteins can be coupled, using standard technology, to affinity chromatography columns. These columns may then be used to purify cell cycle antibodies. In a preferred embodiment, the antibodies are generated to epitopes unique to the cell cycle protein; that is, the antibodies show little or no cross-reactivity to other proteins. These antibodies find use in a number of applications. For example, the cell cycle antibodies may be coupled to standard affinity chromatography columns and used to purify cell cycle proteins as further described below. The antibodies may also be used as blocking polypeptides, as outlined above, since they will specifically bind to the cell cycle protein.

The anti-cell cycle protein antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the cell cycle protein or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid a, synthetic trehalose dicorynomycolate). The immunization protocol may be selected by one skilled in the art without undue experimentation.

The anti-cell cycle protein antibodies may, alternatively, be monoclonal antibodies. Monoclonal antibodies may be prepared using hybridoma methods, such as those described by Kohler, et al., *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the cell cycle protein or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.,* 133:3001 (1984); Brodeur, et al., *Monoclonal Antibody Production Techniques and Applications,* Marcel Dekker, Inc., New York, pp. 51–63 (1987)].

The culture medium in which the hybridoma cells are cultured can then be assayed for the presence of monoclonal antibodies directed against cell cycle protein. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson, et al., *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein a-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison, et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The anti-cell cycle protein antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones, et al., *Nature,* 321:522–525 (1986); Riechmann, et al., *Nature,* 332:323–329 (1988); and Presta, *Curr. Op. Struct. Biol.,* 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones, et al., *Nature,* 321:522–525 (1986); Riechmann, et al., *Nature,* 332:323–327 (1988); Verhoeyen, et al., *Science,* 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom,, et al, *J. Mol. Biol.,* 227:381 (1991); Marks, et al., *J. Mol. Biol.,* 222:581 (1991)]. The techniques of Cole, et al. and Boerner, et al. are also available for the preparation of human monoclonal antibodies (Cole, et al., *Monoclonal Antibodies and Cancer Therapy,* Alan R. Liss, p. 77 (1985); Boerner, et al., *J. Immunol.,* 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications:

Marks, et al., *Bio/Technology*, 10:779–783 (1992); Lonberg, et al., *Nature*, 368:856–859 (1994); Morrison, *Nature*, 368:812–13 (1994); Fishwild, et al., *Nature Biotechnoloay*, 14:845–51 (1996); Neuberger, *Nature Biotechnology*, 14:826 (1996); Lonberg, et al., *Intern. Rev. Immunol.*, 13:65–93 (1995).

Bispecific antibodies are monoclonal, preferably human or humanized, antibodies that have binding specificities for at least two different antigens. In the present case, one of the binding specificities is for the cell cycle protein, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein, et al., *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker, et al., *EMBO J.*, 10:3655–3659(1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh, et al., *Methods in Enzymology*, 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The anti-cell cycle protein antibodies of the invention have various utilities. For example, anti-cell cycle protein antibodies may be used in diagnostic assays for an cell cycle protein, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: a Manual of Techniques*, CRC Press, Inc. pp. 147–158 (1987)]. The antibodies used in the diagnostic assays can be labeled with a detectable moiety. The detectable moiety should be capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter, et al., *Nature*, 144:945 (1962); David, et al., *Biochemistry*, 13:1014 (1974); Pain, et al., *J. Immunol. Meth.*, 40:219 (1981); and Nygren, *J. Histochem. and Cytochem.*, 30:407 (1982).

Anti-Cell cycle protein antibodies also are useful for the affinity purification of cell cycle protein from recombinant cell culture or natural sources. In this process, the antibodies against cell cycle protein are immobilized on a suitable support, such a Sephadex resin or filter paper, using methods well known in the art. The immobilized antibody then is contacted with a sample containing the cell cycle protein to be purified, and thereafter the support is washed with a suitable solvent that will remove substantially all the material in the sample except the cell cycle protein, which is bound to the immobilized antibody. Finally, the support is washed with another suitable solvent that will release the cell cycle protein from the antibody.

The anti-cell cycle protein antibodies may also be used in treatment. In one embodiment, the genes encoding the antibodies are provided, such that the antibodies bind to and modulate the cell cycle protein within the cell.

In one embodiment, a therapeutically effective dose of an cell cycle protein, agonist or antagonist is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for cell cycle protein degradation, systemic versus localized delivery, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the cell cycle protein, agonist or antagonist of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the composition may be directly applied as a solution or spray. Depending upon the manner of introduction, the compounds may be formulated in a variety of ways. The concentration of therapeutically active compound in the formulation may vary from about 0.1–100 wt. %.

The pharmaceutical compositions of the present invention comprise an cell cycle protein, agonist or antagonist (including antibodies and bioactive agents as described herein) in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

Combinations of the compositions may be administered. Moreover, the compositions may be administered in combination with other therapeutics, including growth factors or chemotherapeutics and/or radiation. Targeting agents (i.e. ligands for receptors on cancer cells) may also be combined with the compositions provided herein.

In one embodiment provided herein, the antibodies are used for immunotherapy, thus, methods of immunotherapy are provided. By "immunotherapy" is meant treatment of cell cycle protein related disorders with an antibody raised against a cell cycle protein. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with an cell cycle protein antigen to which antibodies are raised. As appreciated by one of ordinary skill in the art, the cell cycle protein antigen may be provided by injecting an cell cycle protein against which antibodies are desired to be raised into a recipient, or contacting the recipient with an cell cycle protein nucleic acid, capable of expressing the cell cycle protein antigen, under conditions for expression of the cell cycle protein antigen.

In a preferred embodiment, a therapeutic compound is conjugated to an antibody, preferably an cell cycle protein antibody. The therapeutic compound may be a cytotoxic agent. In this method, targeting the cytotoxic agent to apoptotic cells or tumor tissue or cells, results in a reduction in the number of afflicted cells, thereby reducing symptoms associated with apoptosis, cancer cell cycle protein related disorders. Cytotoxic agents are numerous and varied and include, but are not limited to, cytotoxic drugs or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies raised against cell cycle proteins, or binding of a radionuclide to a chelating agent that has been covalently attached to the antibody.

In a preferred embodiment, cell cycle protein genes are administered as DNA vaccines, either single nucleic acids or combinations of cell cycle protein genes. Naked DNA vaccines are generally known in the art; see Brower, *Nature Biotechnology*, 16:1304–1305 (1998). Methods for the use of nucleic acids as DNA vaccines are well known to one of ordinary skill in the art, and include placing an cell cycle protein gene or portion of an cell cycle protein nucleic acid under the control of a promoter for expression in a patient. The cell cycle protein gene used for DNA vaccines can encode full-length cell cycle proteins, but more preferably encodes portions of the cell cycle proteins including peptides derived from the cell cycle protein. In a preferred embodiment a patient is immunized with a DNA vaccine comprising a plurality of nucleotide sequences derived from a cell cycle protein gene. Similarly, it is possible to immunize a patient with a plurality of cell cycle protein genes or portions thereof, as defined herein. Without being bound by theory, following expression of the polypeptide encoded by the DNA vaccine, cytotoxic T-cells, helper T-cells and antibodies are induced which recognize and destroy or eliminate cells expressing cell cycle proteins.

In a preferred embodiment, the DNA vaccines include a gene encoding an adjuvant molecule with the DNA vaccine. Such adjuvant molecules include cytokines that increase the immunogenic response to the cell cycle protein encoded by the DNA vaccine. Additional or alternative adjuvants are known to those of ordinary skill in the art and find use in the invention.

The following example serves to more fully describe the manner of using the above-described invention, as well as to set forth the best modes contemplated for carrying out various aspects of the invention. It is understood that this example in no way serve to limit the true scope of this invention, but rather are presented for illustrative purposes. All references cited herein are expressly incorporated by reference in their entirety. Moreover, all sequences displayed, cited by reference or accession number in the references are incorporated by reference herein.

EXAMPLE 1

Cloning, Tissue Distribution, Binding, Activation and Regulation Functions of Tnik Antibodies and cytokines—Antibodies used in this report include: anti-HA mAb (Babco) and pAb (Santa Cruz Biotechnology); anti-FLAG mAb (Sigma) and pAb (Santa Cruz); anti-Myc mAb (Babco); anti-Traf2 pAb (Santa Cruz); anti-NCK mAb (Transduction Labs); anti-β-actin mAb (Sigma). TNFα was purchased from Calbiochem.

Cloning of full length Tnik and Northern blotting—Using yeast two-hybrid screening, overlapping cDNA fragments were identified that interacted with Traf2 and NCK. The sequences of the fragments were contained in a partial cDNA clone, KIAA0551 (Accession number AB011123), at GenBank. Antisense oligos TGCGCTTATATTCCAGAAG-TAGAGCT (SEQ ID NO:23) and CTGTCTCTGCTCCTC-CTCTA (SEQ ID NO:24) were designed according to the 5' end sequence of KIAA0551 and the full length Tnik cDNA was cloned from reverse transcribed human brain mRNA by RACE-PCR. Northern blotting was performed on human multi-tissue Northern blot according to the manufacturer's recommendations (Clontech). A PCR product amplified from nucleotide 1264 to nucleotide 2427 of Tnik coding region was used as a probe.

Plasmid construction—Full length human Tnik was cloned into pCI (Promega) derived expression vector pYCI under the control of the CMV promoter with an HA epitope tag (AYPYDVPDYA; SEQ ID NO:25) inserted on the N-terminus by PCR. A kinase mutant form of Tnik was constructed using the QuikChange mutagenesis kit (Stratagene) with Oligos AGCTTGCAGCCATCAGGGT-TATGGATGTCAC (SEQ ID NO:26) and GTGACATC-CATAACCTTGATGGCTGCAAGCT (SEQ ID NO:27) to change the highly conserved lysine 54 in the kinase domain to arginine. Full length human Traf2 was cloned into pYCI with a FLAG epitope tag (DYKDDDDKG; SEQ ID NO:28) inserted on the N-terminus by PCR. Full length human NCK was similarly cloned into pYCI with a FLAG epitope tag at the N-terminus. Myc-JNK2 and Myc-ERK1 were constructed in the pCR3.1 vector with a Myc epitope tag (ASMEQKLISEEDLN; SEQ ID NO:29) inserted on the N-terminus of JNK2 and ERK1, respectively. All the truncation mutants were constructed by PCR. For construction of the GFP-Tnik fusion protein, full length Tnik was PCR amplified from pYCI-Tnik and inserted in frame onto the 3'end of GFP. All constructs were verified by DNA sequencing.

Cell culture, transfection of Phoenix-A cells and immunoprecipitation—Phoenix-A cells (derivatives of 293 cells) (Coligan, et al., *Current Protocols in Immunology* [supplement], 31:10.28.1–10.28.17 (1999)) were grown in Dulbecco's modified Eagle's medium supplemented with 10% fetal bovine serum. Transfection of Phoenix-A cells was performed using the standard calcium phosphate method (Coligan, et al., *Current Protocols in Immunology* [supplement], 31:10.28.1–10.28.17 (1999)). Either $4 \times 10^5$ cells in a 6-well plate or $3 \times 10^6$ cells in a 100 mm tissue culture dish were seeded 16 hours before transfection. 3 μg of DNA was used in the transfection for each well of a 6-well plate, and 10 μg DNA was used for each 100 mm dish. Media was changed 8 hours after transfection. Cells were lysed in lysis buffer (1% NP-40, 20 mM Tris-HCl, pH 8.0, 150 mM NaCL) with protease inhibitors (Boehringer Mannheim) and analyzed 24 hours after transfection. Cell lysates were cleared by centrifugation (14,000 RPM×10 min). For immunoprecipitation studies, cell lysates ($2 \times 10^6$ cells /lane) were rotated with 2–3 μg of desired antibodies and 20 μl 50% slurry of protein A Sepharose (Pharmacia) for 1.5 hrs. Immune complexes were precipitated and the pellets washed three times with lysis buffer. Washed precipitates were subjected to SDS-PAGE analysis and Western blotting. Supersignal and Supersignal West Duro substrates (Piers) were used as detection systems for the Western blotting.

In vitro kinase assays—For the JNK in vitro kinase assay, Myc-JNK2 was co-transfected into Phoenix-A cells with Tnik mutants, Traf2 or MEKK as described above. 24 hours after transfection, cells were lysed with lysis buffer supplemented with 20 mM β-glycerophospate, 1 mM NaF, 1 mM Na₃VO₄ and protease inhibitors. Myc-JNK2 was precipitated from clarified cell lysates with an anti-Myc mAb and the pellets were washed three times with lysis buffer and two times with kinase buffer (20 mM HEPES, pH 7.4, 10 mM MnCl₂, 10 mM MgCl₂, 20 mM β-glycerophosphate, 1 mM NaF, 1 mM Na₃VO₄, 0.5 mM DTT). For the kinase reactions, immunoprecipitates were incubated with 1 μg glutathion S-transferase (GST) c-Jun (1–79) (Santa Cruz Biotechnology) in 20 μl kinase buffer supplemented with 1 μM PKI peptide (Sigma), 10 μM ATP, 5 μCi γ-P³² ATP for 20 minutes at 30° C. Kinase reactions were stopped by addition of 20 μl 2×SDS sample buffer (Norvex), heated at 95° C. for 5 minutes and then loaded onto SDS-PAGE. ERK and p38 in vitro kinase assays were conducted in a similar fashion. For ERK kinase assays, an anti-Myc mAb was used to immunoprecipitate Myc-ERK1 and Myelin Basic Protein (MBP, Sigma) was used as an exogenous substrate. For p38 kinase assays, an anti-FLAG mAb was used to immunoprecipitate FLAG-p38 and GST-ATF2 (Santa Cruz) was used as an exogenous substrate. For in vitro kinase assays on Tnik, 3 μg wild type HA-Tnik or 3 μg kinase mutant form of HA-Tnik was expressed in Phoenix-A cells and immunoprecipitated with an anti-HA antibody. Immune complexes were subjected to kinase assays as described above in the absence or presence of 0.5 μg Gelsolin as an exogenous substrate.

Fluorescent microscopy—Phoenix-A cells seeded in 6-well plates were co-transfected with GFP and Tnik constructs as described above. 24 hours after transfection, cells were observed using a Nikon Eclipse TE 300 fluorescent microscope. For detection of apoptosis, Hoechst 33258 (sigma?) was added to transfected Phoenix-A cells (final concentration 5 μg/ml) and the cells were incubated for 30 min at 37° C. before microscopic observation.

Determination of actin distribution—$4 \times 10^5$ Phoenix-A cells in 6-well plate were transfected with 3 pg of control vector, HA-Tnik(WT) or HA-Tnik(KM). 24 hours after transfection, culture media were carefully removed. Cells were lysed directly on the plate using 250 μl Triton X-100 lysis buffer (1% Triton X-100, 150 mM NaCl, 20 mM Tris-HCl, pH 7.4) with protease inhibitors. Cell lysates were centrifuged at 14,000 RPM for 10 min. Supernatants represented the Triton X-100 soluble fraction. Pellets were washed once with 500 μl Triton X-100 lysis buffer and dissolved in 500 μl of 1×SDS sample buffer. DNA was sheared by sonication. This represented the Triton X-100 insoluble fraction. Triton X-100 soluble and insoluble fractions derived from the same number of cells were resolved on SDS-PAGE and blotted with an anti-β-actin mAb to determine the content of F- and G-actin.

Molecular cloning of Tnik—Using a human brain cDNA library and a T/B cell library in our yeast two-hybrid pathway mapping effort, we identified a novel Germinal Center Kinase family member that interacted with both TRAF2 and NCK. The 5' end sequence was cloned from cDNAs prepared from human brain mRNA by RACE-PCR and full length cDNA clones of were obtained by RT-PCR. (FIG. 1).

The longest Tnik clone was encoded by a polypeptide of 1360 amino acids. It had an N-terminal kinase domain, an intermediate domain and a C-terminal Germinal Center Kinase Homology (GCKH) region. It shared about 90% amino acid identity with a previously cloned GCK family member, NCK Interacting Kinase (NIK), in both the kinase domain and the GCKH domain (Su, et al., *EMBO J.*, 16:1279–1290 (1997)). However, Tnik was only 40% identical to NIK in the intermediate region (FIGS. 1, 3). Two shorter clones of Tnik were also obtained: one lacked nucleotides 1338–1424 (amino acids 447–475) and nucleotides 2383–2406 (amino acids 795–802), and the other lacked those two regions plus nucleotides 1609–1773 (aa 537–591) (FIG. 3).

Primers encompassing these three alternatively spliced regions were designed and used for PCR from spleen, heart and brain cDNAs. The relative amounts of the different isoforms, seen as multiple bands amplified from both spleen and brain, varied among the different tissues (FIG. 2). Amplified DNA fragments were cloned into a TA cloning vector and the inserts sequenced. All eight combinations from the alternative splicing of these three regions were identified. These eight spliced isoforms of Tnik were designated as $Tnik_1$ to $Tnik_8$ (FIG. 3). $Tnik_1$ was used in all the experiments described herein.

To determine kinase activity, a putative kinase mutant form of Tnik, designated as Tnik(KM), was constructed with a conserved lysine (Lys-54) residue in the ATP binding pocket mutated to arginine. An HA epitope tag was inserted on the N-terminal portion of Tnik(WT) and Tnik(KM). Both proteins were transiently expressed in Phoenix-A cells, and the expressed proteins were subjected to immunoprecipitation and an in vitro kinase assay. A strong phosphorylated band at 150 kD was detected in the Tnik(WT) expressed lane, but not in the Tnik(KM) expressed lane (FIG. 4, lanes 1, 2). Immunoblotting with an anti-HA antibody showed equal levels of expression of both Tnik(WT) and Tnik(KM) at 150 kD (FIG. 4, lanes 3, 4). Therefore, the phosphorylated band in the in vitro kinase assay represented autophosphorylated Tnik, and the Tnik(KM) mutant was deficient in protein kinase activity.

Tissue distribution of Tnik—The expression pattern of the Tnik message was examined by human multi-tissue Northern blot. Since Tnik shared high homology with NIK, a probe corresponding to nucleotides 1264–2427 of Tnik was used to rule out any potential cross-hybridization. This region shared only 40% amino acid identity with NIK. Three major bands of sizes 6.5 kb, 7.5 kb and 9.5 kb were detected (FIG. 5). Alternative splicing in the coding region described above is unlikely to account for the size differences among the three messages, since the largest isoform is only 273 bps bigger than the smallest isoform. Alternative splicing in the untranslated region or alternative usage of polyA sites could be possible explanations. This phenomenon is not unique to Tnik. NIK and HGK also have multiple message sizes. Tnik is ubiquitously expressed, with higher levels of message detected in heart, brain and skeletal muscle. Interestingly, heart and skeletal muscle predominantly expressed the 6.5 kb form; placenta, kidney and pancreas predominantly expressed the 7.5 kb form; brain, lung and liver expressed all three forms at a similar level. It is currently unknown whether these messages have different functional roles.

Interaction of Tnik with TRAF2 and NCK—To confirm the interaction of Tnik with TRAF2, N-terminal HA-tagged Tnik was transiently expressed in Phoenix-A cells and HA-Tnik was immunoprecipitated by an anti-HA antibody. The immune complexes were resolved on SDS-PAGE and immunoblotted with an anti-TRAF2 antibody. Endogenous TRAF2 specifically co-immunoprecipitated with HA-Tnik (FIG. 6, top panel). To map the interaction domain on Tnik that mediated its interaction with TRAF2, we constructed several truncated forms of HA-tagged Tnik (FIG. 7) and co-expressed them with FLAG-tagged TRAF2. Anti-HA immunoprecipitates were then blotted with an anti-FLAG antibody to detect the co-immunoprecipitated FLAG-TRAF2. Tnik(WT), Tnik(N2), Tnik(C1) and Tnik(M) all co-immunoprecipitated with FLAG-TRAF2, suggesting that the intermediate domain of Tnik is sufficient for Tnik to interact with TRAF2 (FIG. 8, top panel, lanes 1, 3, 4, 6). However, Tnik(C2) consistently showed weak interaction with TRAF2 (lane 5), suggesting that the GCKH domain was also involved in the interaction with TRAF2. Tnik(N1), the Tnik mutant with only the kinase domain, failed to interact with TRAF2 (lane 2). Expression levels of the transfected proteins were controlled by immunoblotting cell lysates with anti-HA and anti-FLAG antibodies (FIG. 8, middle and bottom panels). In addition, $Tnik_8$, the shortest form of Tnik, was still able to interact with Traf2 (data not shown), suggesting that the three alternatively spliced exons were not required for Tnik to interact with Traf2.

We then mapped the domains on TRAF2 that mediated the interaction with Tnik. FLAG-tagged TRAF2 mutants (FIG. 9) were co-expressed with HA-Tnik and the lysates were subjected to anti-HA immunoprecipitation. The immune complexes were then blotted with an anti-FLAG antibody. TRAF2(WT), TRAF2(87–501) and TRAF2 (272–501) were all able to co-immunoprecipitate with HA-Tnik, while TRAF2(1–272) failed to interact with HA-Tnik (FIG. 10, top panel). Immunoblotting cell lysates with anti-HA and anti-FLAG antibodies showed comparable expression levels of the transfected proteins (FIG. 10, middle and bottom panels). This result suggested that the TRAF domain is required for TRAF2 to interact with Tnik. However, since the interaction of full-length TRAF2 with Tnik is stronger then that of either TRAF2(87–501) or TRAF2(272–501), the N-terminal ring finger may directly contribute to the interaction or may stabilize the configuration of the TRAF2 molecule to facilitate this interaction.

Interaction of Tnik with NCK—The interaction of Tnik with NCK was investigated in a similar fashion. Following transient expression of HA-Tnik in Phoenix-A cells, the cell lysates were immunoprecipitated with an anti-HA antibody and blotted with an anti-NCK antibody. Endogenous NCK specifically co-immunoprecipitated with HA-Tnik (FIG. 11, top panel). To map the domains on Tnik required for this interaction, HA-tagged Tnik mutants were co-expressed with FLAG-tagged NCK and the HA-Tnik mutants were immunoprecipitated with an anti-HA antibody. The immune complexes were then blotted with an anti-FLAG antibody. Tnik(WT), Tnik(N2), Tnik(C1) and Tnik(M) were all able to associate with NCK, suggesting that the intermediate domain is also sufficient for Tnik to bind NCK (FIG. 12, top panel, lanes 1, 3, 4, 6). Neither the GCKH domain nor the kinase domain showed any detectable binding to NCK (lanes 2, 5). Immunoblotting cell lysates with anti-HA and anti-FLAG antibodies showed equivalent levels of expression of the transfected preoteins (FIG. 12, middle and bottom panels).

Activation of JNK2 by Tnik—We further examined whether Tnik was able to activate the JNK pathway. 1 µg, 2 µg or 3 µg of Tnik expression plasmid was co-transfected into Phoenix-A cells with Myc-JNK2. 24 hours after transfection, Myc-JNK2 was immunoprecipitated from cell lysates and its kinase activity measured using GST-cJun (1–79) as a substrate. Co-transfection of Tnik enhanced JNK2 kinase activity in a dose dependent fashion (FIG. 13, top panel, lanes 1, 3–5). When 3 µg of Tnik was transfected, JNK2 activity was enhanced 3–4 fold. A similar magnitude of JNK2 activation was observed when cells were treated for 15 minutes with 100 ng/ml of TNF (lanes 1, 2 and 5). Also consistent with published result (Natoli, et al., *Science*, 275:200–203 (1997)), TRAF2 potently activated JNK2 activity (lane 6). The expression levels of Myc-JNK2 were controlled by immunoblotting cell lysates with an anti-Myc antibody (FIG. 13, bottom panel).

To determine whether Tnik can also activate the ERK and p38 pathways, Myc-ERK1 and FLAG-p38 were co-transfected into Phoenix-A cells with different doses of Tnik. The transfected kinases were then immunoprecipitated from cell lysates and the kinase activities measured using MBP and GST-ATF2 as exogenous substrates. In contrast to JNK2, neither ERK1 nor p38 was activated by Tnik overexpression, while co-transfection of MEKK1 potently activated both kinases (FIGS. 14, 15). In addition, Tnik did not activate NF-κB (data not shown).

To further investigate the mechanism of this activation, the cohort of Tnik mutants were co-transfected into Phoenix-A cells with Myc-JNK2 and the ability of these mutants to up-regulate JNK2 kinase activity was examined by the in vitro kinase assay. Tnik(WT), Tnik(KM), Tnik(C1) and Tnik(C2) were all able to activate Myc-JNK2, while Tnik(N1), Tnik(N2), Tnik(M) were not (FIG. 16). This result suggested that the C-terminal GCKH region is both necessary and sufficient for activation of the JNK pathway, while the kinase domain is dispensable.

Regulation of the cytoskeleton by Tnik—When Tnik was overexpressed in Phoenix-A cells, the cells showed a striking morphological change. In control GFP transfected cells, more than 80% of GFP positive cells were adherent and well-spread (FIG. 6A, top row, left panel). In contrast, in Tnik and GFP co-transfected cells, more than 80% of GFP positive cells showed inhibited cell spreading. These cells rounded up and lost attachment to the plate (FIG. 6A, top row, right panel). Similar morphologic change was also observed in Hela and NIH-3T3 cells transfected with Tnik (data not shown). We then transfected the cohort of Tnik mutants into Phoenix-A cells to determine which domain of Tnik was involved in inducing the morphologic change. Tnik(KM), Tnik(C1) and Tnik(C2), which lacked the kinase activity, failed to induce the morphologic change (left column, middle and bottom panels and data not shown), while Tnik(N1) and Tnik(N2) were both competent in inducing the inhibition of cell spreading (FIG. 6A, right column, middle panel and data not shown). Therefore, the kinase domain, rather than the GCKH domain required for JNK activation, was both necessary and sufficient for Tnik to regulate cell spreading. This result suggested that the JNK pathway was not involved in this regulation. Consistent with this hypothesis, overexpression of Myc-JNK failed to inhibit cell spreading (FIG. 6A, right column, bottom panel). Since JNK has been implicated in inducing apoptosis in some cells (Basu, et al., *Oncogene*, 17:3277–3285 (1998)), we examined whether cells transfected with Tnik were undergoing apoptosis. Nuclei of phenix-A cells transfected with control vector, Tnik(WT), Tnik(KM) or RIP were stained with Hoechst 33258(FIG. 6B). No apoptotic body was observed in vector, Tnik(WT) or Tnik(KM) transfected cells, while apotutic bodies were readily detected in greater than 60% of cells transfected with a control RIP cDNA(FIG. 6B). In addition, no activation of caspases was observed in Tnik transfected cells (data not shown). Taken together, these results suggested that Tnik did not induce apotosis in transfected phoenix-A cells.

These observations raised the possibility that overexpression of Tnik might have disrupted intracellular F-actin structure. We therefore examined actin distribution in the Triton X-100 soluble (G-actin) and insoluble (F-actin) fractions in control vector, Tnik and Tnik(KM) transfected Phoenix-A cells. Overexpression of wild type Tnik, but not Tnik(KM), resulted in the enhanced distribution of actin in Triton X-100 soluble fraction, consistent with the reduced spreading observed in these cells (FIG. 6C). We hypothesized that overexpression of Tnik may lead to phosphorylation of cytoskeletal components. Recently, a GCK family protein kinase that could phosphorylate the actin-fragmenting protein Severin was purified and cloned from Dictyostelium (Eichinger, et al., *J. Biol. Chem.*, 273:12952–12959 (1998)). We therefore decided to test whether Tnik was able to phosphorylate the mammalian Severin homologue, Gelsolin (Yin, et al., *Nature*, 281:583–586 (1979)). Tnik and Tnik(KM) were expressed in Phoenix-A cells, immunoprecipitated and incubated in an in vitro kinase assay with purified Gelsolin. Wild type Tnik, but not the kinase mutant form of Tnik, phosphorylated Gelsolin in vitro (FIG. 6D).

Unlike any other GCK family members, both the kinase mutant form of Tnik and the GCKH domain of Tnik were as effective as the wild type protein in JNK2 activation, and the kinase domain alone of Tnik was virtually ineffective (FIG. 16). This result suggested that the C-terminal GCKH domain was solely responsible for the activation. This is in contrast to other GCK family kinases, which activate the JNK pathway either using the kinase domain alone, as is seen with GCKR, HGK and HPK1, or using the kinase domain plus the GCKH region, which is seen with GCK, GLK and NIK (Pombo, et al., *Nature*, 377:750–754 (1995); Shi, et al., *J. Biol. Chem.*, 272:32102–32107 (1997); Kiefer, et al., *EMBO J.*, 15:7013–7025 (1996); Diener, et al., *Proc. Natl. Acad. Sci. USA*, 94:9687–9692 (1997); Yao, et al., *J. Biol. Chem.*, 274:2118–2125 (1999); Su, et al., *EMBO J.*, 16:1279–1290 (1997)). The GCKH domain of NIK interacted with MEKK1, and the dominant negative mutant of MEKK1 inhibited NIK induced JNK activation (Su, et al., *EMBO J.*, 16:1279–1290 (1997)). Given the high level of sequence identity between the GCKH of NIK and the GCKH of Tnik, Tnik likely activated the JNK pathway through MEKK1.

NIK was cloned by its ability to interact with the adapter protein NCK. It associated with NCK SH3 domains via two PxxPxR sequences in the intermediate domain, PCPPSR (aa 574–579; SEQ ID NO:30) and PRVPVR (aa 611–616; SEQ ID NO:31). Both sequences were required for efficient interaction (Su, et al., *EMBO J.*, 16:1279–1290 (1997)). Similar to NIK, Tnik also interacted with NCK via the intermediate domain. However, PCPPSR is not conserved in Tnik. Instead, Tnik contained two other PxxPxR sequences, PNLPPR (aa 562–567; SEQ ID NO:32) and PPLPTR (aa 647–652; SEQ ID NO:36), in addition to the conserved PKVPQR (aa 670–675; SEQ ID NO:33). Tnik likely interacted with NCK through the cooperative interaction with these three PxxPxR sequences. NCK is an adapter protein involved in many growth factor receptor mediated signal transduction pathways (McCarthy, *Bioessays*, 20:913–921 (1998)). It has been proposed that the NIK-NCK interaction may recruit NIK to receptor or non-receptor tyrosine kinases to regulate MEKK1 (Su, et al., *EMBO J.*, 16:1279–1290 (1997)). Tnik may be recruited in a similar fashion.

Tnik also interacts via its intermediate domain with the TRAF domain of TRAF2. Both GCK and GCKR have been previously reported to interact with TRAF2 and it has been suggested that they mediate TRAF2 induced JNK activation (Pombo, et al., *Nature*, 377:750–754 (1995); Diener, et al., *Proc. Natl. Acad. Sci. USA*, 94:9687–9692 (1997); Yuasa, et al., *J. Biol. Chem.*, 273:22681–22692 (1998)). More recently, a Drosophila GCK family member, Misshapen (Msn), has been reported to interact with D-TRAF1 and mediate D-TRAF1 induced JNK activation ( Liu, et al., *Curr. Biol.*, 9:101–104 (1998)). Msn has highest homology to NIK and Tnik. Similar to NIK and Tnik, Msn also interacted with Dock, the Drosophila homologue of NCK (Liu, et al., *Curr. Biol.*, 9:101–104 (1998)). In Drosophila, deficiency in Dock results in defective photoreceptor guidance (Garrity, et al., *Cell*, 85:639–650 (1996)), and in mammalian cells, NCK interacts with WASP, a CDC42 effector protein involved in the regulation of cytoskeleton (Symons, et al., *Cell*, 84:723–734 (1996); Rivero-Lezcano, et al., *Mol. Cell Biol.*, 15:5725–5731 (1995)). These findings strongly suggest that the NCK pathway is closely linked to the cytoskeletal changes. Consistently, Msn deficiency leads to defective dorsal closure that requires extensive cell migration and cell shape changes in addition to the activation of the JNK pathway (Treisman, et al., Gene, 186:119–125 (1997)). Interaction of Msn with Dock may regulate these cell shape changes. Tnik may participate in the regulation of a similar pathway in mammalian cells.

Supporting this hypothesis, overexpression of Tnik inhibited cell spreading in Phoenix-A cells, NIH-3T3 cells and Hela cells (FIG. 6 and data not shown). This effect is likely due to the disruption of filamentous actin structure. No F-actin fiber could be detected by staining with TRITC-Phalloidin of NIH-3T3 cells transfected with a GFP-Tnik fusion protein, while F-actin fibers were abundant in cells transfected with GFP alone (data not shown). Consistent with this notion, overexpression of Tnik resulted in a decreased proportion of actin in the Triton X-100 insoluble fraction (FIG. 19). The Triton X-100 insoluble fraction contains the filamentous actin pool, while the Triton X-100 soluble fraction contains the globular actin monomers. This is the first evidence that a mammalian GCK family member exerts an effect on cytoskeletal organization. A Dictyostelium GCK member was recently cloned that can phosphorylate the Dictyostelium actin fragmenting protein, Severin, in vitro (Eichinger, et al., J. Biol. Chem., 273:12952–12959 (1998)). Interestingly, Tnik can phosphorylate the mammalian Severin homologue, Gelsolin, in vitro (FIG. 20). Gelsolin is also an F-actin fragmenting and capping enzyme that can reduce the content of F-actin. This result suggests that Tnik regulates F-actin assembly through Gelsolin or other related actin severing enzymes. This is consistent with the result that the kinase domain of Tnik is responsible for the regulation of cell spreading (FIG. 17). The mammalian p21-activated kinase, PAK1, which is distantly related to GCK family members and an effector protein of small G proteins Rac1 and CDC42, has been reported to regulate actin cytoskeleton organization. One proposed mechanism of the regulation is through phosphorylation and inhibition of the Myosin Light Chain Kinase (Sanders, et al., Science, 283:2083–2085 (1999)). Overexpression of a constitutively active form of PAK1 also resulted in the inhibition of cell spreading (Garrity, et al., Cell, 85:639–650 (1996)), an effect similar to that caused by overexpression of Tnik (FIGS. 17 and 18).

We claim:

1. An isolated TNIK protein, comprising an amino acid sequence selected from the group consisting of the full length amino acid sequences set forth in SEQ ID NOs:9–15.

2. An isolated TNIK protein, comprising an amino acid sequence encoded by a nucleotide sequence selected from the group consisting of the full length nucleotide sequences set forth in SEQ ID NOs:2–8.

3. The isolated TNIK protein according to claim 1, comprising the full length amino acid sequence set forth in SEQ ID NO:9.

4. The isolated TNIK protein according to claim 1, comprising the full length amino acid sequence set forth in SEQ ID NO:10.

5. The isolated TNIK protein according to claim 1, comprising the full length amino acid sequence set forth in SEQ ID NO:11.

6. The isolated TNIK protein according to claim 1, comprising the full length amino acid sequence set forth in SEQ ID NO:12.

7. The isolated TNIK protein according to claim 1, comprising the full length amino acid sequence set forth in SEQ ID NO:13.

8. The isolated TNIK protein according to claim 1, comprising the full length amino acid sequence set forth in SEQ ID NO:14.

9. The isolated TNIK protein according to claim 1, comprising the full length amino acid sequence set forth in SEQ ID NO:15.

10. The isolated TNIK protein according to claim 2, comprising an amino acid sequence encoded by the full length nucleotide sequence set forth in SEQ ID NO:2.

11. The isolated TNIK protein according to claim 2, comprising an amino acid sequence encoded by the full length nucleotide sequence set forth in SEQ ID NO:3.

12. The isolated TNIK protein according to claim 2, comprising an amino acid sequence encoded by the full length nucleotide sequence set forth in SEQ ID NO:4.

13. The isolated TNIK protein according to claim 2, comprising an amino acid sequence encoded by the full length nucleotide sequence set forth in SEQ ID NO:5.

14. The isolated TNIK protein according to claim 2, comprising an amino acid sequence encoded by the full length nucleotide sequence set forth in SEQ ID NO:6.

15. The isolated TNIK protein according to claim 2, comprising an amino acid sequence encoded by the full length nucleotide sequence set forth in SEQ ID NO:7.

16. The isolated TNIK protein according to claim 2, comprising an amino acid sequence encoded by the full length nucleotide sequence set forth in SEQ ID NO:8.

* * * * *